United States Patent
Mac An Tuile et al.

(10) Patent No.: US 12,408,904 B2
(45) Date of Patent: Sep. 9, 2025

(54) HANDSWITCH AND CONNECTOR FOR POWERED SURGICAL HANDPIECE

(71) Applicant: Stryker European Operations Limited, Carrigtwohill (IE)

(72) Inventors: Conor Mac An Tuile, Muine Bheag (IE); Krishnamurthy Belagali, Bangalore (IN); Aidan Raftery, Ballinasloe (IE); Michael Moloney, Carrick-On-Suir (IE); Dustin James Payne, Kalamazoo, MI (US)

(73) Assignee: Stryker European Operations Limited, Carrigtwohill (IE)

( * ) Notice: Subject to any disclaimer, the term of this patent is extended or adjusted under 35 U.S.C. 154(b) by 953 days.

(21) Appl. No.: 17/602,920

(22) PCT Filed: Apr. 10, 2020

(86) PCT No.: PCT/IB2020/053441
§ 371 (c)(1),
(2) Date: Oct. 11, 2021

(87) PCT Pub. No.: WO2020/208598
PCT Pub. Date: Oct. 15, 2020

(65) Prior Publication Data
US 2022/0175353 A1    Jun. 9, 2022

Related U.S. Application Data

(60) Provisional application No. 62/884,765, filed on Aug. 9, 2019, provisional application No. 62/832,983, filed on Apr. 12, 2019.

(51) Int. Cl.
*A61B 17/00* (2006.01)
*H01H 21/22* (2006.01)

(52) U.S. Cl.
CPC ............. *A61B 17/00* (2013.01); *H01H 21/22* (2013.01); *A61B 2017/00017* (2013.01);
(Continued)

(58) Field of Classification Search
CPC .......... A61B 17/00; A61B 2017/00017; A61B 2017/00398; A61B 2017/00424; A61B 2017/00477; H01H 21/22
(Continued)

(56) References Cited

U.S. PATENT DOCUMENTS 3,937,547 A   2/1976   Lee-Kemp
4,155,619 A   5/1979   Bray et al.
(Continued)

FOREIGN PATENT DOCUMENTS

WO    2017167749 A1    10/2017

OTHER PUBLICATIONS

English language abstract for WO 2017/167749 A1 extracted from espacenet.com database on Oct. 19, 2021, 1 page.
(Continued)

*Primary Examiner* — Aaron F Roane
(74) *Attorney, Agent, or Firm* — Howard & Howard Attorneys PLLC

(57) ABSTRACT

A handswitch (50) for a powered surgical handpiece (54) comprises a mounting base (62), a lever (70), a spring, a run-safe switch (68) and a lever extension. The mounting base defines a pivot axis. The elongated lever defines a lever axis substantially normal to a direction of the pivot axis. The lever includes a proximal end pivotably connected to the mounting base at the pivot axis and a distal end opposite the proximal end. The first track is on an inner side of the lever. The second track is on an outer side of the lever opposite the inner side, with both tracks substantially parallel to the lever axis. The spring is between the base and the lever and biases (Continued)

the lever about the pivot axis. The run-safe switch is slidably disposed on the first track. The lever extension is slidably disposed on the second track.

19 Claims, 40 Drawing Sheets

(52) U.S. Cl.
CPC .............. *A61B 2017/00398* (2013.01); *A61B 2017/00424* (2013.01); *A61B 2017/00477* (2013.01)

(58) Field of Classification Search
USPC .............................................................. 606/1
See application file for complete search history.

(56) References Cited

U.S. PATENT DOCUMENTS

| | | |
|---|---|---|
| 6,017,354 A | 1/2000 | Culp et al. |
| 6,945,981 B2 | 9/2005 | Donofrio et al. |
| 7,297,013 B2 | 11/2007 | Caveney et al. |
| 7,909,840 B2 | 3/2011 | Cote et al. |
| 8,021,365 B2 | 9/2011 | Phan |
| 8,197,501 B2 | 6/2012 | Shadeck et al. |
| 8,545,527 B2 | 10/2013 | Shadeck et al. |
| 8,657,808 B2 | 2/2014 | McPherson et al. |
| 8,956,342 B1 | 2/2015 | Russo et al. |
| 9,585,676 B1 | 3/2017 | Russo et al. |
| 9,748,057 B2 | 8/2017 | Blus et al. |
| 10,014,627 B2 | 7/2018 | Toh et al. |
| 10,130,383 B2 | 11/2018 | Dickerson et al. |
| 2004/0157499 A1 | 8/2004 | Nania et al. |
| 2005/0222571 A1 | 10/2005 | Ryan |
| 2009/0240272 A1 | 9/2009 | Shadeck et al. |
| 2011/0266124 A1 | 11/2011 | Culp et al. |
| 2013/0197491 A1 | 8/2013 | Golden et al. |
| 2014/0235085 A1 | 8/2014 | Su et al. |
| 2015/0209071 A1 | 7/2015 | Miller et al. |
| 2016/0287265 A1 | 10/2016 | Macdonald et al. |
| 2017/0000496 A1 | 1/2017 | Hershberger |
| 2017/0007219 A1 | 1/2017 | Bucina et al. |
| 2018/0014820 A1* | 1/2018 | Garadi .............. A61B 17/1626 |
| 2018/0078298 A1 | 3/2018 | Gonzalez et al. |
| 2018/0257214 A1 | 9/2018 | Scheuber et al. |
| 2020/0297332 A1 | 9/2020 | Kahler et al. |

OTHER PUBLICATIONS

International Search Report for Application No. PCT/IB2020/053441 dated Aug. 12, 2020, 4 pages.
Panduit, "Webpage", https://www.panduit.com/en/about.html, 2021, 8 pages.
Partial International Search Report for Application No. PCT/IB2020/053441 dated Jun. 12, 2020, 4 pages.
VOLEX PLC, "Webpage", https://www.volex.com/overview/, 2021, 4 pages.

* cited by examiner

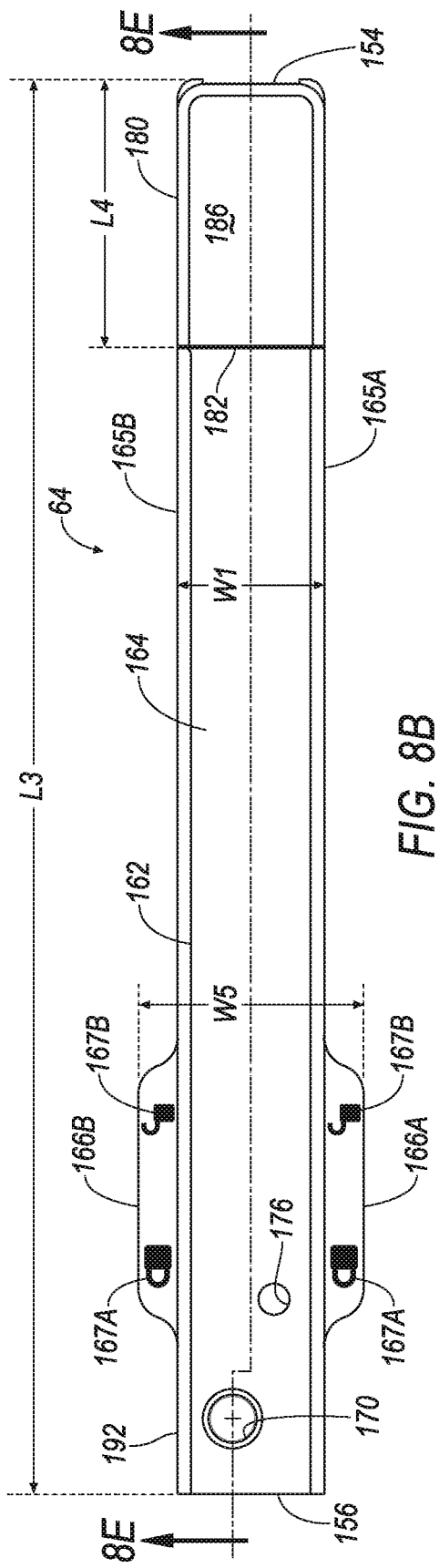
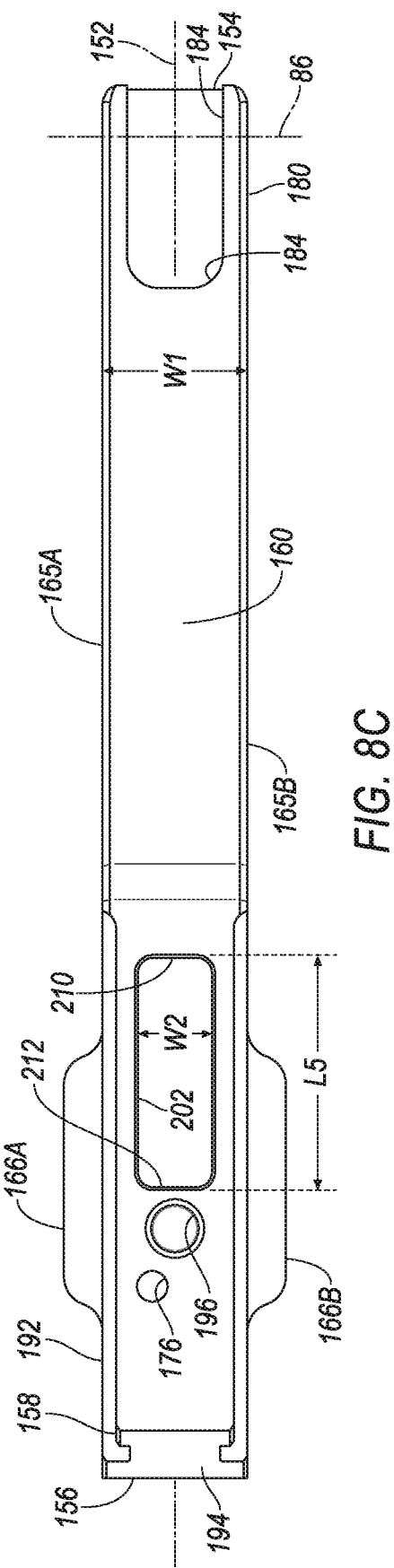
FIG. 8B
FIG. 8C

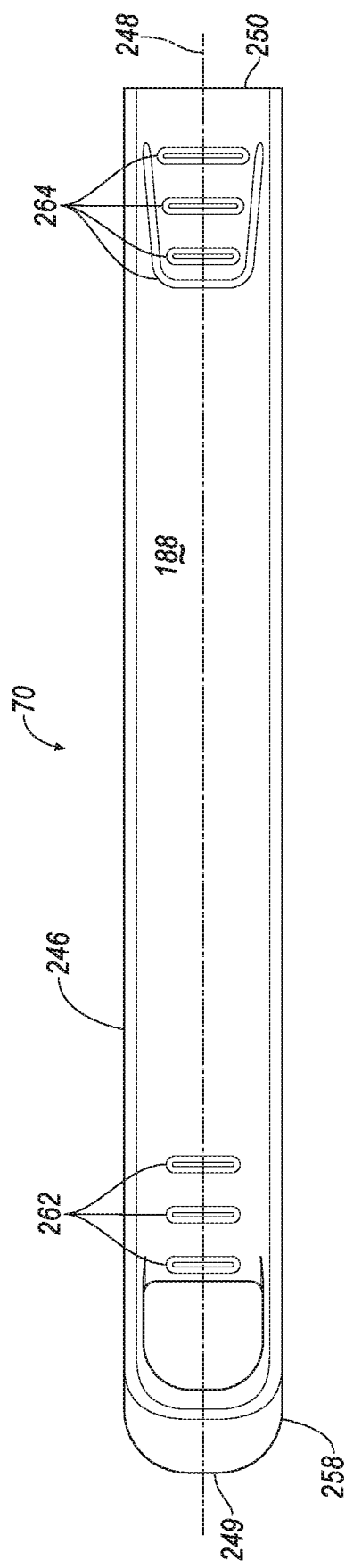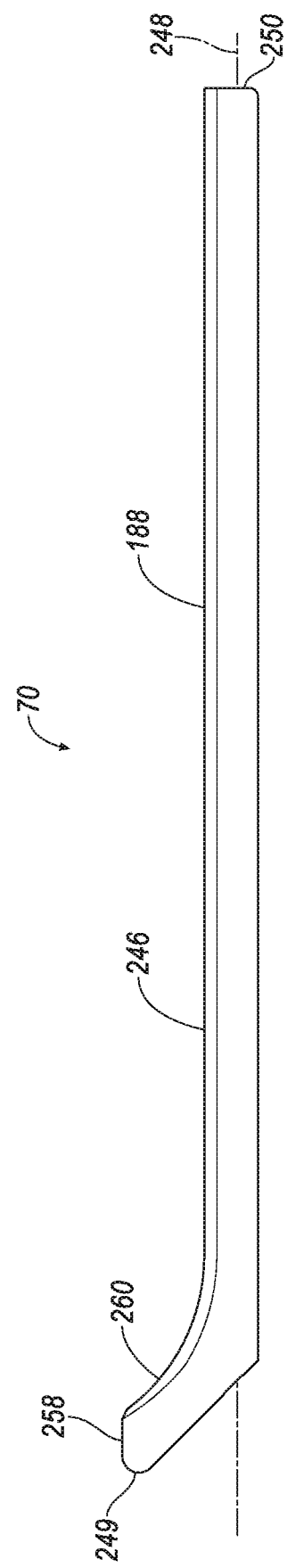
FIG. 9B
FIG. 9C

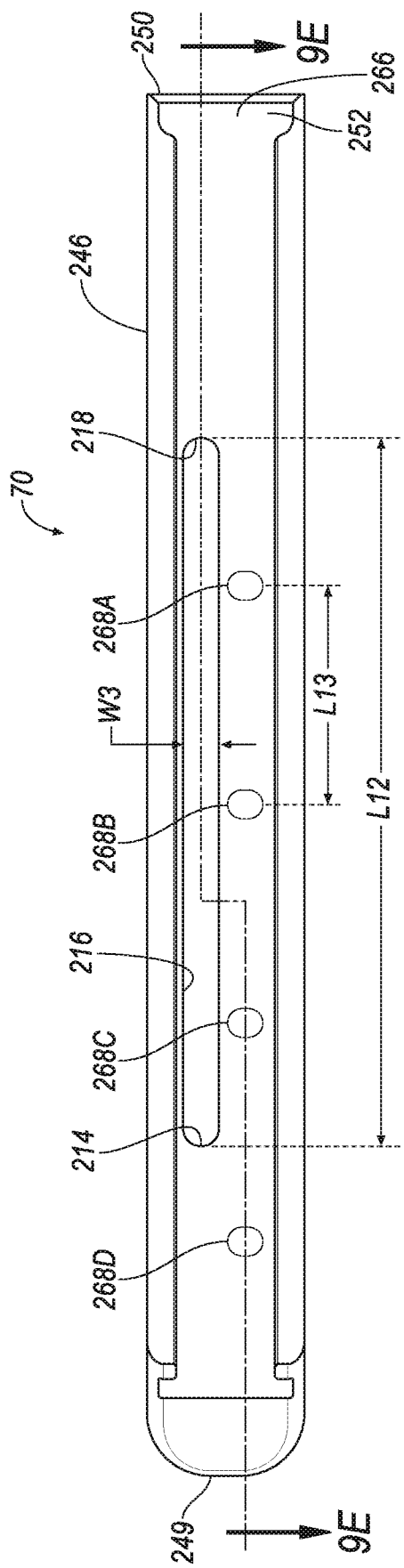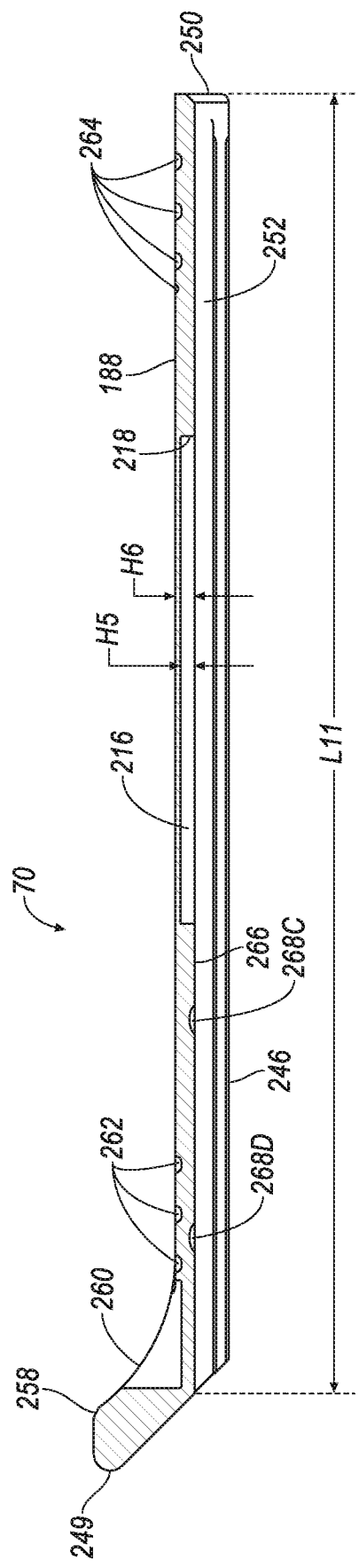
FIG. 9D
FIG. 9E

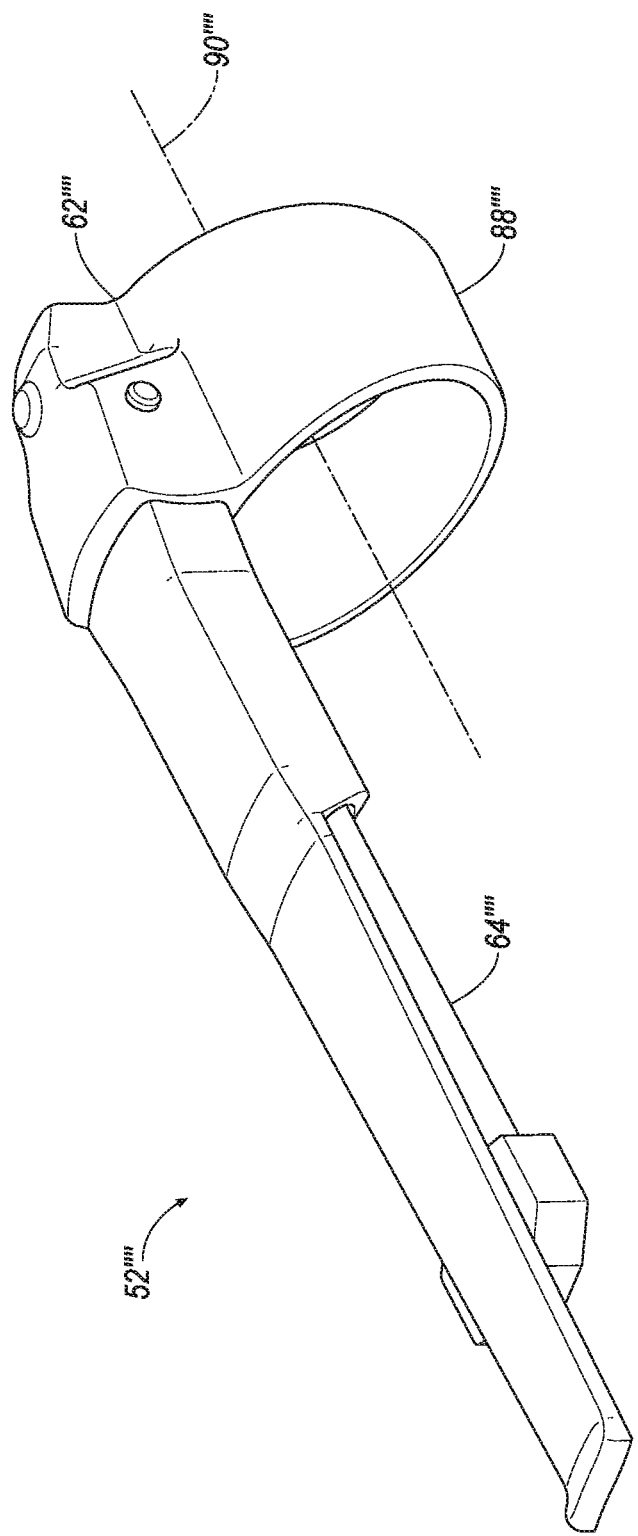

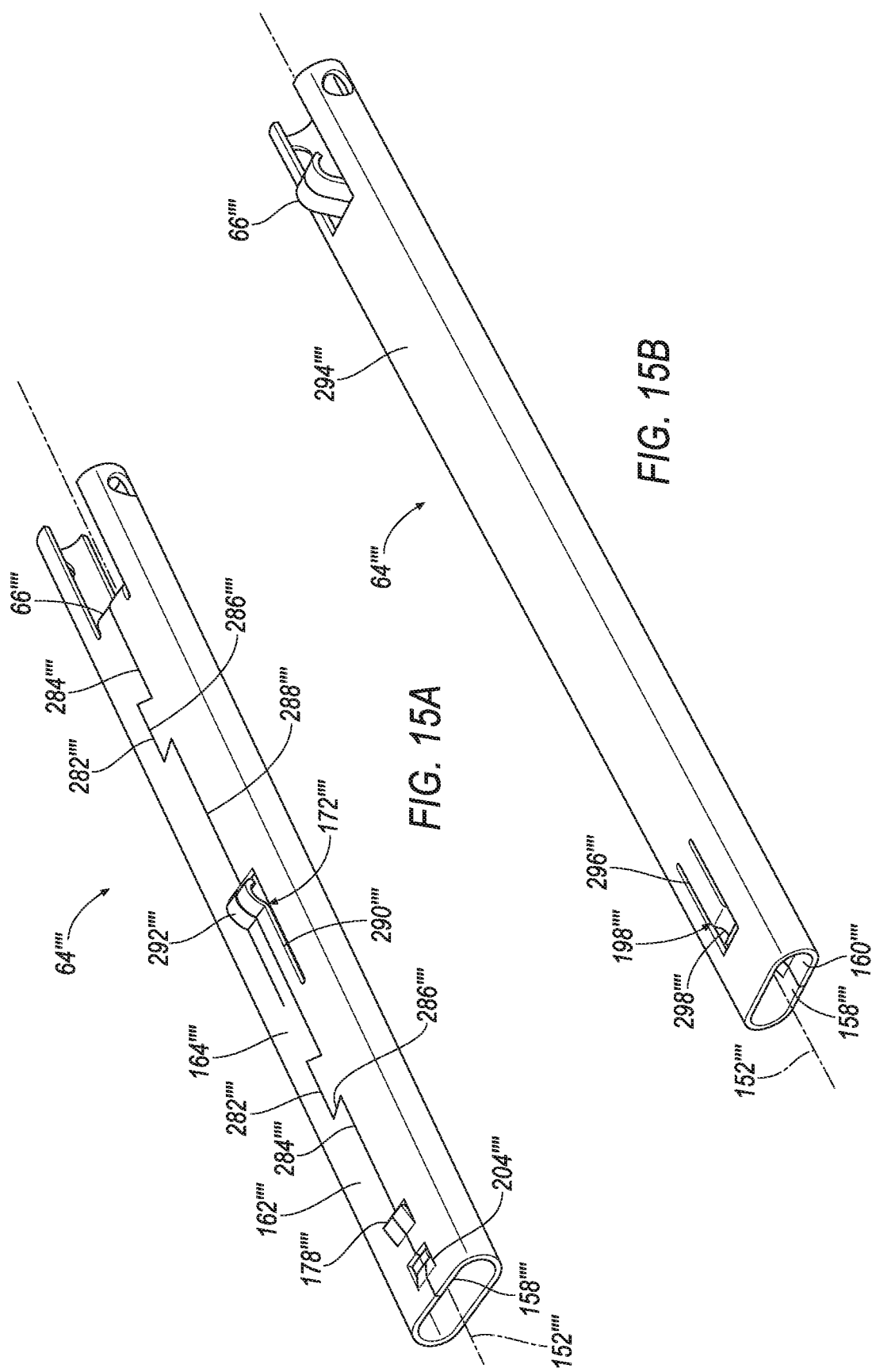

HANDSWITCH AND CONNECTOR FOR POWERED SURGICAL HANDPIECE

RELATED APPLICATIONS

This application is the National Stage entry of International Patent Application No. PCT/IB2020/053441, filed April 10, 2020, which claims priority to and all the benefits of both U.S. Provisional Patent Application No. 62/832,983, filed on Apr. 12, 2019, and U.S. Provisional Patent Application No. 62/884,765, filed on Aug. 9, 2019, the entire contents of each of which are hereby incorporated by reference.

BACKGROUND

A handswitch for powered surgical handpieces that is easier to install and provides improved convenience of operation is desired.

BRIEF DESCRIPTION OF THE DRAWINGS

FIG. 8B is a top view of the lever of FIG. 8A.

FIG. 8C is a bottom view of the lever of FIG. 8A.

FIG. 9B is a top view of the lever extension of FIG. 9A.

FIG. 9C is a right-side view of the lever extension of FIG. 9A.

FIG. 9D is a bottom view of the lever extension of FIG. 9A.

FIG. 9E is a sectional view of the lever extension of FIG. 9A taken in the direction of arrows 9E of FIG. 9D.

FIG. 14A is a perspective view of an alternative handswitch.

FIG. 15A is a top right front perspective view of a lever of the handswitch of FIG. 14A.

FIG. 15B is a bottom left front perspective view of the lever of the handswitch of FIG. 14A.

DETAILED DESCRIPTION

Figure 1:
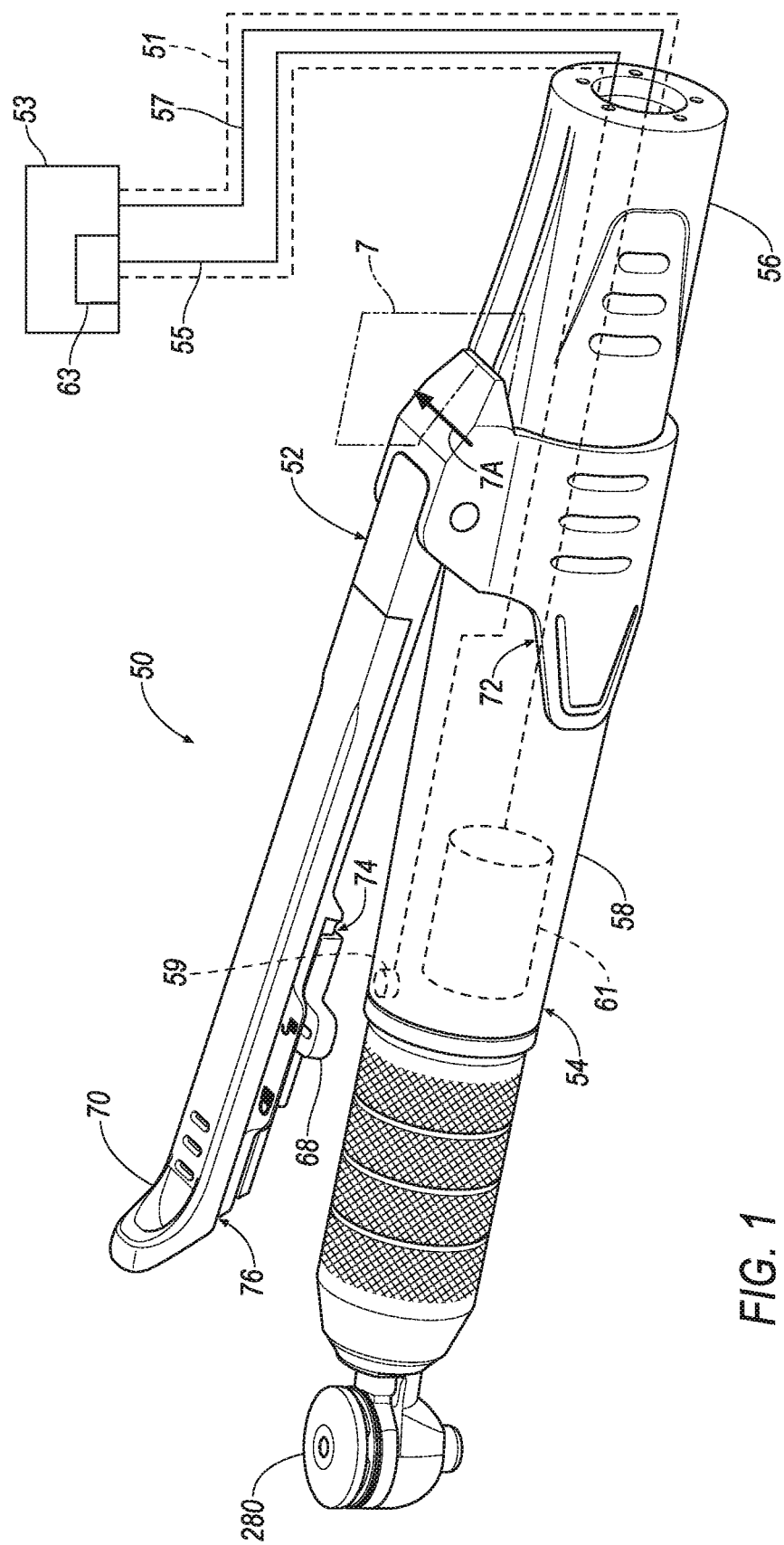
FIG. 1 is a perspective view of a handswitch disposed on a handpiece, with the handpiece and handswitch engaged by a connector.

The prior art does not address the need to provide an ergonomically optimized handswitch for a powered surgical handpiece.

A handswitch for a powered surgical handpiece comprises a mounting base, a lever, a spring, a run-safe switch and a lever extension. The mounting base defines a pivot axis. The elongated lever defines a lever axis substantially normal to a direction of the pivot axis. The lever includes a proximal end pivotably connected to the mounting base at the pivot axis and a distal end opposite the proximal end. The first track is on an inner side of the lever. The second track is on an outer side of the lever opposite the inner side, with both tracks substantially parallel to the lever axis. The spring is between the base and the lever and biases the lever about the pivot axis. The run-safe switch is slidably disposed on the first track. The lever extension is slidably disposed on the second track.

The handswitch and the features thereof may comprise additional features and modifications as set forth below, such features and modifications being included separately or in combination with each other, with such combinations being limited only by mutual exclusivity.

At least one of the first track and the second track of a handswitch may be one of a T-slot and a T-track.

The first track and the second track of a handswitch may both be T-tracks.

The lever of a handswitch may have first and second lateral sides connecting the inner and outer sides. The run-safe switch of a handswitch may have at least one outboard side extending laterally beyond at least one of the lateral sides of the lever.

The outboard side of the lever of a handswitch may be defined by an indicator arm.

The lever of a handswitch may have a slot in the inner side that is in receipt of at least one of a magnet and a magnet retainer fixed to the run-safe switch.

The slot in the lever of a handswitch may be shorter in length than a length of the lever. The slot may define a travel range of the run-safe switch.

A detent may be disposed in a handswitch between the run-safe switch and the lever.

A detent in a handswitch between the run-safe switch and the lever may include a run-safe switch plunger and a first notch associated with an active position of the run-safe switch and a second notch associated with an inactive position of the run-safe switch.

A handswitch may have the run-safe switch plunger disposed in the lever and the notches disposed on the switch.

A handswitch may have a detent disposed between the lever and the lever extension.

A detent in a handswitch between the lever and the lever extension may include an extension plunger and first, second, third and fourth notches respectively associated with first, second, third and fourth positions of the extension.

The extension plunger of a detent in a handswitch between the lever and the lever extension may be disposed in the lever and the notches may be disposed in the lever extension.

The mounting base of a handswitch may include an annular collar that defines a mounting axis substantially normal to at least the direction of the pivot axis. The collar may be sized for slideable disposition over a proximal end of the handpiece.

The annular collar of a handswitch may define a positioning tab extending axially in a distal direction, the tab including an angled wedge side. The annular collar may further include on an inner diameter thereof one of a detent plunger and a detent notch defining a biasing surface.

The annular collar of a handswitch may include at least a second positioning tab. The second positioning tab may also extend axially in the distal direction and may include an angled wedge side.

The detent plunger of a mounting base detent of a handswitch may be disposed in the collar.

A surgical tool comprises a power surgical handpiece and a handswitch. The power surgical handpiece includes a longitudinally extending handpiece and a magnetic field sensor. The longitudinally extending handpiece housing extends along a housing axis. The magnetic field sensor is disposed in the housing. The handswitch comprises a mounting base, an elongated lever, a spring, a run-safe switch, and a lever extension. The mounting base defines a pivot axis having a direction substantially normal to the housing axis, and a mounting surface extending in a first direction. The elongated lever defines a lever axis substantially normal to the direction of the pivot axis. The lever includes a proximal end, a distal end, a first track, and a second track. The proximal end is pivotably connected to the mounting base at the pivot axis. The distal end is opposite the proximal end. The first track is on an inner side substantially facing the housing axis. The second track is on an outer side opposite the inner side with both tracks substantially parallel to the lever axis. The spring is between the base and the lever and biases the lever about the pivot axis. The run-safe switch is slidably disposed on the first track and has a magnet fixed thereto. The lever extension is slidably disposed on the second track.

The surgical tool and the features thereof may comprise additional features and modifications as set forth below, such features and modifications being included separately or in combination with each other, with such combinations being limited only by mutual exclusivity At least one of the first track and the second track of a handswitch may be one of a T-slot and a T-track.

The first track and the second track of a handswitch may both be T-tracks.

The lever of a handswitch may have first and second lateral sides connecting the inner and outer sides. The run-safe switch of a handswitch may have at least one outboard side extending laterally beyond at least one of the lateral sides of the lever.

The outboard side of the lever of a handswitch may be defined by an indicator arm.

The lever of a handswitch may have a slot in the inner side that is in receipt of at least one of a magnet and a magnet retainer fixed to the run-safe switch.

The slot in the lever of a handswitch may be shorter in length than a length of the lever. The slot may define a travel range of the run-safe switch.

A detent may be disposed in a handswitch between the run-safe switch and the lever.

A detent in a handswitch between the run-safe switch and the lever may include a run-safe switch plunger and a first notch associated with an active position of the run-safe switch and a second notch associated with an inactive position of the run-safe switch.

A handswitch may have the run-safe switch plunger disposed in the lever and the notches disposed on the switch.

A handswitch may have a detent disposed between the lever and the lever extension.

A detent in a handswitch between the lever and the lever extension may include an extension plunger and first, second, third and fourth notches respectively associated with first, second, third and fourth positions of the extension.

The extension plunger of a detent in a handswitch between the lever and the lever extension may be disposed in the lever and the notches may be disposed in the lever extension.

The mounting base of a handswitch may include an annular collar that defines a mounting axis substantially normal to at least the direction of the pivot axis. The collar may be sized for slideable disposition over a proximal end of the handpiece.

The annular collar of a handswitch may define a positioning tab extending axially in a distal direction, the tab including an angled wedge side. The annular collar may further include on an inner diameter thereof one of a detent plunger and a detent notch defining a biasing surface.

The annular collar of a handswitch may include at least a second positioning tab. The second positioning tab may also extend axially in the distal direction and may include an angled wedge side.

The detent plunger of a mounting base detent of a handswitch may be disposed in the collar.

A handswitch for a powered surgical handpiece comprises a mounting base, an elongated lever, a spring, a run-safe switch, and a mounting base. The mounting base defines a pivot axis and includes an annular collar defining a mounting axis substantially normal to at least a direction of the pivot axis. The collar is sized for slideable disposition over a proximal end of the handpiece in a direction of the mounting axis. The elongated lever is pivotably connected to the mounting base at a proximal end of the lever. The spring is between the base and the lever, biasing the lever about the pivot axis. The run-safe switch is slidably disposed on the lever. The mounting base further comprises a first positioning tab and a second positioning tab of the collar. Each tab extends axially in a distal direction from a main portion of the collar. Each tab includes an angled wedge side. An inner diameter of the annular collar has disposed thereon one of a detent notch defining a biasing surface and a detent plunger.

The handswitch and the features thereof may comprise additional features and modifications as set forth below, such features and modifications being included separately or in combination with each other, with such combinations being limited only by mutual exclusivity.

Each tab of the handswitch may include an angled wedge side.

Each tab of the handswitch may have a tab centerline about which the tab is substantially symmetrical. Each tab may have two angled wedge sides.

Both tab centerlines of the handswitch may be a predetermined distance below the mounting axis, and on an opposite side of the mounting axis from the pivot axis.

The collar of the handswitch may have the detent plunger disposed in the collar.

The run-safe switch of the handswitch may be slidably disposed on an inner side of the lever.

The handswitch may have a lever extension slidably disposed on an outer side of the lever.

A surgical tool comprises a power surgical handpiece and a handswitch. The power surgical handpiece comprises a longitudinally extending handpiece housing and a magnetic field sensor. The longitudinally extending handpiece housing may extend along a housing axis. The magnetic field sensor may be disposed in the housing. The handswitch comprises a mounting base, an elongated lever, a spring, a run-safe switch. The mounting base defines a pivot axis and includes an annular collar. The annular collar defines a mounting axis substantially normal to at least a direction of the pivot axis. The annular collar is sized for slideable disposition over a proximal end of the handpiece in a direction of the mounting axis. The elongated lever is pivotably connected to the mounting base at a proximal end of the lever. The spring is between the base. The spring biases the lever about the pivot axis. The run-safe switch is slidably disposed on the lever. The mounting base further comprises a first positioning tab and a second positioning tab of the collar. Each of the tabs extend axially in a distal direction from a main portion of the collar. Each tab includes an angled wedge side. The mounting base further comprises one of a detent notch defining a biasing surface, and a detent plunger, such being disposed on an inner diameter of the annular collar.

The surgical tool and the features thereof may comprise additional features and modifications as set forth below, such features and modifications being included separately or in combination with each other, with such combinations being limited only by mutual exclusivity.

The handswitch may have each tab include an angled wedge side.

Each tab of the handswitch may have a tab centerline about which the tab is substantially symmetrical. Each tab may have two angled wedge sides.

Both tab centerlines of the handswitch may be a predetermined distance below the mounting axis, and on an opposite side of the mounting axis from the pivot axis.

The collar of a handswitch may have the detent plunger disposed in the collar.

The run-safe switch of a handswitch may be slidably disposed on an inner side of the lever.

A handswitch may have a lever extension slidably disposed on an outer side of the lever.

A surgical tool may further comprise two receiving channels and a plurality of contact points. The housing may include the two receiving channels. The channels may formed on the proximal end of the housing. The receiving channels may be defined at least in part by a peripheral wall and the channels extending axially away from a proximal end of the housing toward a distal end of the housing. A first side of each channel may define a first channel contact point thereof. A second side of each channel defining a second channel contact point thereof. Each positioning tab may extend a second predetermined length in a distal direction. Each tab may include a first side defining a first tab contact point thereof and a second side defining a second tab contact point thereof. When the collar is in engagement with the housing, each first tab contact point is in contact with the first channel contact point of the respective channel, and each second tab contact point is in contact with the second channel contact point of the respective channel. One of a detent plunger and a sloped groove defining a biasing surface may be disposed on an inner diameter of the collar.

The surgical tool and the features thereof may comprise additional features and modifications as set forth below, such features and modifications being included separately or in combination with each other, with such combinations being limited only by mutual exclusivity.

A surgical tool may include a notch in the housing defining the biasing surface and the detent plunger may be disposed on the inner diameter of the collar.

A surgical tool may include the biasing surface facing distally in part. The biasing surface may be engaged by the plunger when the respective contact points of the tabs and the channels are in engagement.

An electrical connector for a surgical tool, the connector comprises an axially extending cable end receiver and an outer sleeve. The axially extending cable end receiver in turn comprises an inner sleeve and a pin holder. The inner sleeve comprises a resilient clip that includes a first retention wedge. The pin holder is fixed to the inner sleeve and comprises a core and a plurality of pins fixed to the core. The outer sleeve is in slidable receipt of substantially an entirety of the cable end receiver. The outer sleeve includes a first window in receipt of the retention wedge. The outer sleeve has a slidable range relative to the receiver. The slidable range extends from a latching position with the wedge in substantial axial alignment with the window, to a releasing position with wedge being axially offset from alignment with the window.

An electrical cable assembly for use with a surgical tool comprises a cable and a connector. The cable comprises a plurality of conductors. The connector comprises an axially extending cable end receiver and an outer sleeve. The axially extending cable end receiver comprising an inner sleeve and a pin holder. The inner sleeve comprises a resilient clip including a first retention wedge. The pin holder comprises a core and a plurality of pins fixed to the core. The pin holder is fixed to the inner sleeve and is entirely disposed therein. The outer sleeve is in slidable receipt of substantially an entirety of the cable end receiver. The outer sleeve includes a first window in receipt of the retention wedge. The outer sleeve has a slidable range relative to the receiver with the range extending from a latching position with the wedge in substantial axial alignment with the window to a releasing position with wedge being axially offset from alignment with the window. A plurality of the conductors are electrically connected to a plurality of the pins.

A surgical system comprising a handpiece and a cable assembly. The handpiece comprises a housing and an electric drive motor disposed therein. The cable assembly comprises a cable and a connector. The cable comprises a plurality of conductors. The connector comprises an axially extending cable end receiver and an outer sleeve. The axially extending cable end receiver comprising an inner sleeve and a pin holder. The inner sleeve comprises a resilient clip including a first retention wedge. The pin holder comprises a core and a plurality of pins fixed to the core. The pin holder is fixed to the inner sleeve and is entirely disposed therein. The outer sleeve is in slidable receipt of substantially an entirety of the cable end receiver. The outer sleeve includes a first window in receipt of the retention wedge. The outer sleeve has a slidable range relative to the receiver with the range extending from a latching position with the wedge in substantial axial alignment with the window to a releasing position with wedge being axially offset from alignment with the window. A plurality of the conductors are electrically connected to a plurality of the pins.

Each of the above-referenced electrical connector, electrical cable assembly, and surgical system may be refined, i.e., modified, as stated below. Such refinements or modifications may be combined with any of the others without limitation to the extent they are not mutually exclusive.

The cable end receiver may further comprise a bushing disposed between the pin holder and the inner sleeve.

The bushing may include cable engagement feet extending radially inwardly for engagement of the cable.

The bushing may be disposed entirely within the inner sleeve.

The releasing position of the outer sleeve relative to the cable end receiver may be proximal relative to the latching position of the outer sleeve.

In the releasing position, a ramp surface of the wedge may be in engagement with a second surface of the window and a stop surface of the wedge may be spaced from a first surface of the window.

The cable end receiver may further comprise a retaining nut disposed over the inner sleeve and threadably fixed thereto.

The outer sleeve may have a raised alignment surface.

The resilient clip may further comprise a beam fixed to the inner sleeve at both ends, and the wedge may be fixed to the beam between the ends thereof.

The inner sleeve may further comprise a second wedge and the outer sleeve may comprise a second window.

Relative orientations and directions (byway of example, distal, proximal, upper, lower, bottom, rearward, front, rear, back, outboard, inboard, inward, outward, lateral, left, right) are set forth in this description not as limitations, but for the convenience of the reader in picturing at least one embodiment of the structures described. Such exemplary orientations may be from the perspective of a user of the saw.

The elements shown may take many different forms and include multiple and/or alternate components and facilities. The example components illustrated are not intended to be limiting. Indeed, additional or alternative components and/or implementations may be used. Further, the elements shown are not necessarily drawn to scale unless explicitly stated as such.

As illustrated in FIGS. 1-23, an example surgical tool 50 includes an example handswitch 52, an example powered surgical handpiece 54, and an example electrical connector 56. The example handswitch 52 may be selectively mounted to an example longitudinally extending handpiece housing 58 of the example powered surgical handpiece 54. The example connector 56, selectively connectable to a proximal end 60 of the handpiece 54, may aid in retaining the handswitch 52 on the housing 58. When connected to the handpiece 54, the connector 56 may electrically connect the handpiece 54 via an electrical cable 51 (shown in phantom in FIG. 1) to a console 53 for communication of control signals and electrical power therebetween.

The cable 51 and the housing 58 may include a signal conductor 55, e.g., a wire, and a power conductor 57. The signal conductor 55 may be electrically connected to a magnetic field sensor 59 disposed in the housing 58 and to a controller 63 that may be disposed in the console 53. The power conductor 57 may be connected to a drive motor 61 disposed in the housing. The drive motor 61 may be powered by any conventional means, e.g., electrical power, pneumatic power. The power conductor 57 may be, by way of example and not limitation, a wire or a pneumatic hose. Each of the conductors 55, 57 may be comprised of an in-housing portion and an in-cable portion that may connect at a proximal end of the connector 56 or the proximal end 60 of the handpiece 54. The controller 63 may be programmed to control power to the electric drive motor 61 responsive to signals from sensors, e.g., the magnetic field sensor 59. The controller 63 may also be electrically connected to other sensors (not shown), with other sensors potentially including switches, e.g., a user-controlled foot switch (not shown). Alternatively, the handpiece 54 may include a battery as a power source, and may communicate signals wirelessly with the console 53. Yet alternatively, the connector 56 may be a wireless connector and may include one or both of a battery and a wireless communication device, e.g., a dongle.

The handswitch 52 includes an example mounting base 62, an example lever 64 pivotably connected to the mounting base 62, an example switch spring 66 disposed between the mounting base 62 and the lever 64 biasing the lever 64 away from the handpiece housing 58, a run-safe switch 68, i.e., an unlocked-locked switch 68, slidably disposed on the lever 64, and a lever extension 70, also slidably disposed on the lever 64.

The base 62 and the handpiece housing 58 cooperatively define an example alignment interface 72. The run-safe switch 68 and the lever 64 cooperatively define an example run-safe switch interface 74. The lever extension 70 and the lever 64 cooperatively define an example extension interface 76. Each of the lever 64, the lever extension 70, the switch 68, the base 62 and the housing 58 include features that define the interfaces 72, 74, 76 with such features being described in more detail below. The example interfaces 72, 74, 76 may define one or more relative positions between the respective components as is also described in more detail below.

The mounting base 62 may include a first ear 78A and a second ear 78B. The ears 78A, 78B define a receiving pocket 80. A proximal tab 82, which may serve as a visual alignment cue to a user in aligning of the connector 56 with the handpiece 54, may be provided on a distal end of the mounting base 62 and may define a closure at a proximal end of the pocket 80.

The ears 78A, 78B may be respectively pierced by a first ear aperture 84A and a second ear aperture 84B, the apertures 84A, 84B aligned with each other on a pivot axis 86 defined by the apertures 84A, 84B.

Figure 5A:
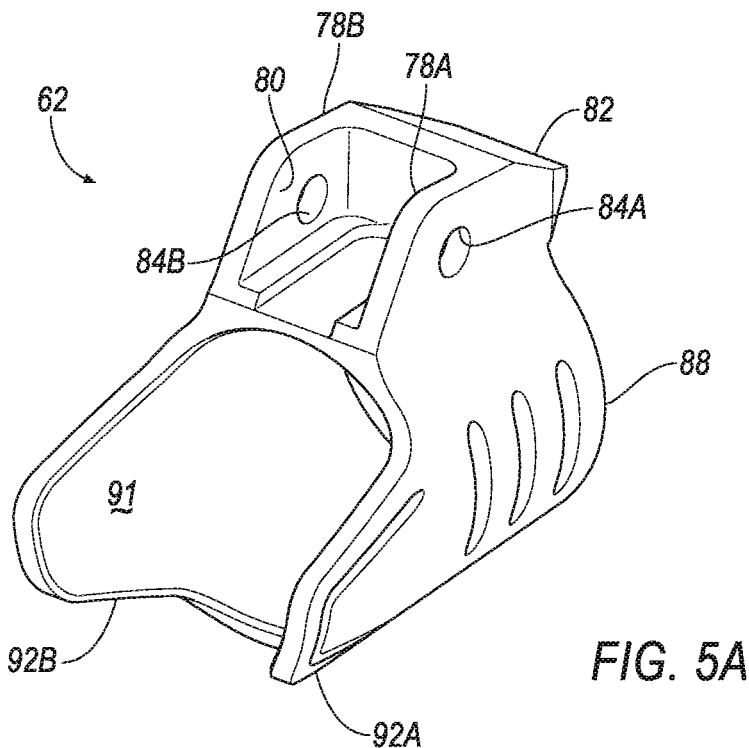
FIG. 5A is a first perspective view of a collar of the handswitch of FIG. 4.
Figure 5B:
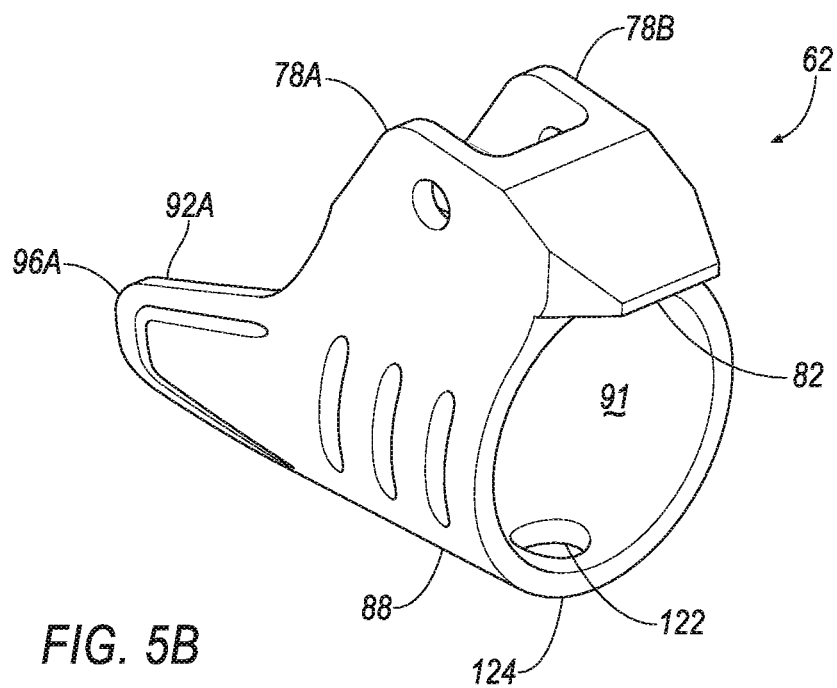
FIG. 5B is a second perspective view of the collar FIG. 5A.
Figure 5C:
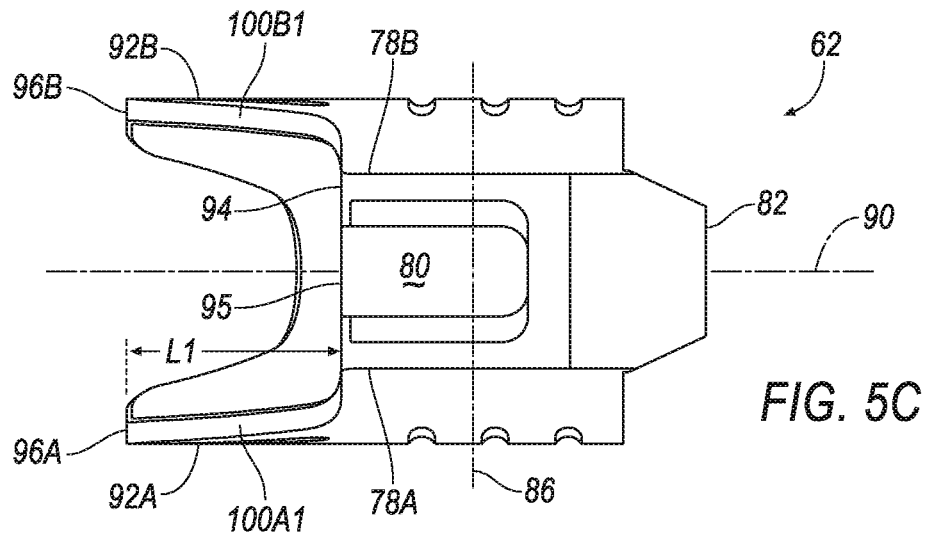
FIG. 5C is a top view of the collar of FIG. 5A.

The mounting base 62 may also include as part of the alignment interface 72 an example annular collar 88 that defines a mounting axis 90. The collar 88 may have an inside diameter D1 defining an annular mounting surface 91 centered about the axis 90. The collar 88 may be sized for removable slidable receipt by the proximal end 60 of the housing 58. An example nominal value of D1 may be approximately 20 mm (0.80 inches). The pivot axis 86 and the mounting axis 90, while not intersecting, may be perpendicular to each other when viewed from a direction perpendicular to both axes 86, 90, e.g. as shown in FIG. 5C.

Figure 5D:
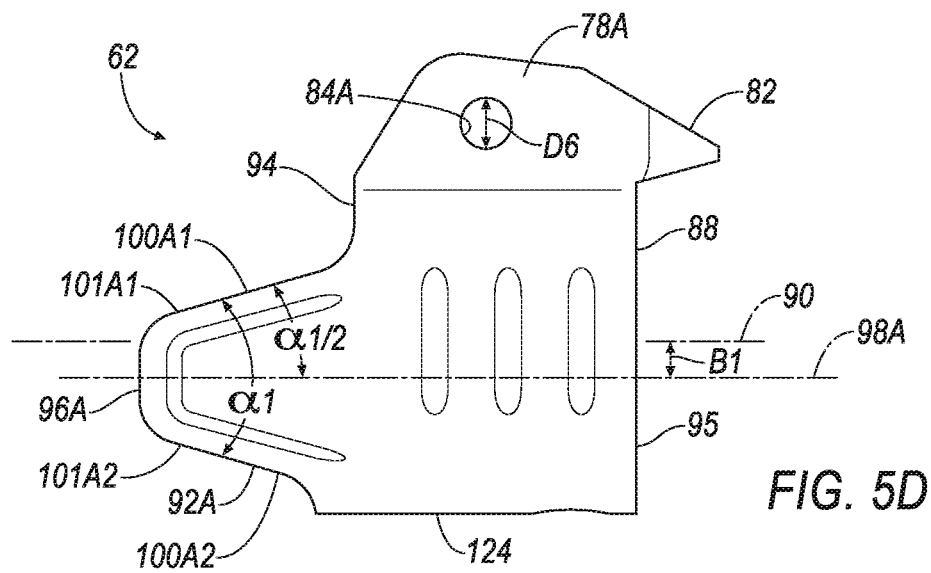
FIG. 5D is a right-side view of the collar of FIG. 5A.
Figure 5E:
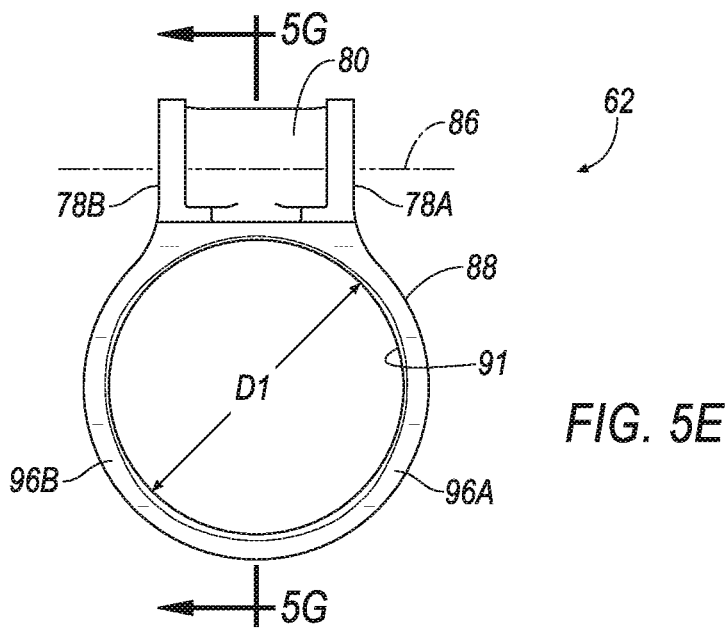
FIG. 5E is a front view of the collar of FIG. 5A.
Figure 5F:
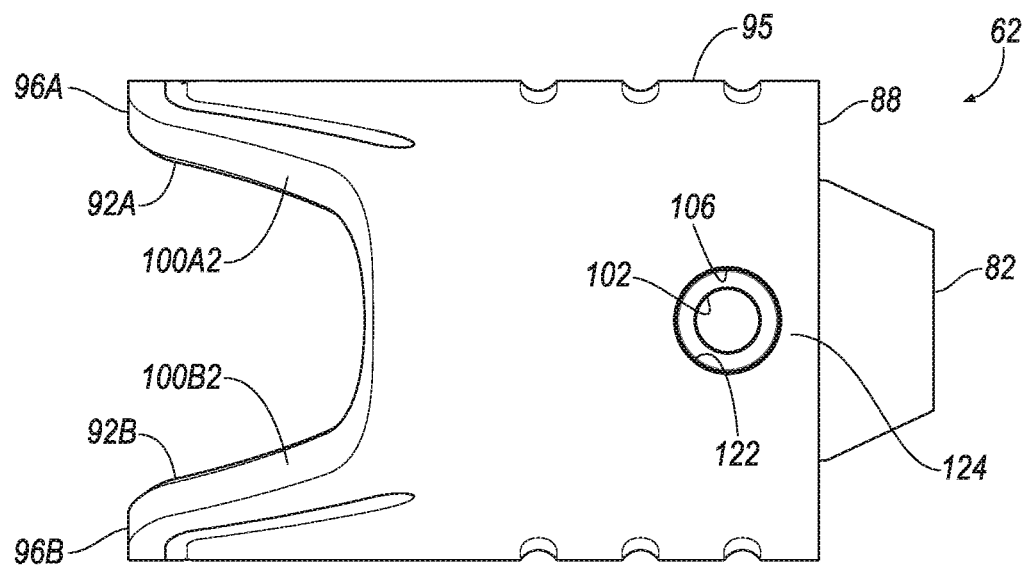
FIG. 5F is a bottom top view of the collar of FIG. 5A.

An example first positioning tab 92A, i.e., a first collar tab 92A, and an example second positioning tab 92B, i.e., a second collar tab 92B, have an axial length L1 extending from a distal edge 94 of a main, i.e., annular portion 95, of the collar 88, to a tip 96A, 96B of each of the tabs 92A, 92B in a direction parallel to the mounting axis 90. An example nominal value of L1 may be approximately 15 mm (0.60 inches). The tabs 92A, 92B may each have a substantially trapezoidal shape when the collar 88 is viewed from the side. The tabs 92A, 92B, when viewed from the distal end of the collar 88, as in FIG. 5E, are arcuately shaped, aligned with and defining in part diameter D1 of the collar 88.

The tabs 92A, 92B may each be substantially symmetrical about a centerline 98A, 98B, respectively, of tabs 92A and 92B. For example, the first tab 92A may have example tapered sides, e.g., a first, i.e., an upper wedge side 100A1 and a second, i.e., a lower wedge side 100A2, separated by a tab wedge angle of α1, and each of wedge sides 100A1 and 100A2 being separated from the centerline 98A by an angle of α1/2. An example nominal value of α1 may be approximately 32°, with α1/2 being approximately 16°. Both wedge sides 100A1 and 100A2 are thus angled with respect to centerline 98A. The distance of the tip from the distal edge 94 to the tip 96A, i.e., the axial length of the tab 92A, as noted above, is length L1. The tabs 92A, 92B may maintain the inside diameter D1 for their length.

Figure 5G:
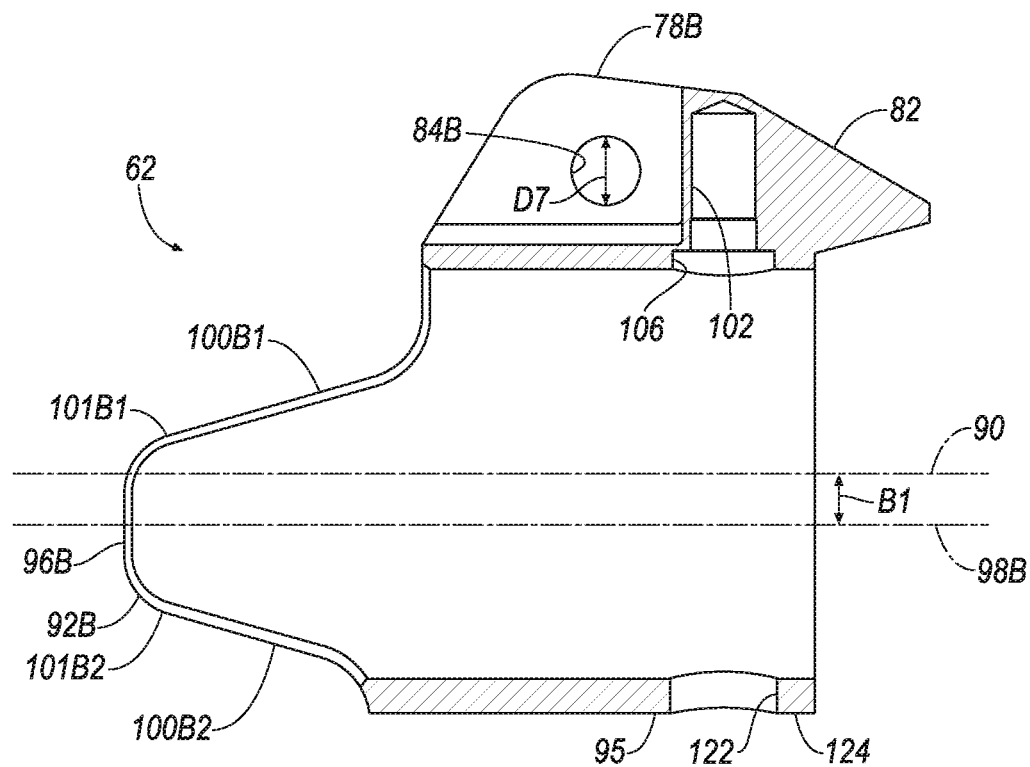
FIG. 5G is a sectional view of the collar of FIG. 5A taken in the direction of arrows 5G of FIG. 5E.

The second tab 92B may be similarly formed and positioned on the collar 88 and include upper and lower wedge sides 100B1 and 100B2 respectively. Both of the centerlines 98A, 98B may be located a distance B1 below and parallel to the mounting axis 90, as best shown in FIG. 5D and FIG. 5G. An example nominal value of B1 may be approximately 2.5 mm (0.10 inches). The wedge sides 100A1, 100A2, 100B1, 100B2 are angled in that each is disposed at an angle to the mounting axis 90.

The tabs 92A, 92B may also define in part a nominal tab contact point 101A1, 101A2, 101B1, 101B2, one on each of wedge sides 100A1, 100A2, 100B1, 100B2. The role of the nominal tab contact points 101A1, 101A2, 101B1, 101B2 will be explained in more detail below.

Figure 7:
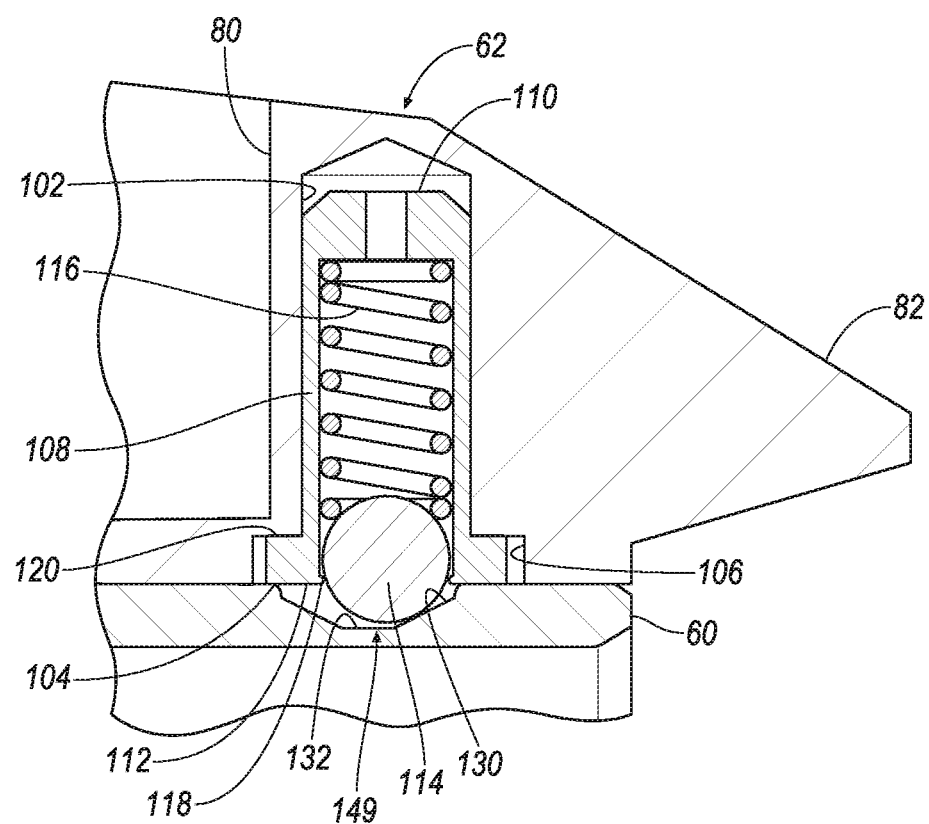
FIG. 7 is a sectional view of the lever and housing of FIG. 1, taken through plane 7 in the direction of arrow 7A.

The mounting base 62 may further include a plunger receiving aperture 102 for receipt of an example spring-loaded ball base detent plunger 104, i.e., a collar detent plunger 104, best shown in FIG. 7, that comprises part of the alignment interface 72. The receiving aperture 102 may include a counterbore 106.

The detent plunger 104 may be commercially purchased. The following description of the detent plunger 104 is exemplary and may be applicable to later-referenced ball plungers. The example plunger 104 may include a substantially constant diameter sleeve 108 formed of steel with a closed end 110 and an open end 112. The closed end 110 may include a vent aperture. A durable plunger ball 114 (e.g., steel, ceramic) may disposed in the sleeve 108 to extend, i.e., project, from the open end 112, with a compression coil plunger spring 116 disposed in the sleeve 108 between the ball 114 and the closed end 110. The open end 112 may be formed to both provide an inner lip 118 that traps the ball 114 and the spring 116 therein, and provide an outer lip 120 thereat. The outer lip 120 may be used to limit travel of the sleeve 108 into the receiving aperture 102. The counterbore 106 may be of a depth and diameter to accommodate the outer lip 120, allowing the plunger 104 to be substantially flush with the mounting surface 91 of the collar 88, but with the ball 114 being able to extend beyond the mounting surface 91 and past the inside diameter D1 of the collar 88. While the plunger 104 has been described as including a sleeve, a coil spring and a ball, the structure described is merely exemplary and alternative plungers may be employed. For example, the plunger may employ a bullet-shaped plunger projectile in place of the ball-shaped plunger projectile. Or a double-ended cylinder, being radiused at one or both ends, may be employed in place of the ball. Alternatively, the plunger may use a spring type other than a coil spring, e.g., a leaf spring, to displace the projectile. Yet alternatively, the plunger may principally comprise an arcuate leaf spring serving as both a spring and a projectile that is received by a recess when aligned therewith. The arcuate leaf spring may be bowed or cantilevered. The plunger may yet alternatively comprise a dome spring in lieu of a separate spring and projectile. The dome spring may be in the form of a resilient thin walled partial hemisphere that may resiliently and substantially elastically deflect at an apex in a compressed condition, inverting an apex portion of the dome, and self-restoring to its partial hemispherical shape, i.e., dome shape, when disposed over a detent notch. A plunger yet alternatively may rely on magnetic or electromagnet properties of components to bias a projectile in a desired direction and into engagement with a detent notch.

An access hole 122 may be formed in a bottom 124 of the collar 88, opposite of and in alignment with the receiving aperture 102 and the counterbore 106, to facilitate forming the receiving aperture 102 and the counterbore 106, and the receipt and installation of the detent plunger 104 in the aperture 102. The plunger 104 is retained in the receiving aperture 102 by an interference fit, i.e., a press fit, relationship therebetween. A portion of the receiving aperture 102 may be larger than an outside diameter of the plunger 104 to facilitate an aligned receipt of the plunger 104 by the receiving aperture 102. The access hole 122 may be provided with a chamfer (not shown) to facilitate passage of the plunger 104 therethrough. The plunger 104 is shown in the aperture 102 in FIG. 7.

The alignment interface 72 may include the collar 88, including the annular portion 95 and the tabs 92A, 92B and the plunger 104 and complementary features on the handpiece housing 58, best shown in FIGS. 6A-6D. Such complementary features may include a first tab receiving channel 128A and a second tab receiving channel 128B for receipt, respectively, of the first tab 92A and the second tab 92B, and a biasing surface 130 provide by a detent notch 132 defining the biasing surface 130 for engagement by the plunger 104. The tab receiving channels 128A, 128B are positioned on the housing 58 for alignment with and receipt of the collar tabs 92A, 92B.

The handpiece housing 58 includes both a grip surface 134 and a relatively recessed engaging surface 136. The recessed engaging surface 136 is disposed proximal to the grip surface 134. A peripheral wall 138 defines a border between and connects the two surfaces 134 and 136. The grip surface 134 may have a first surface diameter D2. An example nominal value of D2 may be approximately 22 mm (0.90 inches). The engaging surface 136 may have a smaller second surface diameter D3. An example nominal value of D3 may be approximately 20 mm (0.80 inches). Both diameters D2 and D3 may be centered on a housing axis 140 along which the housing 58 extends. An example height H1 of peripheral wall 138, given the example values of D2 and D3, may be approximately 1 mm (0.04 inches).

Diameter D3 of the engaging surface 136 is smaller than the inside diameter D1 of the collar 88, the surface 136 and the collar 88 thereby sized to allow a slideable disposition of the collar 88 over the proximal end of the housing 58 of the handpiece 54 when the housing axis 140 is substantially aligned with the mounting axis 90. When the handswitch 52 is coupled to the housing 58, the housing axis 140 may be coincident with the mounting axis 90. As illustrated in FIG. 5C, the mounting axis 90 is normal to a direction of the pivot axis 86. The housing axis 140 may accordingly also be normal to the direction of the pivot axis 86 when the handswitch 52 is coupled to the housing 58. The peripheral wall 138 may extend radially outwardly relative to the mounting axis 90, connecting the engaging surface 136 with the grip surface 134. The peripheral wall 138 may define the first tab receiving channel 128A, i.e., the first channel 128A and the second tab receiving channel 128B, i.e., the second channel 128B.

The first channel 128A may have an axial length L2. More specifically, a channel terminus 142A analogous to the tip 96A is spaced the length L2 from a proximal edge 144 of the peripheral wall 138. The second channel 128B may likewise have a length L2, and a channel terminus 142B analogous to the tip 96B is spaced the length L2 from the proximal edge 144 of the peripheral wall 138. An example nominal value of L2 may be approximately 15 mm (0.60 inches). The axial length L2 of the channels 128A, 128B may be substantially equal to the axial length L1 of the tabs 92A, 92B. The first channel 128A has upper and lower wedge sides 146A1, 146A2. The second channel 128B has corresponding upper and lower wedge sides 146B1, 146B2. The upper and lower wedge sides of both channels have an included angle α2 therebetween. The angle α2 may be substantially equal to the angle α1. An example nominal value of α2 may be approximately 34°.

Figure 6A:
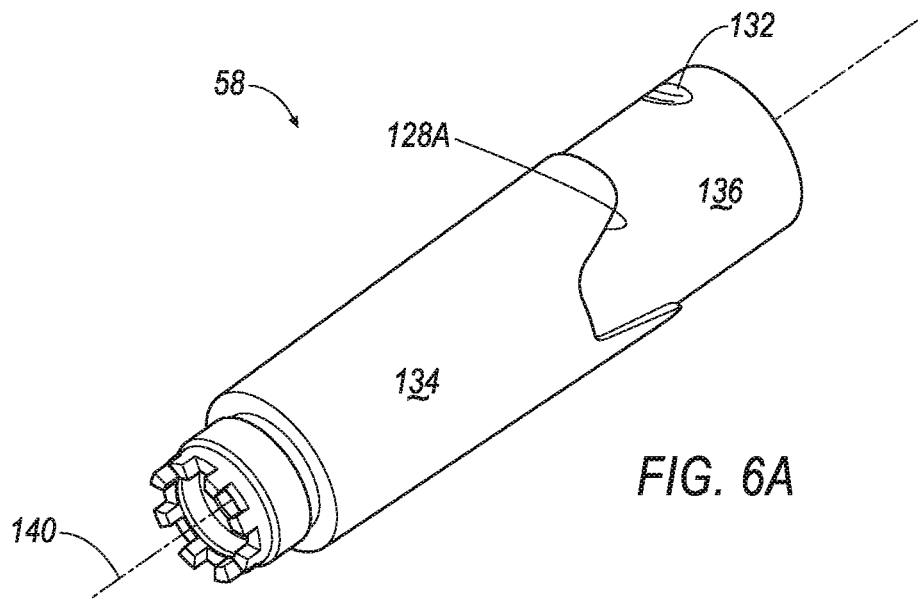
FIG. 6A is a perspective view of a handpiece housing of FIG. 2.
Figure 6B:
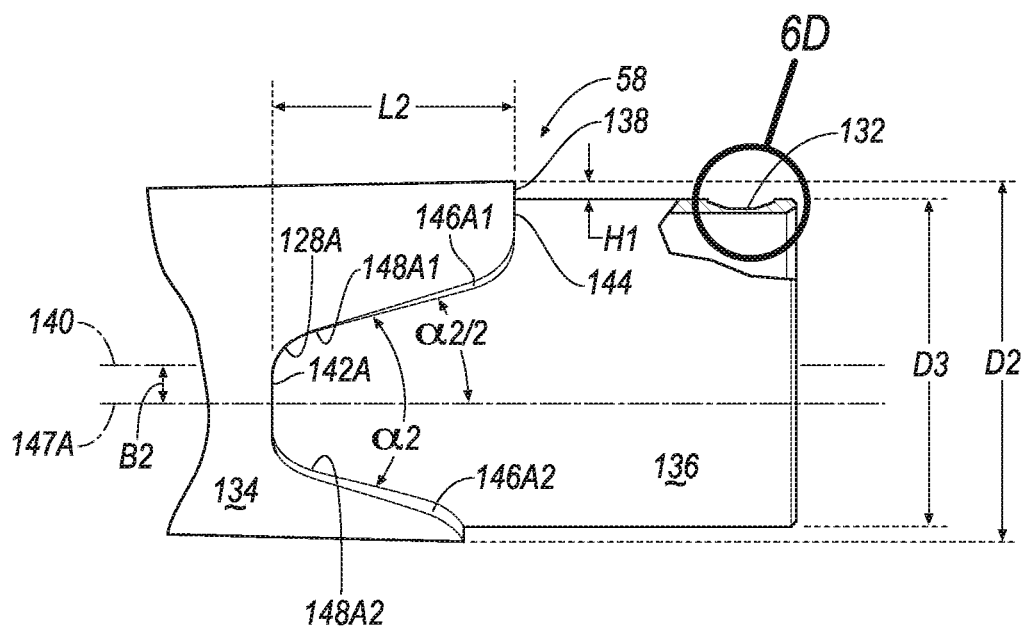
FIG. 6B is a right-side view of a part of the handpiece housing of FIG. 6A.
Figure 6C:
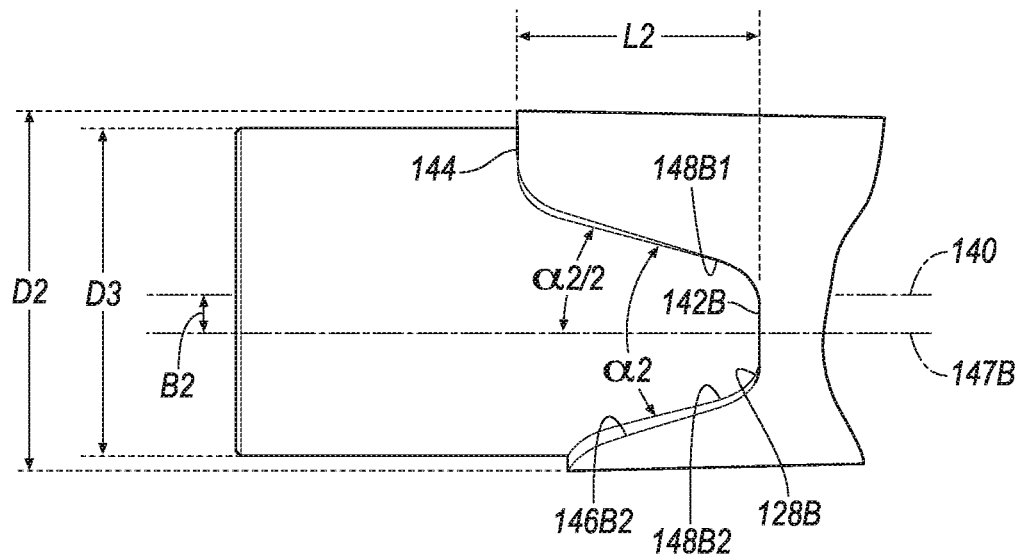
FIG. 6C is a left-side view of a part of the handpiece housing of FIG. 6A.
Figure 6D:
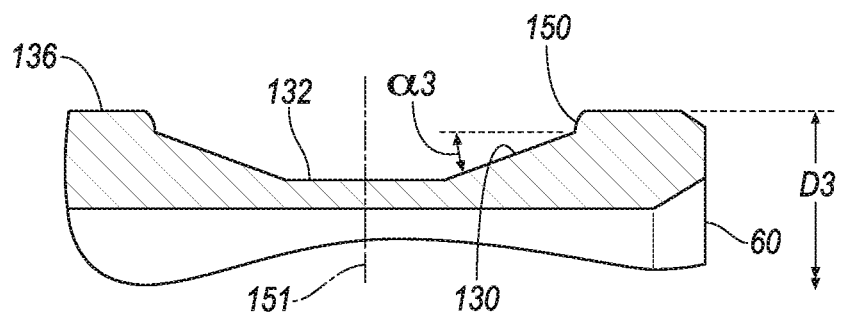
FIG. 6D is an enlarged sectional view of a portion of the housing in circle 6D of FIG. 6B.

The channel 128A may be substantially symmetrical about a channel centerline 147A of the tab receiving channel 128A. For example, the first channel 128A may have each of the upper wedge side 146A1 and the lower wedge side 146A2 separated from the centerline 147A by an angle of α2/2. Likewise, the second channel 128B may have its upper wedge side 146B1 and its lower wedge side 146B2 separated from its channel centerline 147B by an angle of α2/2. As noted above, an example nominal value of α2 may be 34°, with α2/2 being approximately 17°. The wedge sides 146A1 and 146A2 are thus angled with respect to centerline 147A, and the wedge sides 146B1 and 146B2 thus angled with respect to centerline 147B. The channel centerlines 147A may be located a distance B2 below the mounting axis 90, as best shown in FIG. 6B and FIG. 6C. The value of B2 may be substantially equal to the value of B1, with an example nominal value of B2 being approximately 2.5 mm (0.10 inches).

The channel wedge sides 146A1 and 146A2, together with the tab wedge sides 100A1, 100A2 define nominal channel contact points 148A1, 148A2 on the channel wedge sides 146A1, 146A2 and define the tab contact points 101A1 and 101A2 on the tab wedge sides 100A1, 100A2. In an engaged position of the handswitch 52 on the housing 58, the wedge sides 100A1, 100A2 respectively engage the channel wedge sides 146A1, 146A2 at the channel contact points 148A1, 148A2 that are in contact with the tab contact points 101A1, 101A2. Channel contact points 148B1, 148B2 on the wedge sides 146B1, 146B2 of the second channel 128B are similarly defined by engagement of the wedge sides 146B1, 146B2 with the tab contact points 101B1, 101B2 of the second tab 92B. Such engagement occurs either before the tips 96A, 96B engage the terminus 142A of the first channel 128A or the terminus 142B of the second channel 128B, and before the proximal edge 144 engages the distal edge 94 of the collar 88.

The housing 58 may have a diamond-like carbon ("DLC") coating. DLC coating may beneficially provide coated surfaces with wear resistance and a lower coefficient of friction.

The collar detent plunger 104 and the detent notch 132 cooperatively define a mounting base detent 149. The detent 149 may serve to retain the handswitch 52 on the housing 58, and to bias the tab wedge sides 100A1, 100A2, 100B1, 100B2 against the first channel wedge sides 146A1, 146A2 and the second channel wedge sides 146B1, 146B2. The detent notch 132 may be formed as a recess in the engaging surface 136 and may be symmetrical about a notch centerline 151. The notch 132 is not required to be symmetrical but may be so if it is formed with a rotating tool, e.g., a mill. The biasing surface 130 of notch 132 is positioned at an engagement angle 3 relative to the mounting axis 90. An example nominal value of 3 with respect to the housing axis 140 may be approximately 19°. With the mounting base 62 installed on the housing 58, the plunger's ball 114 is received in part by the notch 132 as shown in FIG. 7. Deflection of the plunger spring 116 within the sleeve 108 and against the ball 114 presses the ball 114 against the biasing surface 130, in turn pressing the tab wedge sides 100A1, 100A2, 100B1, 100B2 into engagement with the first channel wedge sides 146A1, 146A2 and the second channel wedge sides 146B1, 146B2 at the respective contact points.

The biasing surface 130 is at a proximal end of the detent notch 132 that is engaged by the plunger 104. The notch may also include a retention edge 150 that may be 90 degrees to the housing axis 140, or may be radiused, or at an angle greater than the angle α3 and less than 90 degrees. The retention edge 150 may beneficially increase an axial force needed to remove the handswitch 52 from the housing 58. The edge 150 forces the ball 114 to be suddenly displaced against the plunger spring 116. The increase in displacement results in an increase in force against the ball 114, which translates to an increase in force in the axial direction, i.e., in a direction parallel to the housing axis 140, resisting what may be an unintended removal of the handswitch 52 from the housing 58.

The tabs 92A, 92B and the channels 128A, 128B facilitate proper alignment of the handswitch 52 with the housing 58, in turn facilitating installation of the handswitch 52 on the housing 58. The combination of the detent 149, the tabs 92A, 92B and the channels 128A, 128B allows the handswitch 52 to be properly aligned with the housing 58 for installation of the handswitch 52 thereon, and for retention of the handswitch 52 on the housing 58 prior to connecting the connector 56 to the housing 58. An example force required to overcome the detent 149 to remove the handswitch 52 from the housing 58 may be in a range of 27 to 36 Newtons (6 to 8 pounds) of force.

Figure 8A:
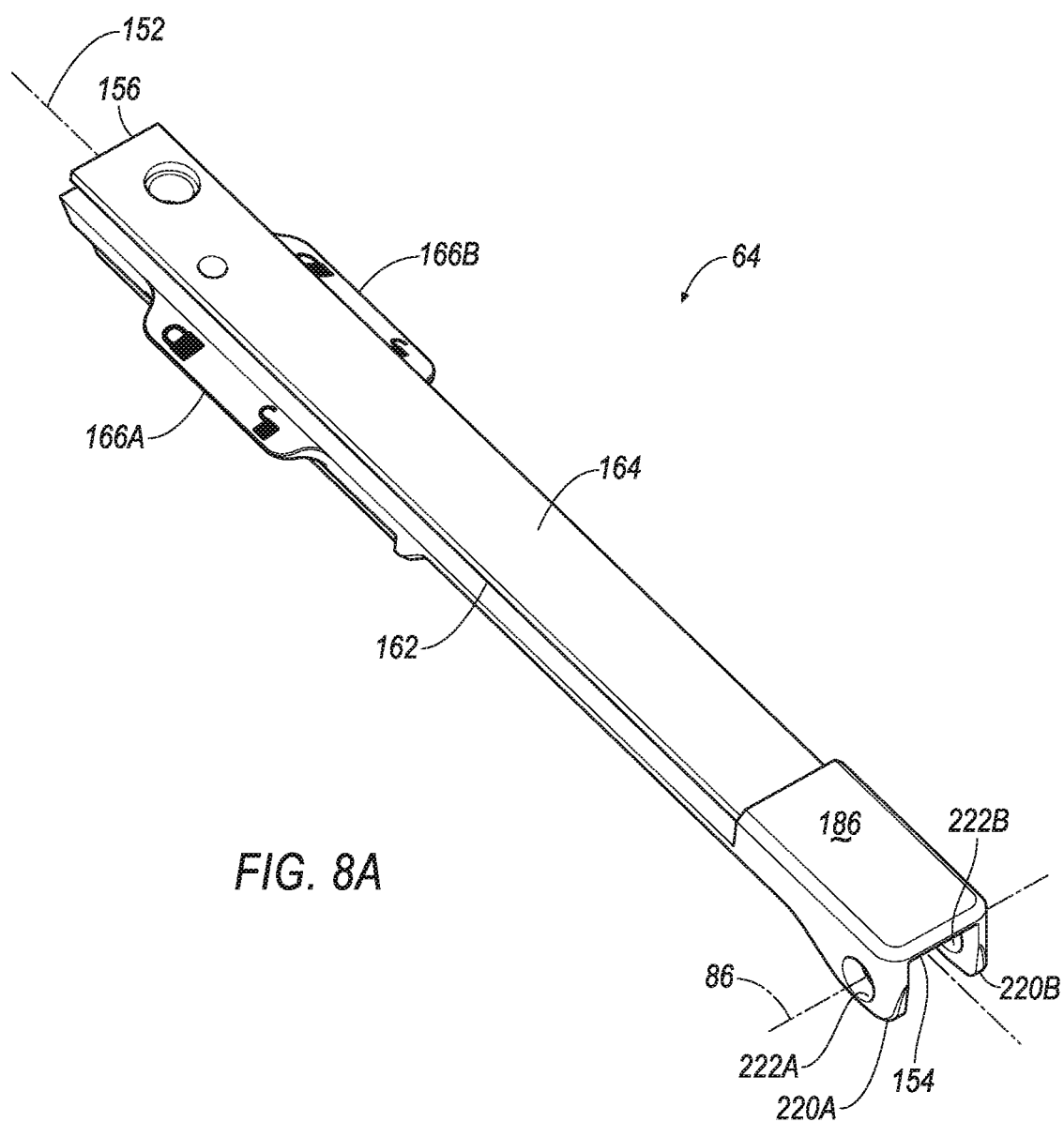
FIG. 8A is a perspective view of a lever of the handswitch of FIG. 4.

The elongated lever 64, as stated above, is pivotably connected to the mounting base 62. The lever 64 defines a lever axis 152 substantially normal to at least the direction of the pivot axis 86 as best shown in FIG. 8C. The lever 64 includes a proximal end 154 pivotably connected to the mounting base 62 at the pivot axis 86 and a distal end 156 opposite the proximal end 154. A pivot pin 155, centered on the pivot axis 86, may be used to pivotably connect the lever 64 to the base 62. The lever 64 may have an example nominal overall length L3 from the distal end 156 to the proximal end 154 of approximately 92 mm (3.6 inches). A first track 158, i.e., a switch track, is on an inner side 160 of the lever. The inner side 160 of the lever 64 may substantially face the housing axis 140 when installed on a handpiece housing 58. A second track 162, i.e., an extension track, is on an outer side 164 opposite the inner side 160 of the lever 64, with both tracks 158, 162 substantially parallel to the lever axis 152. The first track 158 is always located to be, in an installed position, closer to the lever axis 152 than the second track 162.

The lever 64 may have a width W1 between opposed first and second lateral sides 165A, 165B. An example value of the width W1 may be approximately 10 mm (0.40 inches). The lateral sides 165A, 165B are disposed between and connect the inner side 160 and the outer sides 164. The lever 64 is biased about the pivot axis 86 about the pivot axis 86 relative to the base 62 by the spring 66. The run-safe switch 68 is slidably disposed on the first track 158. The lever extension 70 is slidably disposed on the second track 162. The lever 64, like the housing 58, may be provided with a DLC coating.

The lever 64, presenting its outer side 164 and the second track 162 in FIG. 8B, has opposed first and second position indicator wings 166A, 166B, respectively, near the distal end 156. The wings 166A, 166B are positioned for alignment with an indicator line 168 on the switch 68, as described in more detail below. The wings 166A, 166B may be labeled with icons 167A, 167B indicative of describing the associated switch position. For example, a locked icon 167A in the form of a schematic representation of a locked, i.e., closed, padlock may indicate a safe, i.e., non-running condition, and an icon 167B in the form of a schematic representation of an unlocked, i.e., open, padlock may indicate a run condition. Other markings may be used in place of the padlock icons 167A and 167B. For example, the words "RUN" and "SAFE" may be employed as icons. The unlocked icon 167B may be placed closer to the pivot axis 86 than the locked icon 167A.

An extension plunger aperture 170, for receipt of a lever extension detent plunger 172, i.e., an extension plunger 172, may be formed in the lever 64 on the outer side 164. The plunger 172 may comprise part of a lever extension multi-position detent. The extension plunger 172 may be spring-loaded, and may be formed like the switch plunger 198.

A pin aperture 176 for an extension travel limit pin 178, shown in FIGS. 8B and 8C, may be disposed proximate to the distal end 156, maximizing the extension of the extension 70 relative to the lever 64. The pin aperture 176 may extend through the lever 64. A proximal end portion 180 may extend a distance L4 from the lever's proximal end 154 to an end wall 182 of the proximal end portion 180. An example value of distance, i.e., length, L4 may be approximately 18 mm (0.70 inches). The proximal end portion 180 may accommodate a hinge pocket 184 therebeneath, best shown in FIG. 8C and FIG. 8E, and may further define a flush outer surface 186 of the proximal end portion 180 that aligns with an outer surface, i.e., a contact surface, 188 of the lever extension 70 when the extension 70 is installed on the lever 64. The end wall 182 may define a distal end of the flush outer surface 186.

Figure 8D:
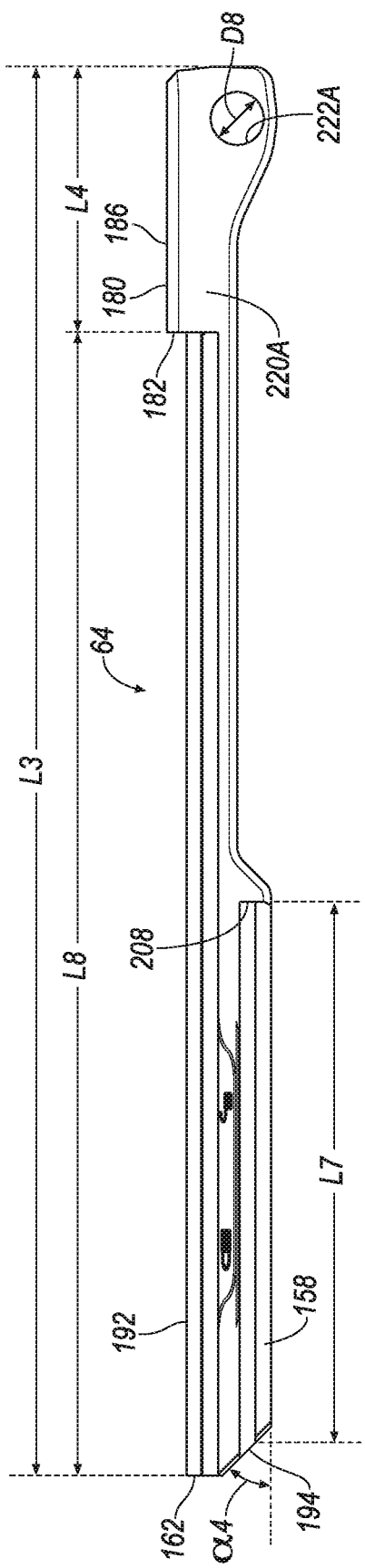
FIG. 8D is a right-side view of the lever of FIG. 8A.
Figure 8E:
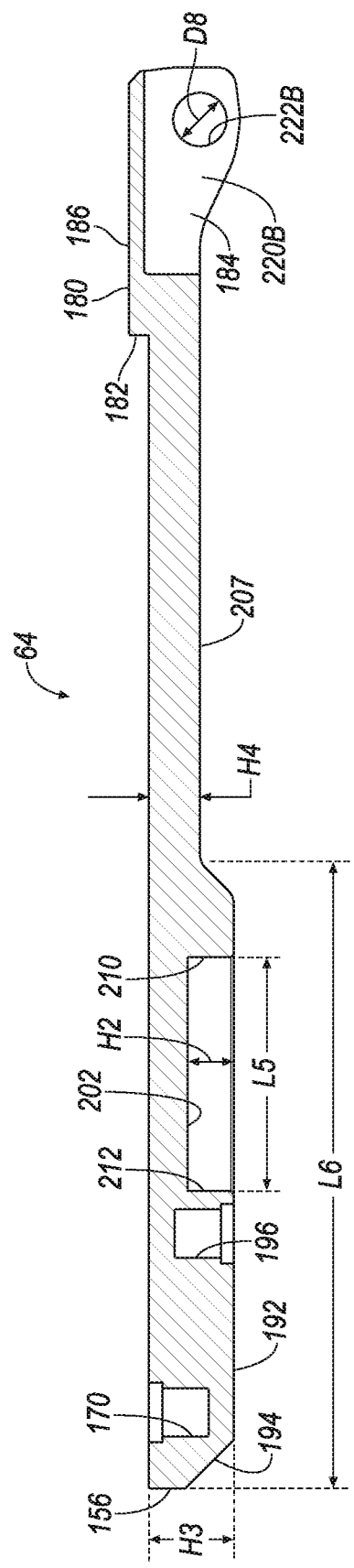
FIG. 8E is a sectional view of the lever of FIG. 8A taken in the direction of arrows 8E of FIG. 8B.

In FIG. 8C, the lever 64 presents its inner side 160 and the first track 158. An unlabeled side of the wings 166A, 166B is shown. At the proximal end 154, the hinge pocket 184 can be seen. In a distal end portion 192, at the distal end 156, a tapered end surface 194 is provided. The end surface 194, when viewed from the side, as shown in FIGS. 8D and 8E, may run in a downward, proximal direction at an angle α4. The angle α4 may be approximately 45°. A switch plunger aperture 196, for receipt of a switch detent plunger 198, i.e., a run-safe switch plunger 198 or yet alternatively named a switch plunger 198, may be formed in the lever 64 on the inner side 160. The switch plunger 198 may comprise part of a multi-position switch detent and may be spring-loaded, and may be formed like the collar detent plunger 104. The switch plunger 198 may be shorter than the collar detent plunger 104.

The aperture 176 for the extension travel limit pin 178 is also shown, with the through aperture 176 facilitating installation of the pin 178. The aperture 176 may alternatively be a blind hole, not extending all of the way through the lever 64 to the inner side 160.

Figure 4:
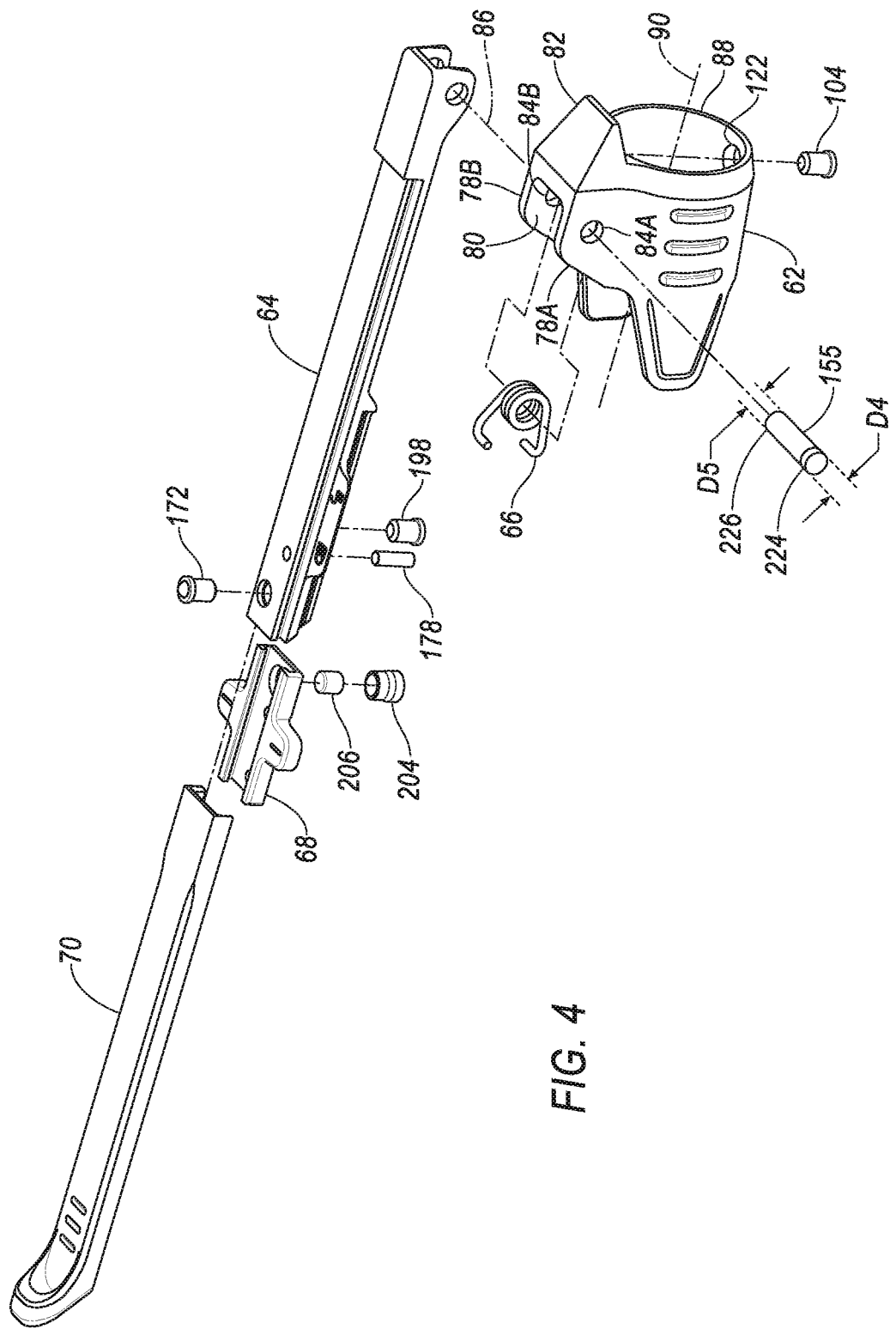
FIG. 4 is an exploded view of the handswitch of FIG. 2.

The inner side 160 of the distal end portion 192 also may include a switch travel slot 202 that receives a magnet retainer, i.e., a magnet housing 204 which in turn receives a switch magnet 206, both of which are incorporated into the switch 68 and extend upwardly therefrom. An example length L5 of the slot 202 may be approximately 15 mm (0.60 inches). An example width W2 of the slot 202 may be approximately 5 mm (0.20 inches). An example depth H2 of the slot 202 may be approximately 3 mm (0.12 inches). The switch 68, the switch magnet 206, and the magnet housing 204 are shown in FIG. 4. A travel range of the switch 68 relative to the lever 64 may be defined by the length L5 of the slot 202.

The side view of FIG. 8D and the sectional side view of FIG. 8E show that the distal end portion 192 of the lever 64 may have a distal end portion thickness H3, greater than a center portion thickness H4 of a center portion 207 of the lever 64. An example value of the distal end portion 192 thickness H3 may be approximately 5 mm (0.20 inches), and of the center portion thickness H4 may be approximately 3 mm (0.12 inches). The distal end portion 192, as indicated by the thickness H3, may extend a length L6 in a proximal direction from the distal end 156 of the lever 64. An example nominal value of L6 may be approximately 40 mm (1.6 inches).

Figure 8F:
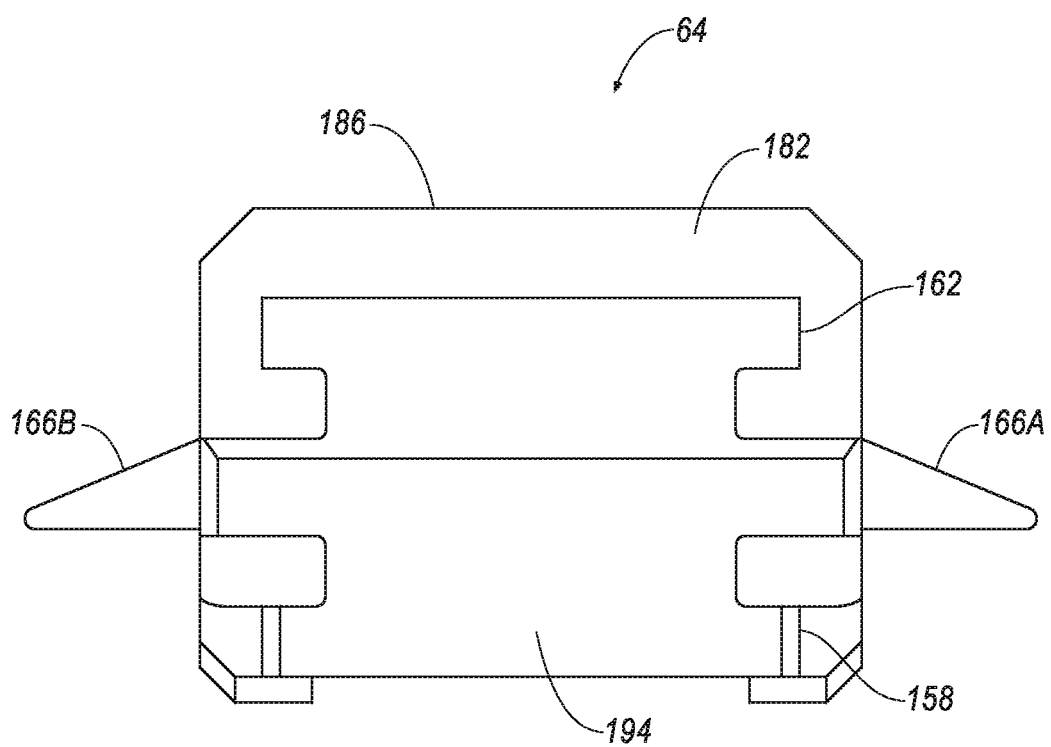
FIG. 8F is a front view of the lever of FIG. 8A.
Figure 9A:
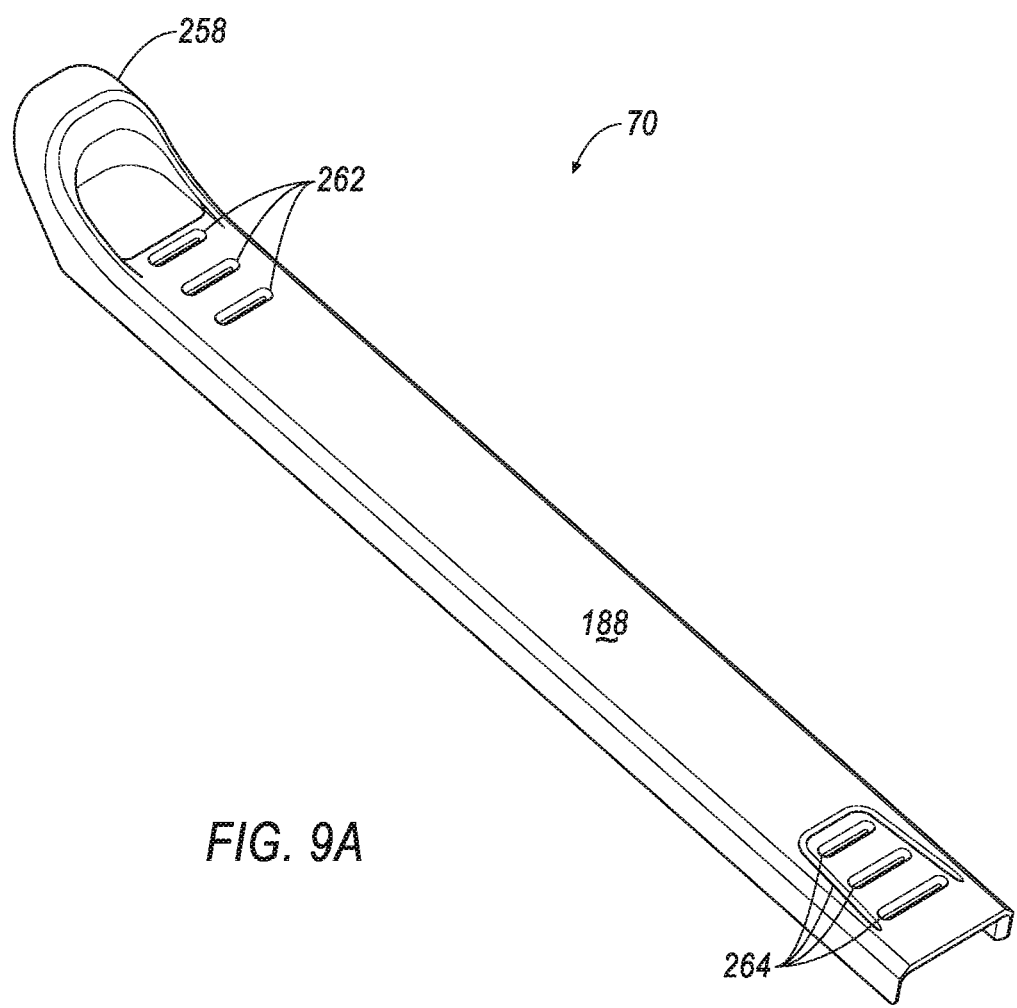
FIG. 9A is a perspective view of a lever extension of the handswitch of FIG. 4.
Figure 9F:
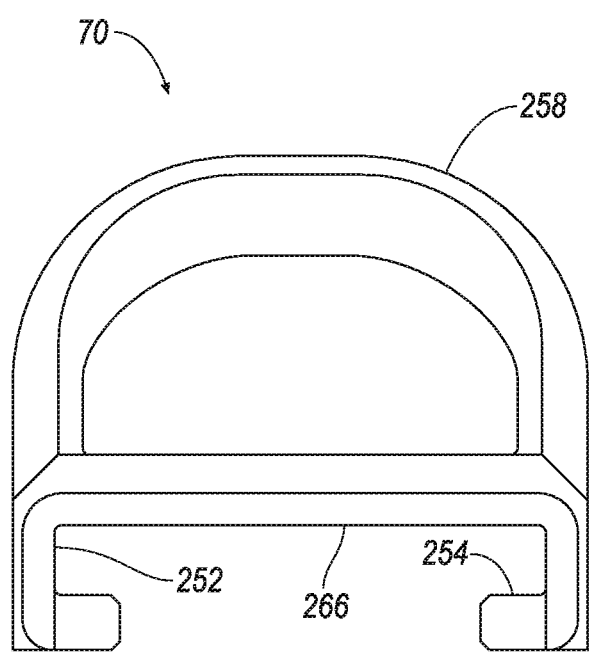
FIG. 9F is a rear view of the lever extension of FIG. 9A.
Figure 10A:
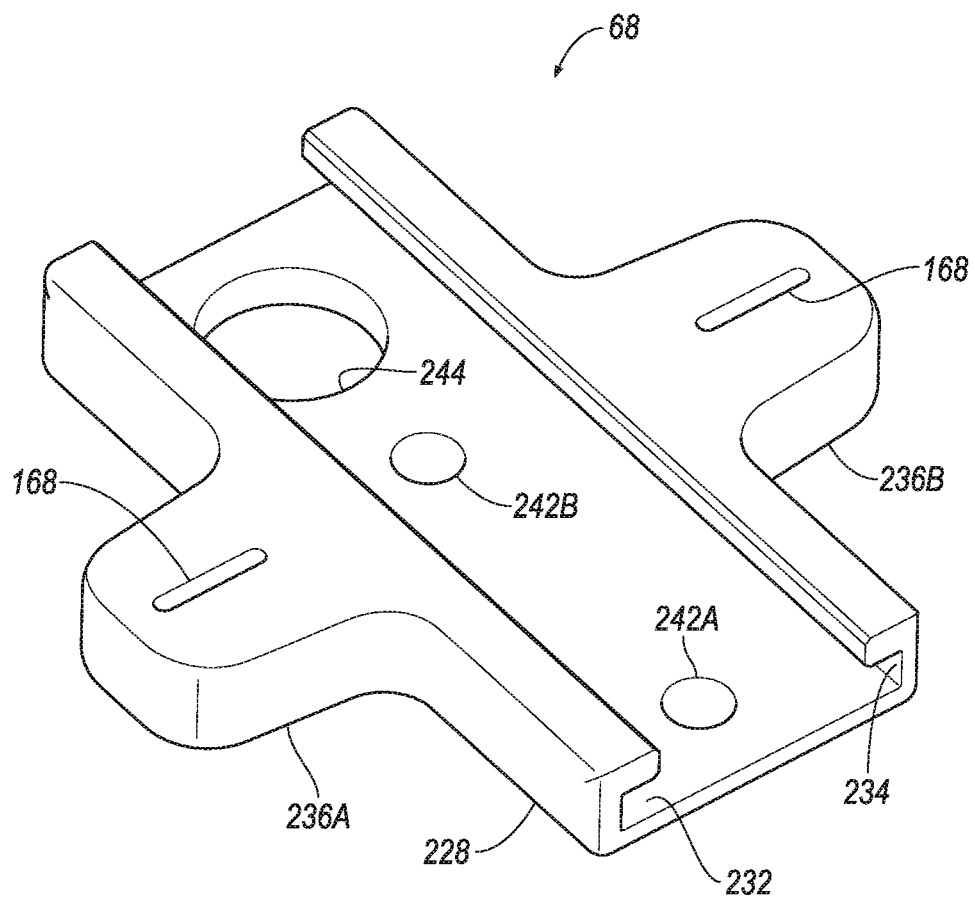
FIG. 10A is a perspective view of a switch of the handswitch of FIG. 4.
Figure 10B:
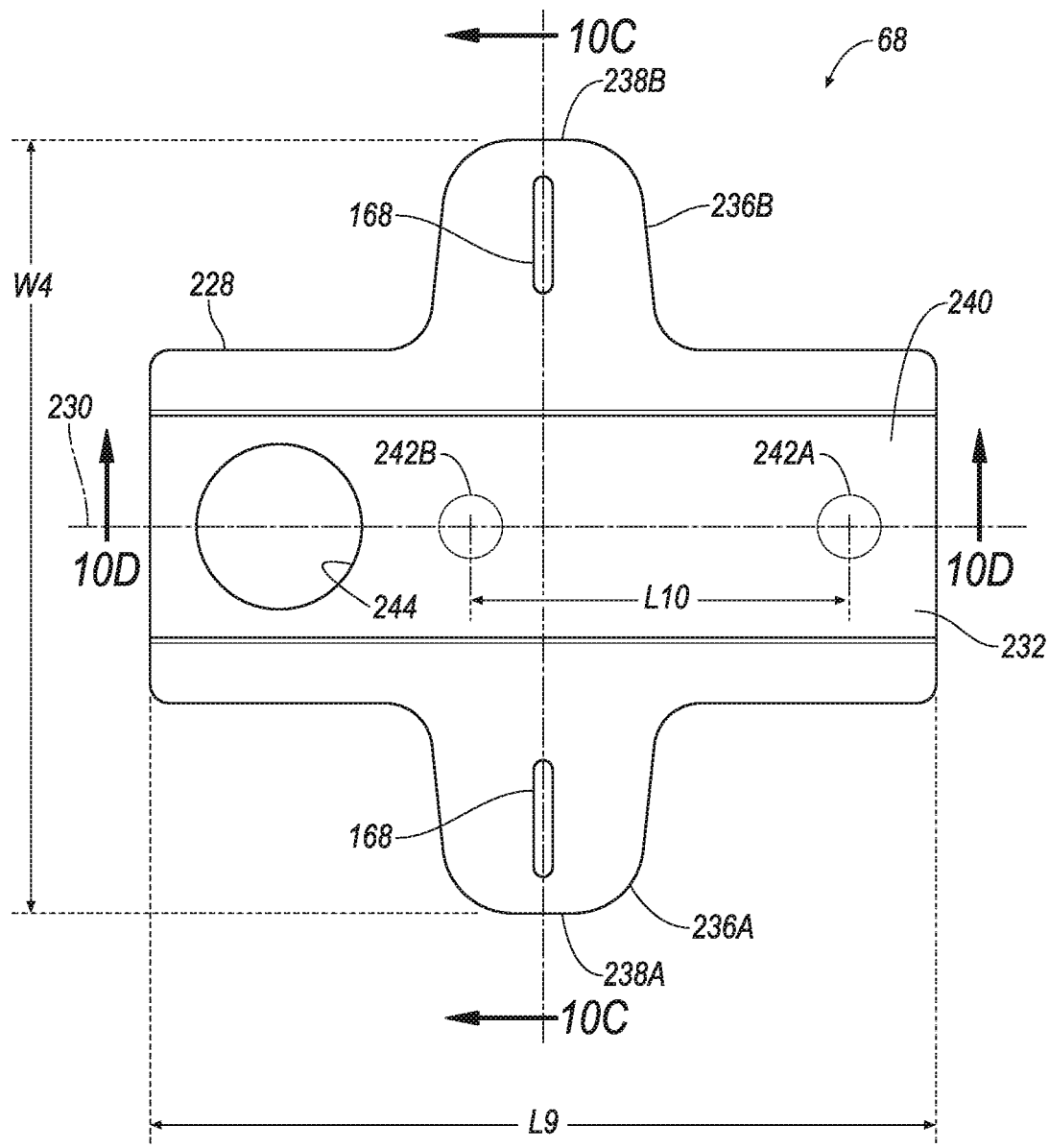
FIG. 10B is a top view of the switch of FIG. 10A.
Figure 10C:
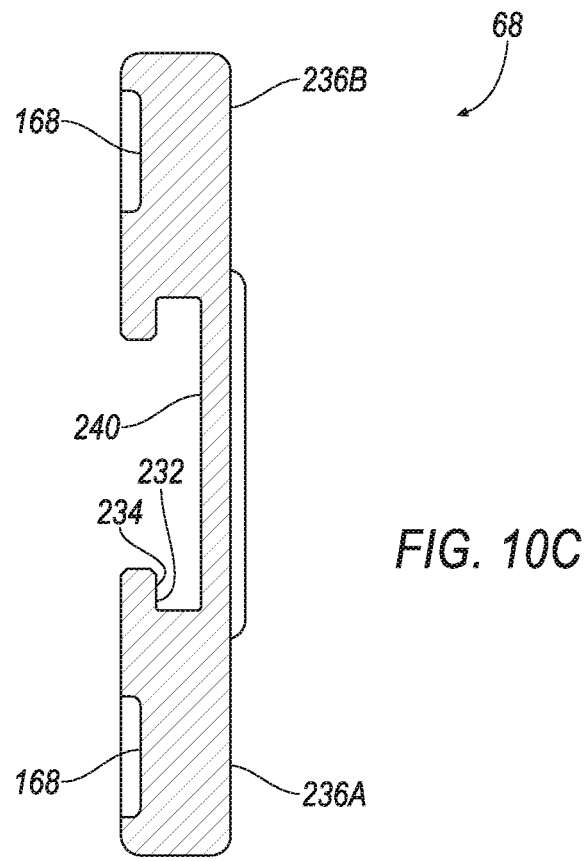
FIG. 10C is a sectional view of the switch of FIG. 10A taken in the direction of the arrows 10C of FIG. 10B.
Figure 10D:
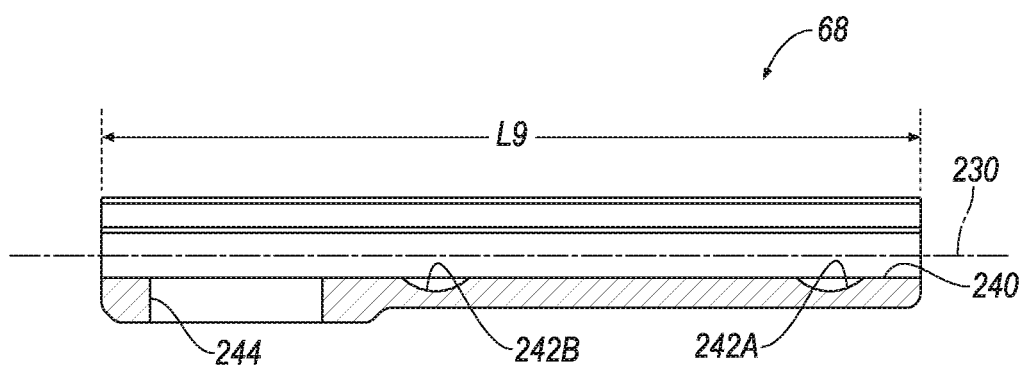
FIG. 10D is a sectional view of the switch of FIG. 10A taken in the direction of the arrows 10D of FIG. 10B.

Both of the tracks 158 and 162 can both be seen in FIGS. 8D and 8F, and the second track 162 can be seen in FIG. 8B and the first track 158 can be seen in FIG. 8C.

The first track 158, i.e., the switch track 158, can be seen in each of FIGS. 8D and 8F. The first track 158 is included in the distal end portion 192 on the inner side 160. The first track 158 may be in the shape of a T-shaped track, i.e., a T-track. Alternatively, the track 158 may have a different profile, presenting, for example, a dovetail, a T-slot, a rectangular, or a circular track or slot, or any other appropriate shape. A length L7 of the first track 158, an example length being approximately 38 mm (1.5 inches), may be shorter than the length L6 of the distal end portion 192 with a track end 208 that may serve as a switch travel stop for the run-safe switch 68 in an unlocked position, i.e., a run or an active position. Alternatively, the switch travel stop for the run-safe switch 68 in the unlocked position may be provided by a proximal end 210 of the slot 202, with travel of the switch 68 relative to the lever 64 terminating when the magnet housing 204 engages the proximal end 210 of the slot 202. Similarly, a switch travel stop for a locked position, i.e., a safe or an inactive position, of the switch 68 may be provided by a distal end 212 of the slot 202, with travel of the switch 68 relative to the lever 64 terminating when the magnet housing 204 engages the distal end 212 of the slot 202.

The second track 162, i.e., the extension track 162, can be seen in each of FIGS. 8B, 8D and 8F. The second track 162 may extend a length L8, from the lever's distal end 156 to the end wall 182 of the proximal end portion 180 on the outer side 164. An example value of length L8 may be approximately 75 mm (3.0 inches). The second track 162 may also be in the shape of a T-shaped track, i.e., a T-track. Like the first track 158, the second track 162 may alternatively have a different profile, presenting, for example, a dovetail, a T-slot, or circular track or slot, or any other appropriate shape. The end wall 182 may serve as a travel stop for the extension 70 in a stored position. Alternatively, the extension travel stop for the stored position may be provided by a distal end 214 of a pin slot 216 in the extension 70. Accordingly, travel of the extension 70 to the stored position may be terminated by either engagement of a proximal end 218 of the extension 70 with the end wall 182, or by engagement of the distal end 214 of the pin slot 216 by the extension travel limit pin 178. Similarly, an extension travel stop for the extension 70 in a fully extended position may be provided by a proximal end 218 of the slot 216, with travel of the extension 70 relative to the lever 64 terminating when the extension travel limit pin 178 engages the proximal end 218 of the slot 216. Alternatively, the pin 178 may be placed in the extension 70 and the slot 216 in the lever 64.

The hinge pocket 184 includes opposed first and second side members 220A, 220B each with an aligned, co-axial first and second aperture 222A, 222B respectively defining or at least aligned with the pivot axis 86 when assembled to the base 62. Alternatively, the proximal end portion 180 may be formed as a solid mass without the pocket 184, and with a single aperture passing therethrough on the pivot axis 86. The apertures 222A, 222B may have either a clearance fit or a press fit relationship with regard to the pivot pin 155. The pin 155 may have a first diameter D4 on a first end 224 and a second diameter D5 on a second end 226, with the first diameter D4 being greater than the second diameter D5. Example nominal values of diameters D4 and D5 may be approximately 3.6 mm (0.14 inches) and approximately 3.5 mm (0.13 inches) respectively. The aperture 84A of the ear 78A of the mounting base 62 may have a diameter D6, an example value of D6 being equal to or smaller than the diameter D4 of the first end 224 of the pin 155, the difference, if any, selected to yield a press fit between the first end 224 of the pin 155, and the first aperture 84A of the ear 78A. The aperture 84B of the ear 78B of the mounting base 62 may have a diameter D7, equal to or smaller than the diameter D5 of the second end 226 of the pin 155, the difference, if any, selected to yield a press fit between the second end 226 of the pin 155, and the second aperture 84B of the ear 78B. The apertures 222A, 222B of the side members 220A, 220B may both have a diameter D8 larger than the diameter D5 of the second end 226 of the pin 155, the difference selected to yield a clearance fit between the second end 226 of the pin 155, and the apertures 84B, 222A, 222B.

The switch 68 as shown in FIGS. 10A-10D may include a switch sliding body 228. The sliding body 228 may be substantially rectangular and have a switch sliding axis 230. The sliding axis 230 may be coincident with or substantially parallel to the lever axis 152 when the switch 68 is disposed on the lever 64. The sliding body 228 has a sliding surface 232 that receives or is received by the first track 158. Depending on the shape of the first track 158, the sliding surface 232 may be disposed, by way of example, over or alternatively, inside the first track 158. An example sliding surface 232 is provided by a T-slot 234 that may extend a length L9 of the sliding body 228 and may be aligned with the axis 230. An example nominal value of L9 may be approximately 21 mm (0.80 inches). Two indicator arms 236A, 236B defining corresponding outboard sides 238A, 238B extend from opposite sides of the sliding body 228 on opposite sides of the T-slot 234. Each arm 236A, 236B may include the indicator line 168 referenced above. Each indicator line 168 may be formed its associated arm 236A, 236B as a recess or a projection. An example width W4 of the switch 68, across the outboard sides 238A, 238B of the arms 236A, 236B may be approximately 21 mm (0.80 inches). Each arm 236A, 236B may laterally extend approximately 6 mm (0.24 inches) beyond the lateral sides 165A, 165B respectively. An example width W5 of the lever 64 across the wings 166A, 166B of approximately 16 mm (0.63 inches) may also be exceeded by the spread of the arms 236A, 236B by approximately 2.5 mm (0.10 inches).

In a bottom surface 240 of the T-slot 234, a first and a second switch detent recess 242A, 242B, comprising part of the switch detent, may be positioned for engagement by a ball (not shown) of the switch plunger 198. The detent recesses 242A, 242B may be hemispherical in shape. The recesses 242A, 242B may be separated in the axial direction, i.e., the direction parallel to the axis 230, by a distance L10 substantially equal to a distance between the locked icon 167A and the unlocked icon 167B on the wings 166A, 166B. An example nominal value of L10 may be approximately 10 mm (0.40 inches). A magnet housing aperture 244 may pass through the bottom surface 240 of the T-slot 234. The first recess 242A may be engaged by the plunger 198 when the switch 68 is in the locked position, i.e., when the indicator line 168 is aligned with the locked icon 167A. The second recess 242B may be engaged by the plunger 198 when the switch 68 is in the unlocked position, i.e., when the indicator line 168 is aligned with the unlocked icon 167B.

The aperture 244 may receive the magnet housing 204 in a press fit relationship. The magnet 206 may be retained in the housing 58 for assembly purposes by petroleum jelly, or alternatively retained by an adhesive or by mechanical entrapment, e.g., a closure, a press fit. A lower side of the switch 68 may have an increased thickness in an area surrounding the aperture 244. The example magnet 206 and magnet housing 204 may be installed in the switch 68 when the switch 68 is slidably disposed on the lever 64 and the magnet housing aperture 244 is aligned with the switch travel slot 202.

The lever extension 70 as shown in FIGS. 9A-9F may include an extension sliding body 246. The sliding body 246 may be substantially rectangular and have an extension sliding axis 248 extending from a distal end 249 to a proximal end 250 of the extension 70. The extension sliding axis 248 may be coincident with or substantially parallel to the lever axis 152 when the extension 70 is disposed on the lever 64.

The sliding body 246 has a lever extension sliding surface 252 that receives or is received by the second track 162. Depending on the shape of the second track 162, the sliding surface 232 may be disposed, by way of example, over or alternatively, inside the first track 162. An example sliding surface 252 is provided by a T-slot 254 that may extend a length L11 of the sliding body 246 and may be aligned with the axis 248. An example nominal value of L11 may be approximately 77 mm (3.0 inches).

The outwardly facing contact surface 188 may be substantially continuous from the distal end 249 to the proximal end 250. An engagement head 258 may be provided at the distal end 249 of the extension 70. The engagement head 258 extends upwardly from the contact surface 188 and provides an angled engagement surface 260 for engagement by a thumb or a finger of a user of the tool 50. A plurality of distal engagement surfaces 262 may be provided in the contact surface 188 proximate to the head 258 for engagement by a user's finger or thumb. The distal engagement surfaces 262 may be defined by recesses or alternatively by projections. The lever extension 70 may similarly have a plurality of proximal engagement surfaces 264 in the contact surface 188 proximate to the proximal end 250.

In an upper surface 266 of the T-slot 254, a plurality, e.g., four, detent recesses, i.e., notches, first detent recess 268A, second detent recess 268B, third detent recess 268C, and fourth detent recess 268D, may be formed therein and positioned for engagement by a ball (not shown) of the extension plunger 172. The detent recesses 268A, 268B, 268C, 268D may be substantially hemispherical in shape. The recesses 268A, 268B, 268C, 268D may be laterally elongated to desensitize a lateral alignment of the recesses 268A, 268B, 268C, 268D with the plunger 172. The recesses 268A, 268B, 268C, 268D may be evenly separated in the axial direction, i.e., the direction parallel to the axis 248. The first detent recess 268A, being most proximal recess may be in alignment with the plunger 172 when the extension 70 is in a fully-stored position, e.g., the proximal end of the extension 70 is in engagement with the distal end of the end wall 182. The fourth recess 268D, being the most distal recess, may be in alignment with the plunger 172 when the extension 70 is in a fully extended position, e.g., the travel limit pin 178 is engaged by the proximal end 218 of the pin slot 216.

The pin slot 216 may be formed in the upper surface 266 and may extend an example width W3 axially for at least an anticipated example travel distance L12 of the extension 70. An example nominal value of W3 may be approximately 2 mm (0.08 inches). An example nominal value of L12 may be approximately 40 mm (1.6 inches). The pin 178 is received in the slot 216 after the lever extension 70 has been slidably received by the lever 64. The pin slot 216 may be of a depth H5 less than a thickness H6 of the extension. An example nominal value of H5 may be approximately 1 mm (0.04 inches). An example nominal value of H6 may be approximately 1.2 mm (0.05 inches). Having the slot 216 not extend through the entire thickness of the extension 70 is not required for the extension 70 to slide in a desired manner, but may aid in reducing intrusion of debris into the T-slot and an associated increase in resistance to sliding.

The extension 70 may be assembled to the lever 64 by sliding the extension 70 onto the lever 64, and then inserting the pin 178 through the pin aperture 176 in the lever 64 from the inner side 160 of the lever 64 to extend into the slot 216. If the pin aperture 176, as noted above, is provided as a blind hole, a clearance hole (not shown) may be provided in the lever in alignment with the slot 216. After sliding the extension 70 onto the lever 64, the clearance hole may be aligned with the pin aperture 176, and the pin 178 passed through the clearance hole and into the pin aperture 176. The height of the installed pin 178 must be fit within the available height of the slot 216. If the slot 216 extends through the extension, the pin 178 should be below the contact surface 188 for the comfort of the user of the handswitch 52.

In operation, the handswitch 52 is installed on the housing 58 by aligning the tabs 92A, 92B with the first channel 128A and the second channel and axially sliding the collar 88 over the proximal end 60 of the housing 58. The offset B1 of the tab centerlines 98A, 98B relative to the mounting axis 90 and the offset B2 of the channel centerlines 147A, 147B relative to the housing axis 140 may provide a visual cue to a user that allows faster initial alignment, and helps prevent an incorrect orientation and misinstallation, of the handswitch on the housing 58. The tabs 92A, 92B are received by the first channel 128A and the second channel. The tab wedge sides 100A1, 100A2, 100B1, 100B2 contact the first channel wedge sides 146A1, 146A2 and the second channel wedge sides. The wedge sides may cooperatively rotatively align the housing 58 and the handswitch 52 with continued axial movement therebetween to the engaged position, with the handswitch 52 being rotatively aligned with the handpiece housing 58, i.e., in an aligned position, in the engaged position. As the collar 88 approaches a fully-installed position, the ball 114 of the plunger 104 passes over the edge 150 of the notch 132 and drops into the notch 132. Once in the notch 132, the ball 114 is pressed by the spring 116 against the biasing surface 130, generating a biasing force. The biasing force biases the collar 88, and thus the handswitch 52 in its entirety, toward a seated position on the housing 58. In the seated position, the first tab's contact points 101A1, 101A2 are in contact with the first channel's contact points 148A1, 148A2, and the second tab's contact points 101B1, 101B2 are in contact with the second channel's contact points.

With the handswitch 52 installed on the housing 58, the connector 56 may be engaged with the housing 58. The connector 56 may aid in retaining the handswitch 52 on the housing 58.

In use, the handswitch may have its lever 64 selectively pivoted about the pivot axis 86 towards the housing to operate the tool 50, e.g., a saw, a bur, a drill, etc. The handpiece 54, as stated earlier, includes the housing 58. The handpiece 54 may have disposed within the housing 58 the magnetic field sensor 59. The magnetic field sensor 59 is in alignment with the switch magnet 206 when the run-safe switch 68 is in the unlocked position and the lever 64 is displaced downwardly towards and potentially against the housing 58. The sensor 59, as described above, may be connected to the controller 63 by the signal conductor 55 or wirelessly. Likewise, the motor 61, disposed in the housing 58, may be connected to the console 53 and a power source (not shown) therein by the power conductor 57. Communication of power and control signals between the handpiece 54 and the console 53 may be accommodated by the connector 56.

Actuation of the tool 50 depends on the field sensor 59 detecting the magnet 206. The controller 63 may effect a variation in power to a drive motor 61 responsive to a strength of magnetic field detected. Thus, within a sensing range of distance, as the magnet 206 gets closer to the sensor 59, the power and/or speed of the tool 50 increases. With the switch 68 in the locked position, the magnet 206 is kept out of the sensing range of distance of the sensor 59, and the motor 61 cannot be actuated.

To operate the tool 50 after the handswitch 52 is installed on the housing 58, the switch 68 is placed in the unlocked position on the lever. The switch 68 is placed in the unlocked position by sliding the switch 68 in a proximal direction from the locked position. To do so, the user may engage one or both of the arms 236A, 236B with one or more fingers to load the switch 68 in a direction parallel to the switch sliding axis 230, displacing the switch 68 proximally in the axial direction, i.e., a direction of the axis 230. The switch 68 may thus be moved to the unlocked position without applying a load to the lever against the switch spring 66. Sufficient axial force must be applied to the arm or arms 236 A, 236B to overcome a detent load resulting from engagement of the switch plunger 198 with the recess 242A. The switch 68 may be axially displaced to the unlocked position by overcoming this load. Travel of the switch 68 in the direction of the unlocked position may be limited by one of engagement of a proximal end of the sliding body 228 with the track end 208, and engagement of the magnet housing 204 with the proximal end 210 of the slot 202. Retention of the switch 68 in the unlocked position may be aided by engagement of the plunger 198 with the recess 242B. No force normal to the sliding axis 230 that might tend to pivot the lever about the pivot axis 86 is required to displace the switch 68 from the locked position to the unlocked position, or to move the switch 68 from the unlocked position to the locked position. The lever 64 is pivoted toward the housing, against the bias of the switch spring 66. As described above, when the magnet 206 in the switch 68 is within the sensing range, the sensor 59 may provide a signal to the controller 63. The controller 63 in turn may directly or indirectly provide power to a drive motor 61, also within the housing 58 to initiate motion of a tool bit 280. Accidental actuation of the tool 50 is avoided by sliding the switch 68 to the locked position. Release of the lever 64 by the user allows the spring 66 to pivot the lever 64 away from the housing 58, to an Off position.

The switch 68 may be returned to the locked position by the user by pushing the switch 68 axially in the distal direction. The operation is essentially the same as moving the switch 68 to the unlocked position, but in the opposite direction. The detent load of engagement of the plunger 198 with the recess 242B is overcome by the user. The switch 68 is slid in the distal direction by the user, with travel of the switch 68 relative to the lever 64 being limited by engagement of the magnet housing 204 with the distal end 212 of the slot 202. Retention of the switch 68 in the locked position may be aided by engagement of the plunger 198 with the recess 242A.

Figure 2:
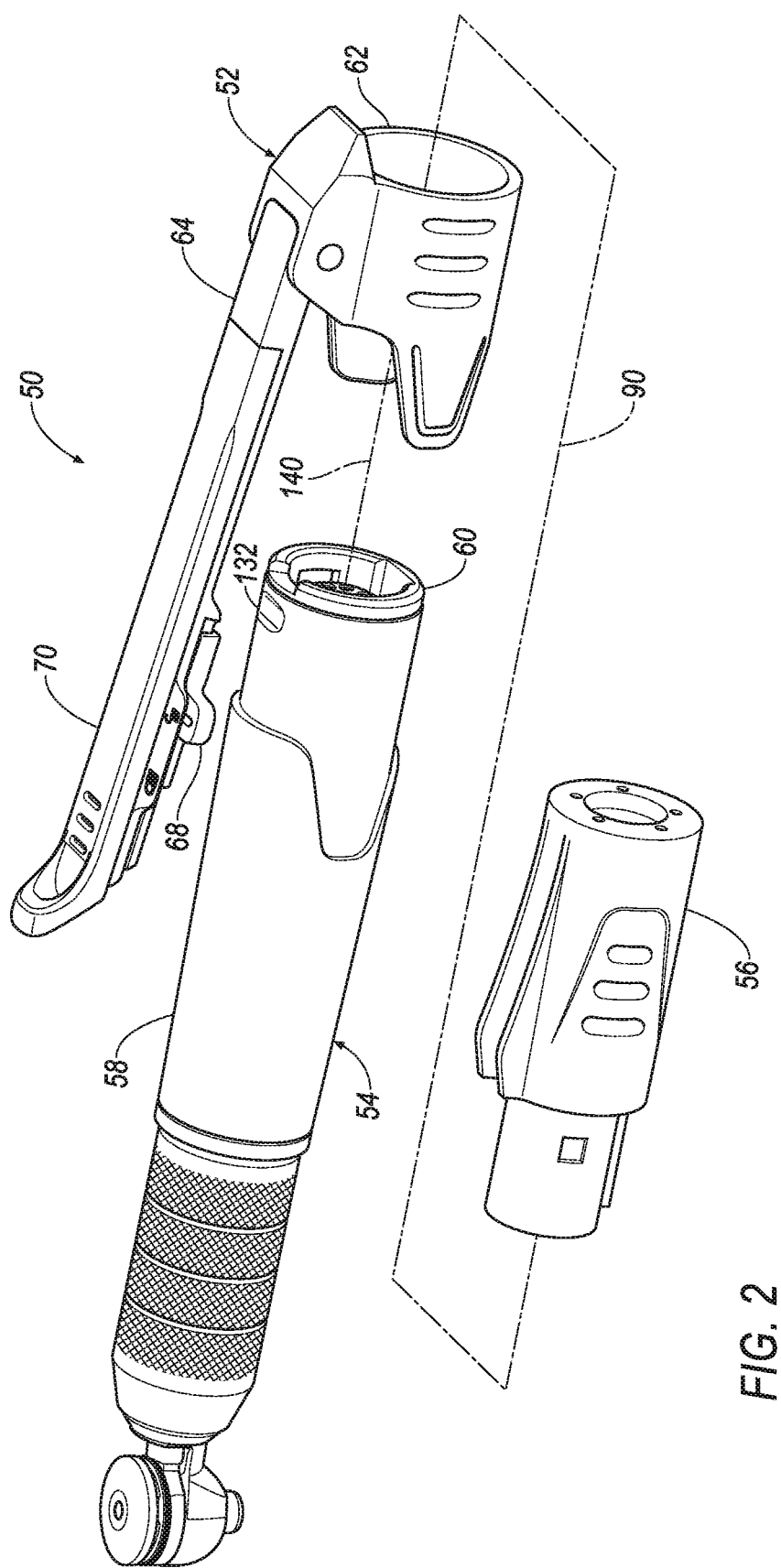
FIG. 2 is an exploded view of the handswitch, handpiece and connector of FIG. 1.
Figure 3A:
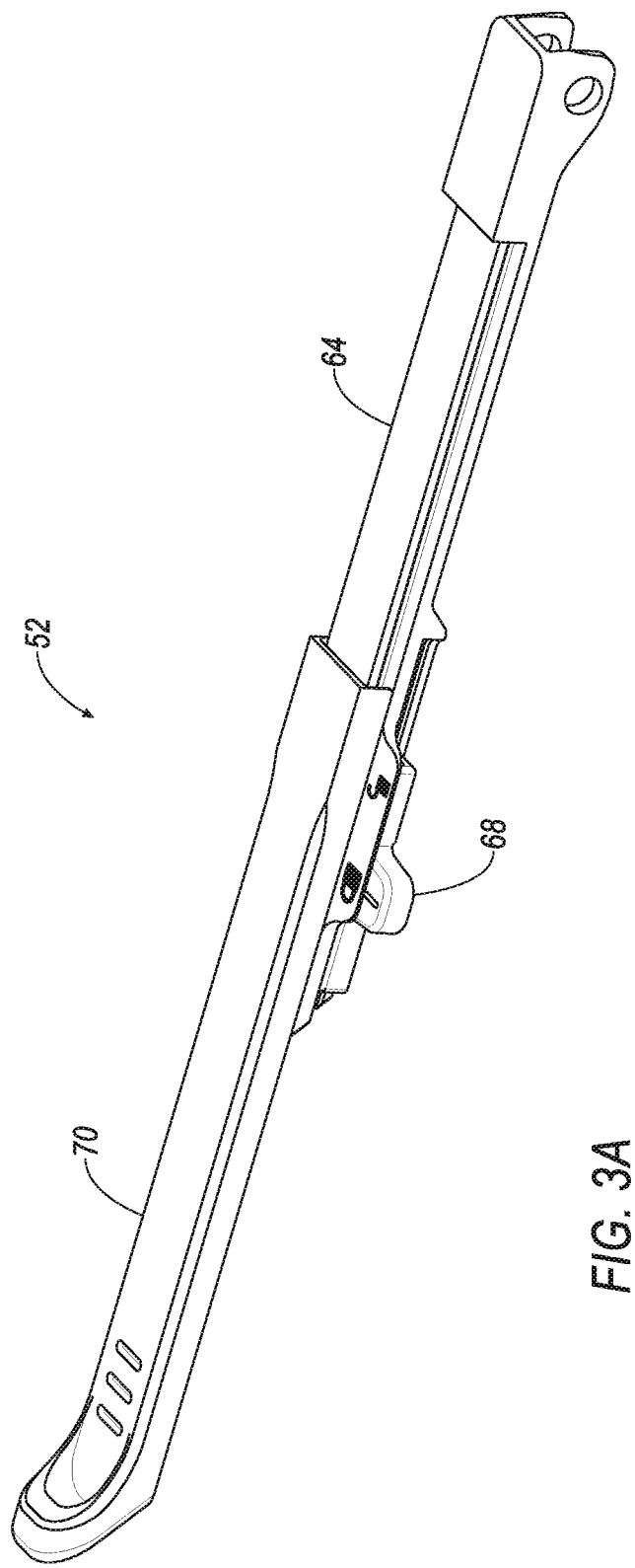
FIG. 3A is a perspective view of a lever of the handswitch of FIG. 2 with a lever extension fully extended.
Figure 3B:
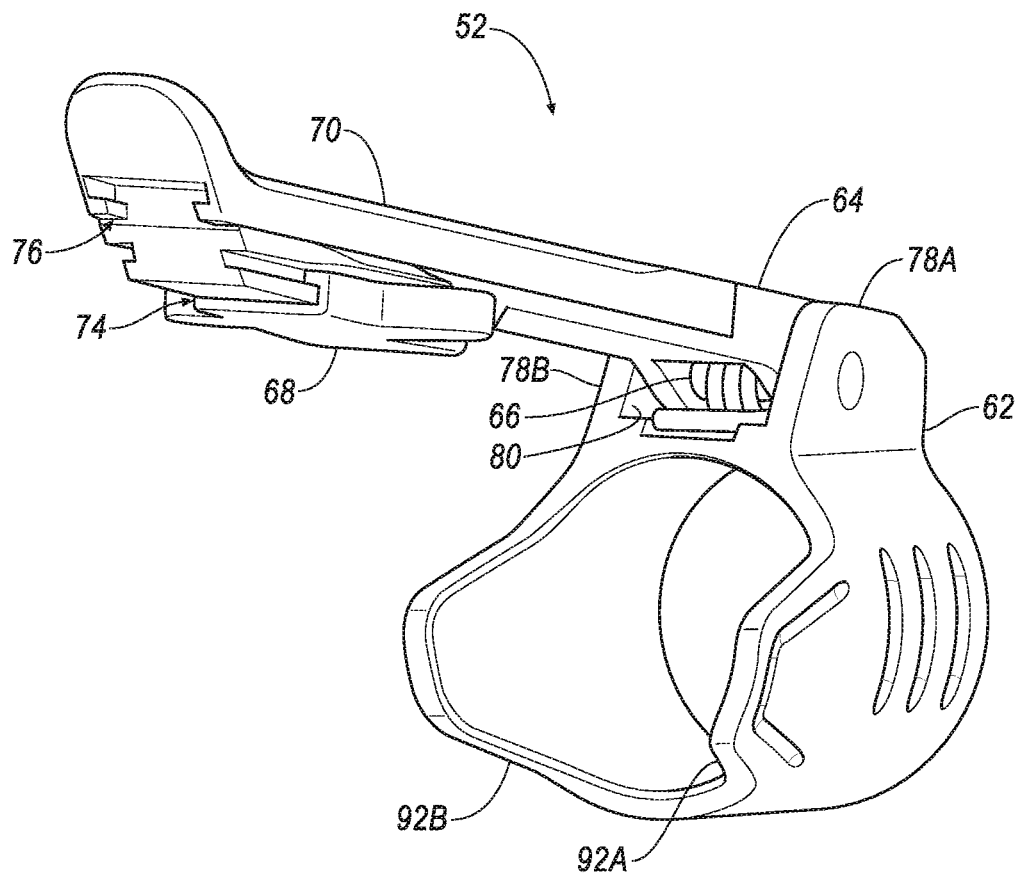
FIG. 3B is a second perspective view of the handswitch of FIG. 2 with the lever extension fully retracted.

The handswitch 52 may be used with the extension 70 in a fully withdrawn position as illustrated in FIGS. 1, 2 and 3B a fully extended position as illustrated in FIG. 3A, or any position in between. There are two intermediate positions illustrated for the example handswitch 52, but there may be more or fewer intermediate positions. The extension 70 may be retained in any of the exemplary four positions associated with the receipt of the ball of the plunger 172 in a corresponding one of the detent recesses 268A, 268B, 268C, 268D in the extension 70. The same detent effect could be achieved by installing the plunger 172 in the extension 70 and providing the detent recesses. The recesses 268A, 268B, 268C, 268D in the lever extension 70 may each be separated by a distance L13, with a total separation between recesses 268A and 268D of three times the distance L13. An example nominal value of L13 may be approximately 13 mm (0.50 inches). The recesses 268A, 268B, 268C, 268D may comprise part of the lever extension multi-position detent. The extension 70 provides a user of the tool 50 with a variable-length lever that can be adjusted to suit a hand size of the user.

When the extension 70 is in the fully withdrawn, i.e., stored, position, the contact surface 188 of the lever extension 70 and flush outer surface 186 of the proximal end portion 180 of the lever 64 cooperatively present a substantially continuous smooth surface for engagement by a user's finger. Retention of the extension 70 in the withdrawn position may be aided by engagement of the extension plunger 172 with the recess 268D. The user may axially displace the extension 70, i.e., slide the extension along the axis 248, by engaging pushing against the extension 70 in a direction of extension travel desired relative to the mounting base 62. The head 258 provides what may be the most prominent engagement feature of the extension 70 for finger engagement. Supplemental engagement features facilitating gripping of the extension 70 by a finger are provided by the distal engagement surfaces 262 and the proximal engagement surfaces 264. Such features 258, 262, 264 may resist slippage of the finger across the extension 70. Sliding the extension 70 from the withdrawn position toward the fully extended position requires that sufficient axial force be applied to the extension 70 in the desired direction of travel to overcome the detent force associated with engagement of the extension plunger 172 with the recess 268D.

An example withdrawn length of the combined lever 64 and extension 70 may be substantially equal to the sum of L4 and a distance between the proximal end 250 and the distal end 249 of the lever extension, such a total withdrawn length being approximately equal to 102 mm (4 inches). An example fully extended length of the combined lever 64 and extension 70 may be approximately 142 mm (5.6 inches). The extension 70 may be positioned anywhere between the withdrawn position and the fully extended position. A user may find it helpful to have the extension set to a particular intermediate position. Intermediate detent positions, as may be provided by recesses 268B and 268C, may prevent the lever extension translating away from desired intermediate positions along the axis 248 with little or no axial force. The extension 70 as illustrated has the two intermediate detent positions associated with recesses 268B and 268C, but this number of intermediate positions may be smaller or greater.

Travel of the extension 70 toward the fully extended position, and away from the end wall 182, is ultimately limited by engagement of the pin 178 with the proximal end 218 of the slot 216. Retention of the extension 70 in the fully extended position may be aided by engagement of the extension plunger 172 with the recess 268A. Return of the extension 70 to the withdrawn position may be achieved by pulling the extension 70 axially in the proximal direction until travel is limited by one of engagement between the proximal end 250 of the extension 70 against the end wall 182, and engagement of the pin 178 against the distal end 214 of the slot 216. Retention of the extension 70 in the withdrawn position may again be aided by engagement of the extension plunger 172 with the recess 268D.

In any extended position, i.e., any position other than the withdrawn position, the extension presents a significant contact pad, including the outer surface 188 and the head 258, separate from the proximal end portion 180, for engagement by a user's finger. The contact pad may present a width of the extension, e.g., approximately 10 mm (0.40 inches) and an approximate length of 85 mm (3.3 inches). Such a large area contact area, facilitated by locating the extension 70 on the track 162 on the outer side 164 of the lever 64, improves the comfort of the user's finger when depressing the extension 70 to operate the tool 50.

FIGS. 11 through 13B illustrate alternative mounting base configurations.

Figure 11:
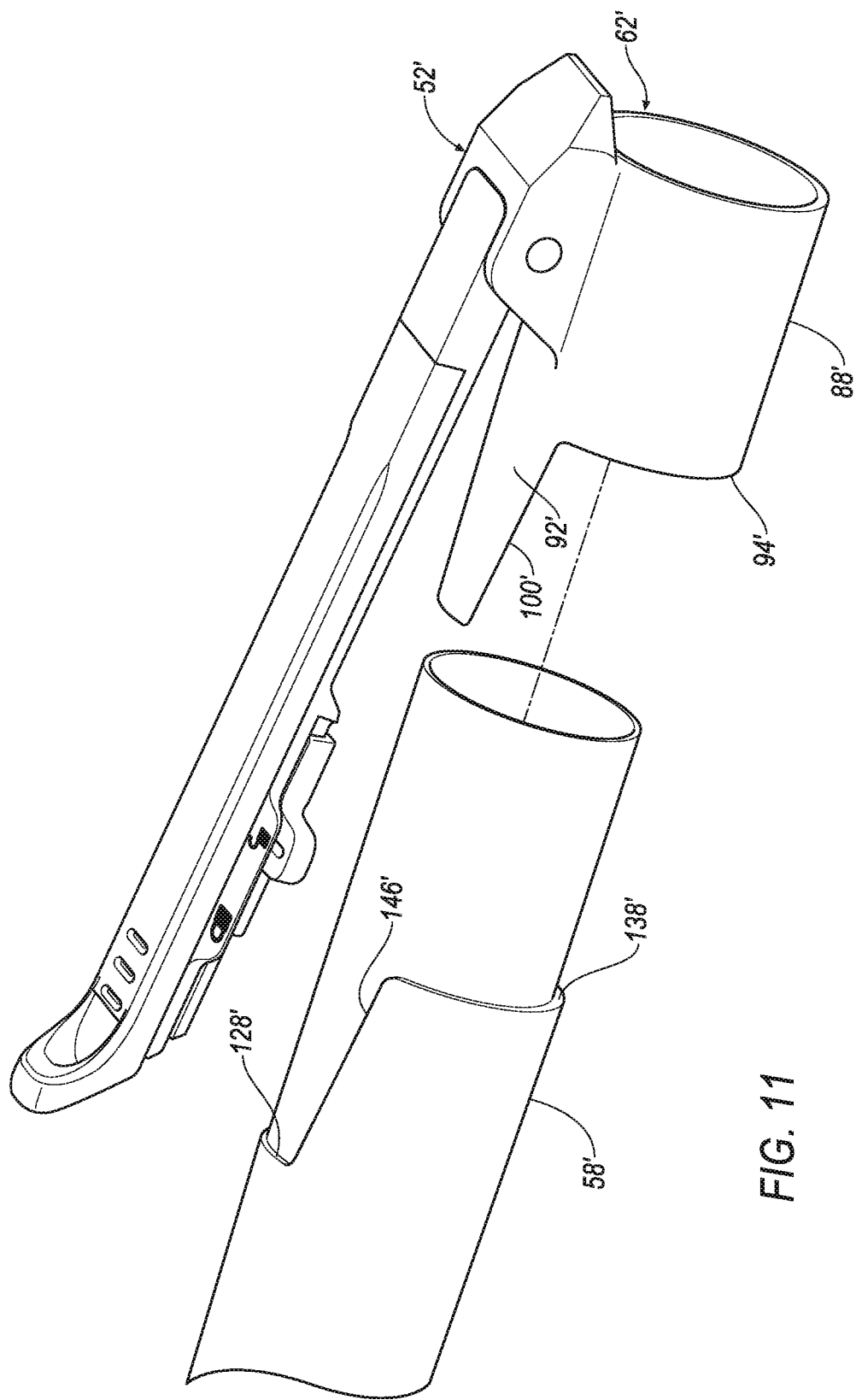
FIG. 11 is an exploded view of a first alternative interface between the handpiece and the handswitch.

FIG. 11 shows a handpiece housing 58' and a mounting base 62' with just a single positioning tab 92'. Wedge sides 100' of the tab 92' engage wedge sides 146' of a single receiving channel 128'. Although not illustrated, the base 62' and the housing 58' may include a detent like the mounting base detent 149 for retention of the handswitch 52' on the handpiece housing 58'. A contact point may also be provided between a peripheral wall 138' of the housing 58' and a distal edge 94' of a collar 88' at a bottom of the collar 88'.

Figure 12A:
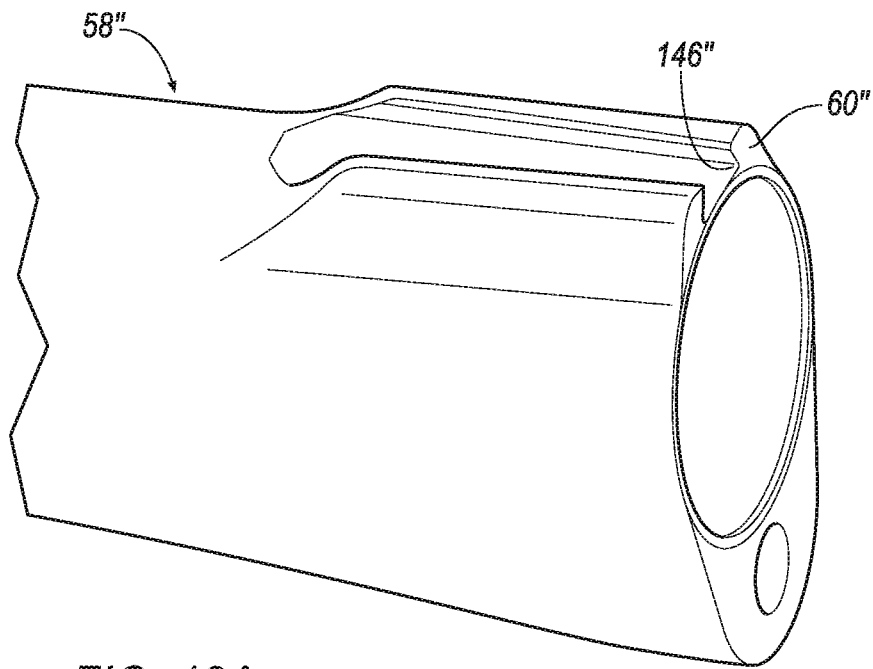
FIG. 12A is a perspective view of a handpiece housing illustrating a housing portion of a second alternative interface between the handpiece and the handswitch.
Figure 12B:
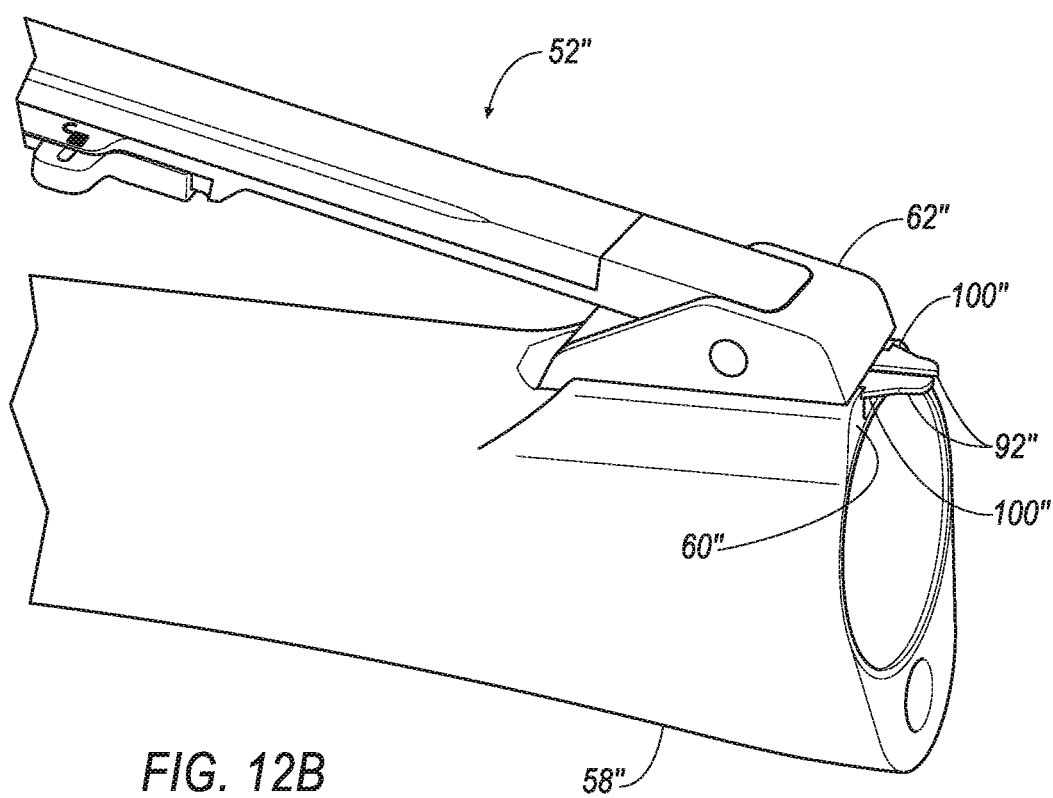
FIG. 12B is a perspective view of the handpiece housing of FIG. 12A with a handswitch installed illustrating the second alternative interface between the handpiece and the handswitch.

FIGS. 12A and 12B show a handpiece housing 58" with a receiving channel 146" that slideably receives a handswitch 52" with a mounting base 62". The mounting base 62" has retention tangs 92" with barbs 100". The tangs 92" are spring-biased to spread outward. When the barbs 100" pass an end of the channel 146", the tangs 92" spread, and the barbs 100" engage a proximal end 60" of the housing 58" on either side of the channel 146" to retain the handswitch 52".

Figure 13A:
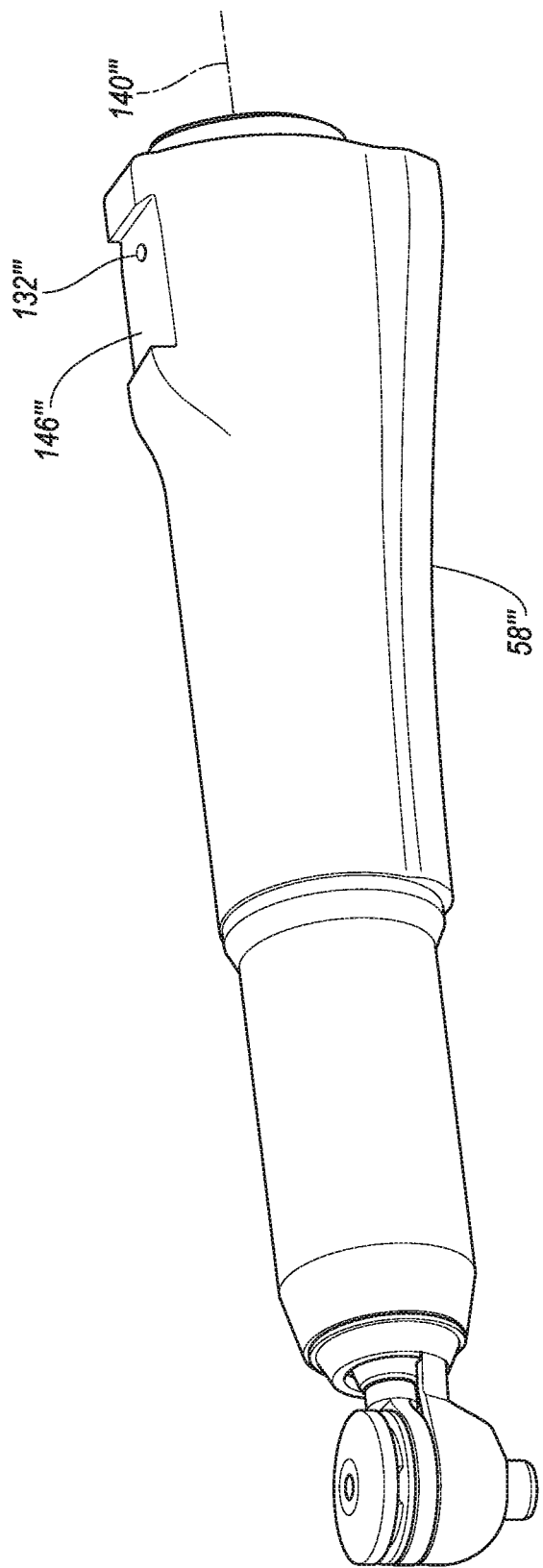
FIG. 13A is a perspective view of a handpiece and handpiece housing illustrating a housing portion of a third alternative interface between the handpiece and the handswitch.
Figure 13B:
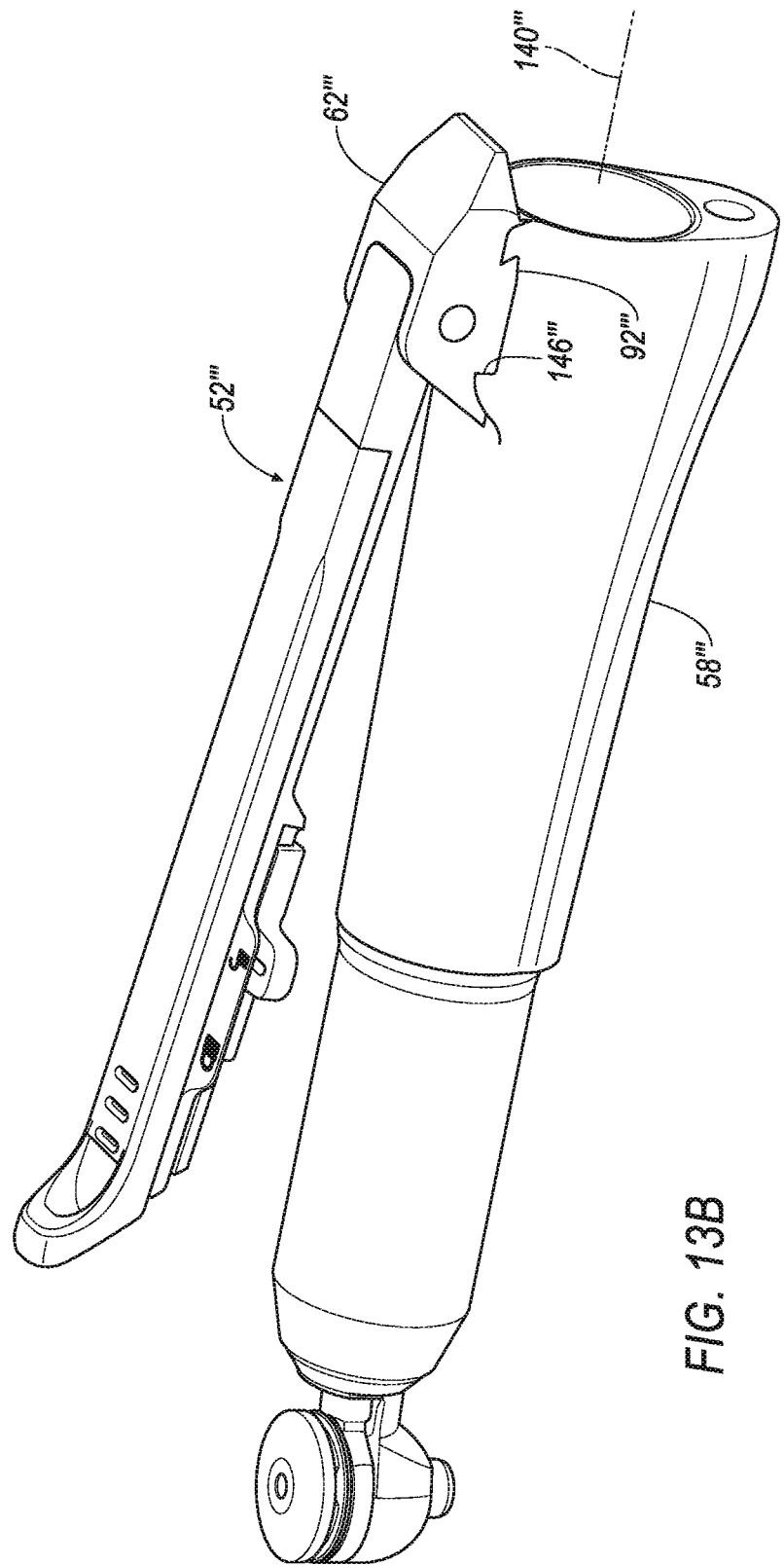
FIG. 13B is a perspective view of the handpiece and handpiece housing of FIG. 13A with a handswitch installed illustrating the third alternative interface between the handpiece and the handswitch.

FIGS. 13A and 13B show a handpiece housing 58''' with a receiving channel 146''' having a dovetail profile and disposed transversely to a housing axis 140'''. A handswitch 52''' has a mounting base 62''' with a rail 92''' having a dovetail shape complementary to that of the channel 146'''. The channel 146''' has a detent notch 132''' therein for engagement by a plunger (not shown) disposed in the mounting base 62'''. The rail 92''' of the mounting base 62''' is received by the channel 146''' and is retained therein by engagement of the plunger with the detent notch 132'''.

A yet alternative handswitch 52'''' having an alternative lever 64'''', switch spring 66'''', run-safe switch 68'''' and lever extension 70'''' is shown in FIGS. 14A-17. The lever 64'''' may be received by a receiving pocket 80'''' of a mounting base 62''''. A pivot pin 155'''', centered on a pivot axis 86'''', may be used to pivotably connect the lever 64'''' to the base 62''''. The mounting base 62'''' may also include an example annular collar 88'''' that defines a mounting axis 90''''.

Figure 14B:
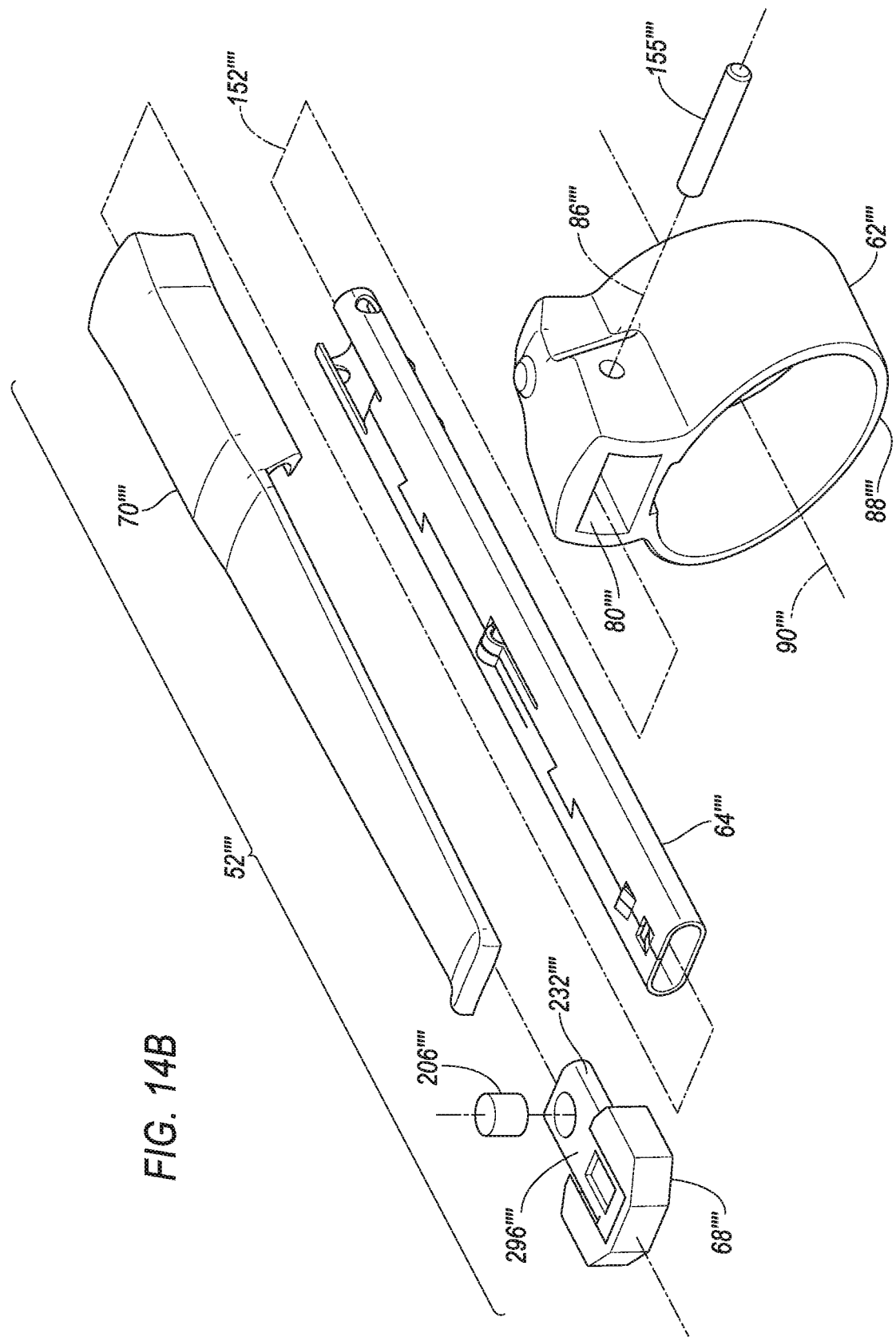
FIG. 14B is an exploded perspective view of the handswitch of FIG. 14A.
Figure 14C:
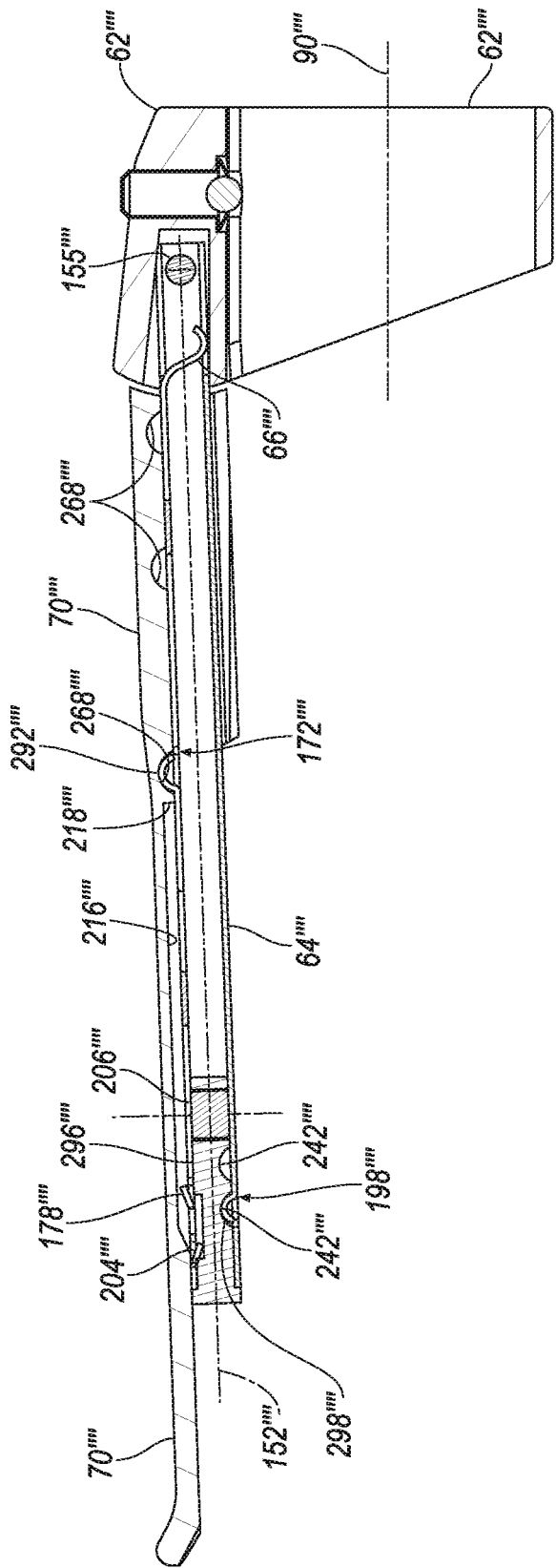
FIG. 14C is a sectional side view of the handswitch of FIG. 14A.

The lever extension 70'''' is slidably disposed on the lever 64'''' for selective translation by a user between a fully withdrawn position, shown in FIG. 14A and FIG. 14C, and a fully extended position, not shown, but analogous to the fully extended position of the lever extension in FIG. 3A. The switch 68'''' is slidably disposed on the lever 64'''' for selective translation by a user between a unlocked position and a locked position.

The lever 64'''' defines a lever axis 152'''' substantially normal to at least a direction of the pivot axis 86''''. The lever extension 70'''' and the run-safe switch 68'''' may each have a respective sliding surface 252'''', 232'''' aligned with the lever axis 152''''.

The lever 64'''' has a first track 158'''' and a second track 162'''' extending substantially parallel to the lever axis 152''''. The first track 158'''' is located, in an installed position, closer to the mounting axis 90'''' than the second track 162''''. The second track 162'''' is on an outer side 164''''. The first track 158'''' may include an interior inward-facing, i.e., an interior inner side 160'''', of the lever 64''''. Neither the inner side 160'''' nor the outer side 164'''' are required to be exterior surfaces of the lever 64''''. The lever 64'''', being hollow, may have multiple inner sides, e.g., an interior inner side 1632'''', and an exterior inner side 163'''', most proximate to the axis 90''''. The lever 64'''' may likewise have multiple outer sides.

The lever 64'''' may be formed of sheet metal by stamping. The lever 64'''' may include the switch spring 66'''' as an integral part of the lever 64'''', formed integrally therewith, for disposition between the rest of the lever 64'''' and the base 62''''. The spring 66'''' may bias the lever 64'''' about the pivot axis 86''''. The lever 64'''' may include a plurality of (e.g., two) joining tabs 282'''' at a first seam edge 284'''' having a first shape, each of the tabs 282'''' being received by a joining notch 286'''' at a second seam edge 288'''' of the lever 64''''. An example shape for the tabs 282'''' and the notches 286'''' may be a dovetail as illustrated.

The lever 64'''' may include a downwardly extending switch-stop tab 204'''' and an upwardly extending extension-stop tab 178''''. The stop tabs 204'''', 178'''' may be used to limit travel of the switch 68'''' and the lever extension 70'''' respectively as described in more detail below.

The lever 64'''' may also include a switch plunger 198'''' and an extension plunger 172''''. The extension plunger 172'''' may be formed in the outer side 164'''' of the lever 64'''', and may be in the form of a cantilevered leaf spring 290'''' with an integral projection 292'''' disposed at an end thereof. The switch plunger 198'''' may be formed in the exterior inner side 163'''' of the lever 64''''. The switch plunger 198'''' may be in the form of a cantilevered leaf spring 296'''' with a projection 298'''' integral therewith disposed at an end thereof.

The lever extension 70'''' is slidably disposed on the second track 162''''. The sliding surface 252'''' of the lever extension 70'''' may receive the second track 162''''.

An extension travel slot 216'''' may be formed in an upper surface 266'''' of the sliding surface 252''''. The slot 216'''' may extend for at least an anticipated example travel distance of the extension 70''''. The extension-stop tab 178'''' is received in the slot 216'''' after the lever 64'''' has been slidably received by the lever extension 70''''. The tab 178'''' may elastically deflect upon initial receipt of the lever 64'''' by the sliding surface 252'''' of the lever extension 70''''. When the extension 70'''' is pushed over the lever 64'''' a sufficient distance, the tab 178'''' is received by the slot 216'''' and snaps back to extend into the slot 216''''.

Figure 16:
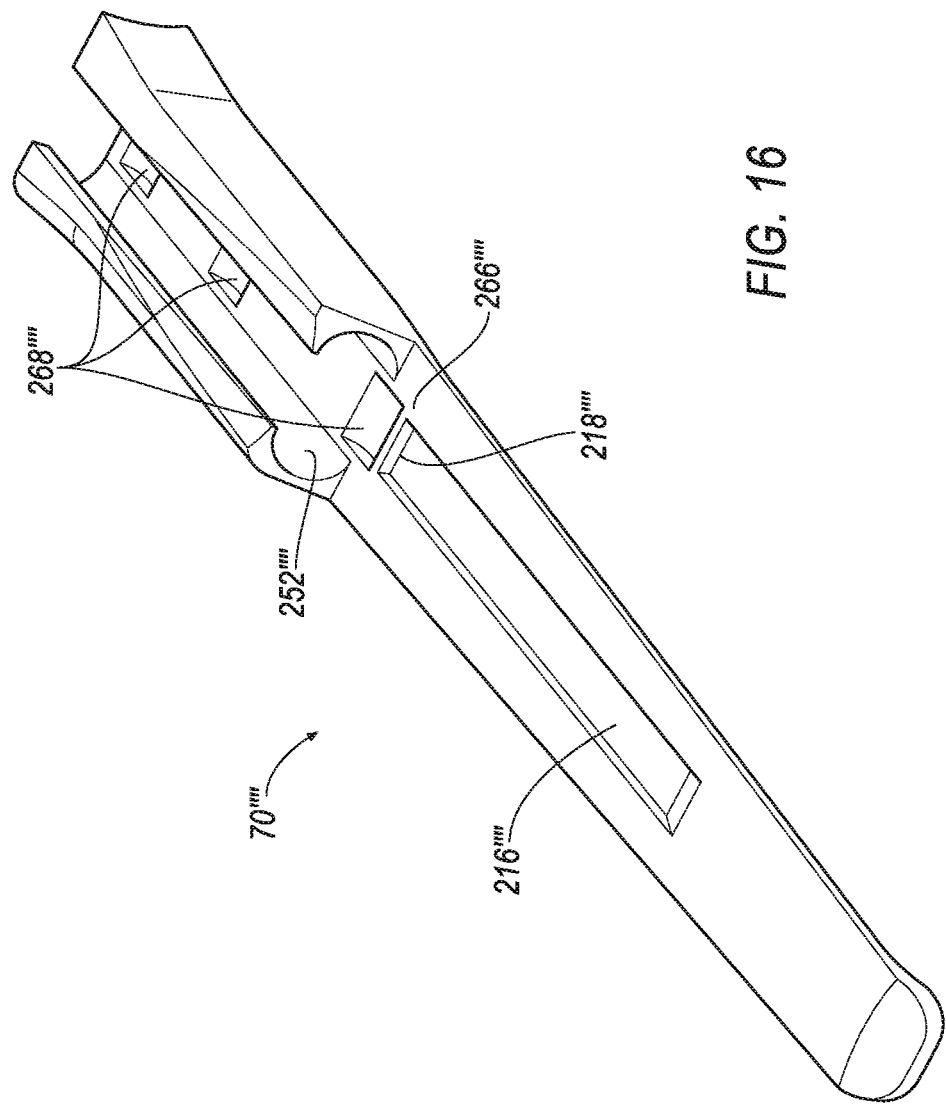
FIG. 16 is a bottom left front perspective view of a lever extension of the handswitch of FIG. 14A.

A plurality, e.g., three, detent recesses, i.e., notches, 268'''' may be formed in the upper surface 266'''' and positioned for engagement by the projection 292'''' of the extension plunger 172''''. The detent recesses 268'''' may be substantially semi-cylindrical in shape, and may extend laterally across substantially a full width of the upper surface 266''''. The recesses 268"" may be evenly separated in the axial direction, i.e., the direction parallel to the axis 152"", or, as illustrated in FIG. 14C and FIG. 16, may be spaced unevenly. A most distal of the recesses 268"" may be in alignment with the plunger 172"", and more particularly the projection 292"" thereof, when the extension 70"" is in a fully-stored position. A most proximal of the recesses 268"", may be in alignment with the plunger 172"", i.e., the projection 292"" when the extension 70"" is in the fully extended position, e.g., the fully extended position being achieved when the tab 178"" is engaged by a proximal end 218"" of the slot 216"".

Figure 17:
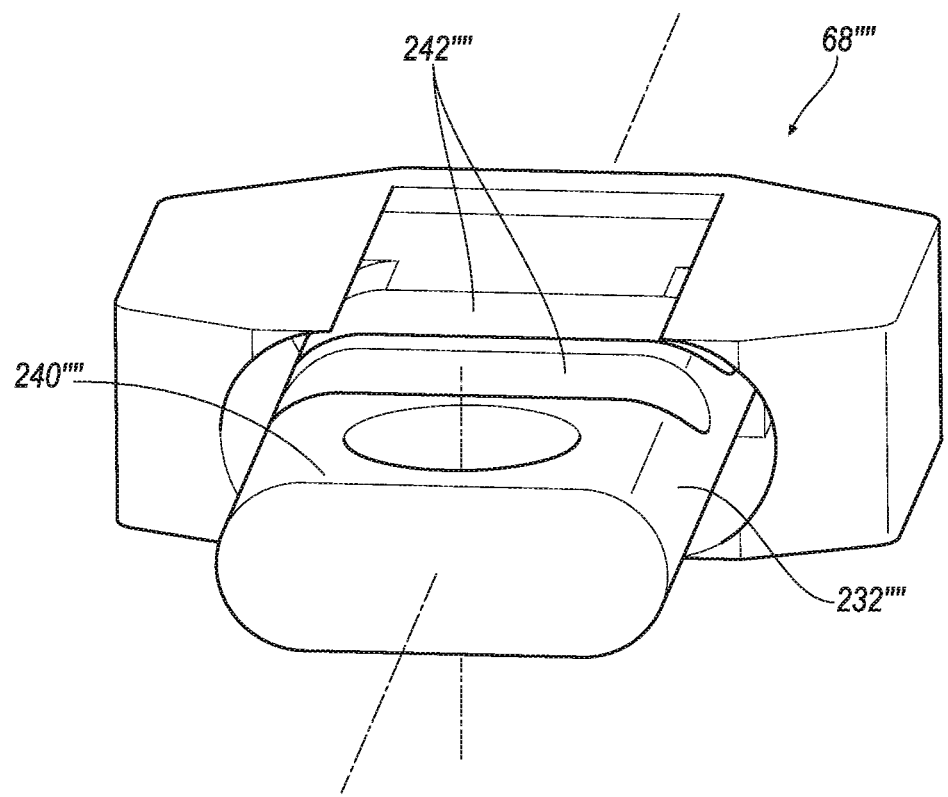
FIG. 17 is a bottom left rear perspective view of a switch of the handswitch of FIG. 14A.
Figure 18:
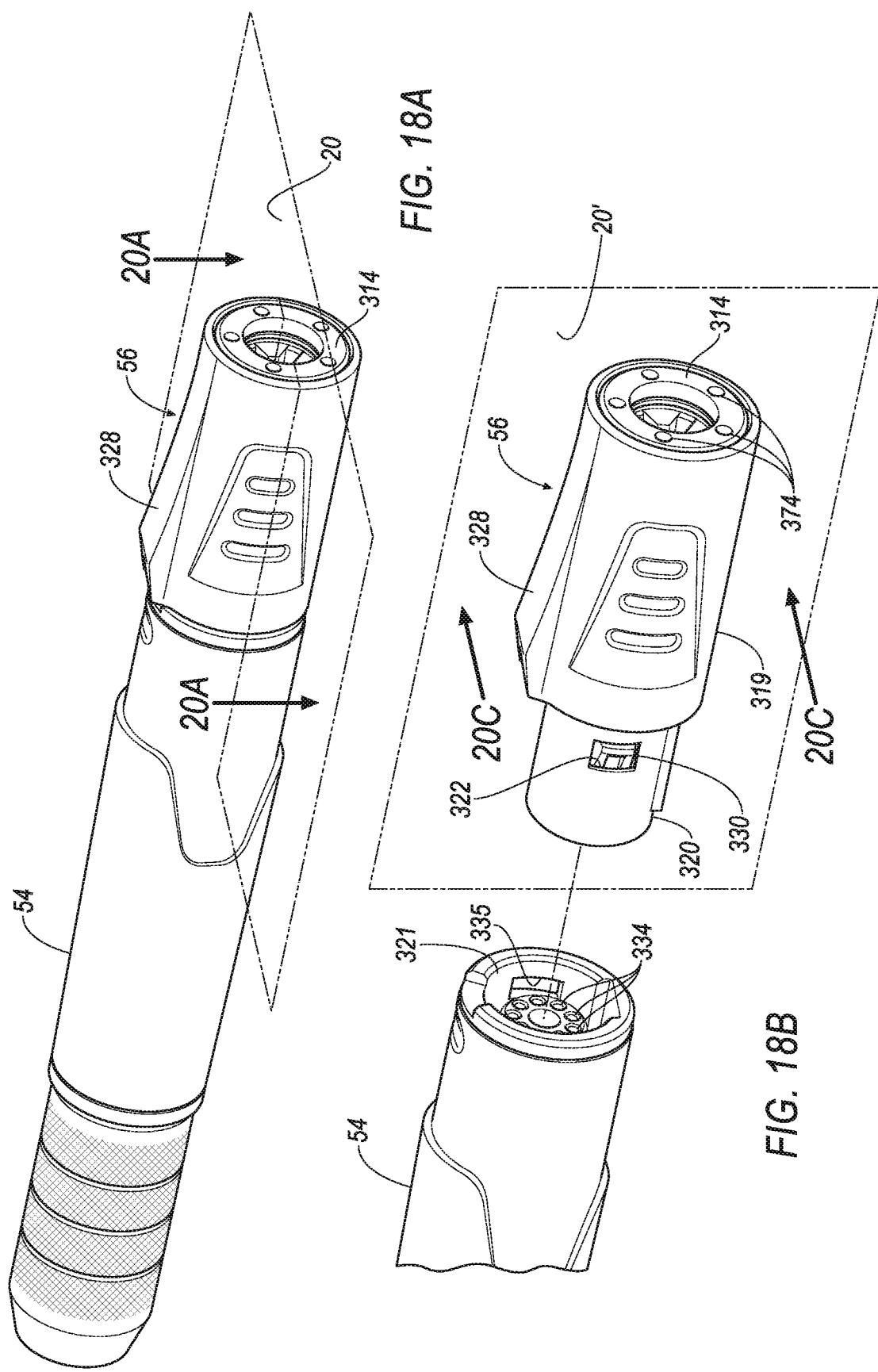
FIG. 18A is a perspective view of a handpiece and a connector in a connected position.
FIG. 18B is a perspective view of the handpiece and the connector of FIG. 18A in a released position.
Figure 19:
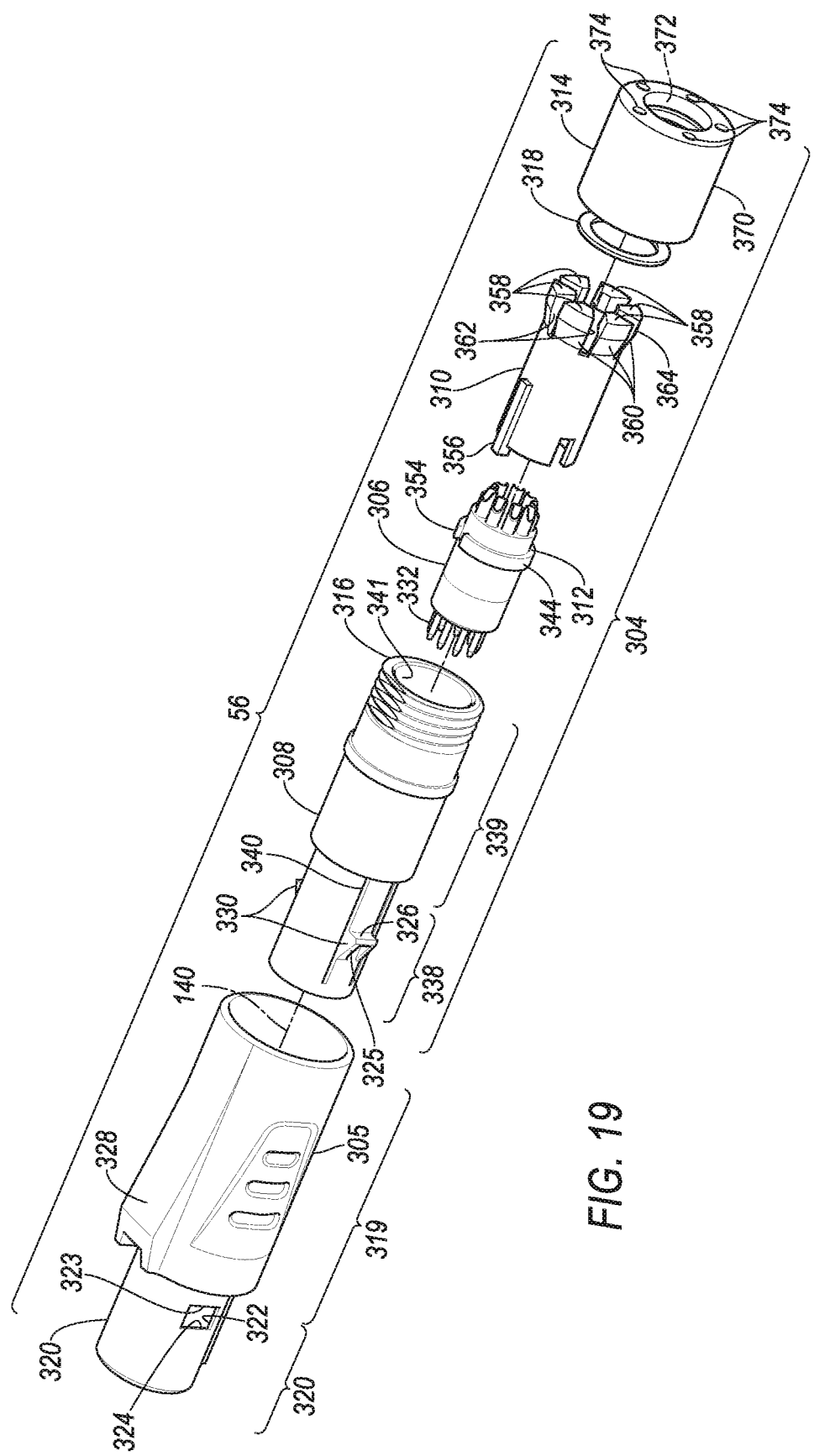
FIG. 19 is an exploded view of the connector of FIG. 18B.

Two detent recesses 242"" may be formed in a bottom surface 240"" of the sliding surface 232"" of the switch 68"". The recesses 242"" may be positioned for engagement by the projection 298"" of the switch plunger 198"". The detent recesses 242 may be semi-cylindrical in shape and may extend laterally across an entire width of the switch 68"", as illustrated in FIG. 17. The recesses 242"" may be separated in the axial direction, i.e., the direction parallel to the axis 152"", by a distance substantially equal to a distance between locked and unlocked positions of the switch 68"". A more distal of the recesses 242"" may be engaged by the projection 298"" when the switch 68 is in the locked position. A more proximal of the recesses 242"" may be engaged by the projection of the plunger 198"" when the switch 68"" is in the unlocked position. A magnet 206"" may be press fit in a magnet aperture 244"" in the switch 68"".

An upper surface 300"" of the sliding surface 232"" of the switch 68"" may include a switch travel slot 202"" formed therein. An axial length of the slot 202"" may be determine a travel range of the switch 68"" relative to the lever 64"". The switch-stop tab 204"" is received in the slot 202"" after the switch 68"" has been slidably received by the first track 158"" of the lever 64"". The tab 204"" may elastically deflect upon initial receipt of the sliding surface 232"" of the switch 68"" by the first track 158"" of the lever 64"". When the switch 68"" is pushed into the lever 64"" a sufficient distance, the tab 204"" is received by the slot 202"".

The connector 56 may be beneficially configured to facilitate engagement with and release from the handpiece 54. FIGS. 18A-23 show an example connector 56. The connector 56 may be connected to a first end of the cable 51. The connector 56 and the cable 51 may be included as elements of an electrical cable assembly 301. The cable assembly 301 may further comprise a second connector 302 fixed to a second end of the cable 51. The second connector 302 is illustrated schematically, and may or may not be identical to the connector 56. The cable assembly 301 and the handpiece may collectively comprise a surgical system 303.

The connector 56 includes an axially extending cable end receiver 304 and an outer sleeve 305. The cable end receiver 304 may be fixed directly to an end of the cable 51. The outer sleeve 305 receives and is disposed over substantially an entire length of the cable end receiver 304.

The cable end receiver 304 includes a pin holder 306 that is disposed within an inner sleeve 308 and is fixed thereto. A bushing 310 may be disposed against a proximally facing side 312 of the pin holder 306 to retain or aid in retaining the pin holder 306 inside of the inner sleeve 308. A retaining nut 314 may be disposed over a proximal end 316 of the inner sleeve 308 to aid in the retention of the pin holder 306 within the inner sleeve 308. A washer 318 may be coaxially disposed between the nut 314 and the inner sleeve 308. The outer sleeve 305 extends over substantially an entirety of the receiver 304, including the nut 314 if included, such that the receiver 304 cannot be gripped by a user to pull the connector 56 from the handpiece 54. The connector 56 can only be removed from the handpiece 54 by gripping the outer sleeve 305 and then pulling away from the handpiece 54, i.e., in a proximal direction. The constituent elements will be described in more detail below.

The outer sleeve 305 is substantially cylindrical and includes a gripping portion 319 and an insertion portion 320. The insertion portion 320 may be of a substantially constant first outside diameter and a substantially constant first inside diameter, both sized to be received by a handpiece electrical receptacle 321. The receptacle may define an annular gap between a center boss and a surrounding inside diameter surface. The insertion portion 320 may also include one or more windows 322 for receipt of a corresponding number of retention wedges 330 disposed on the inner sleeve 308. The illustrated insertion portion 320 shows two such windows 322. The windows 322 are shown as being oppositely disposed across the axis 140 from each other. Each of the windows 322 may have a first surface, e.g., a proximal engagement surface 323 and a second surface, e.g., a distal engagement surface 324 for respective engagement with a distally facing ramp surface 325 of the wedge 330 and a proximally facing stop surface 326 of the wedge 330.

Figure 22:
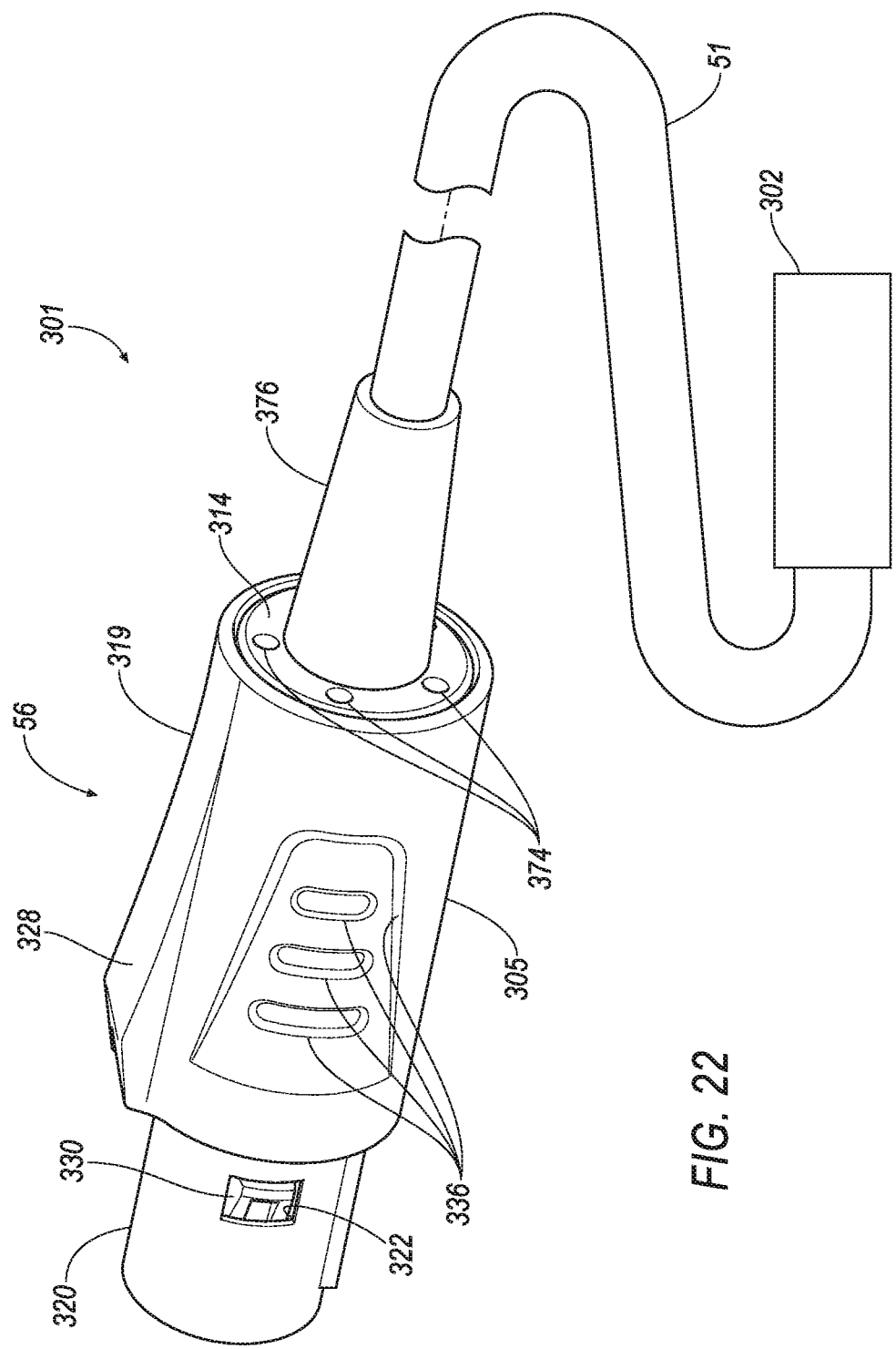
FIG. 22 is a perspective view of a cable assembly including the connector of FIG. 18B.
Figure 23:
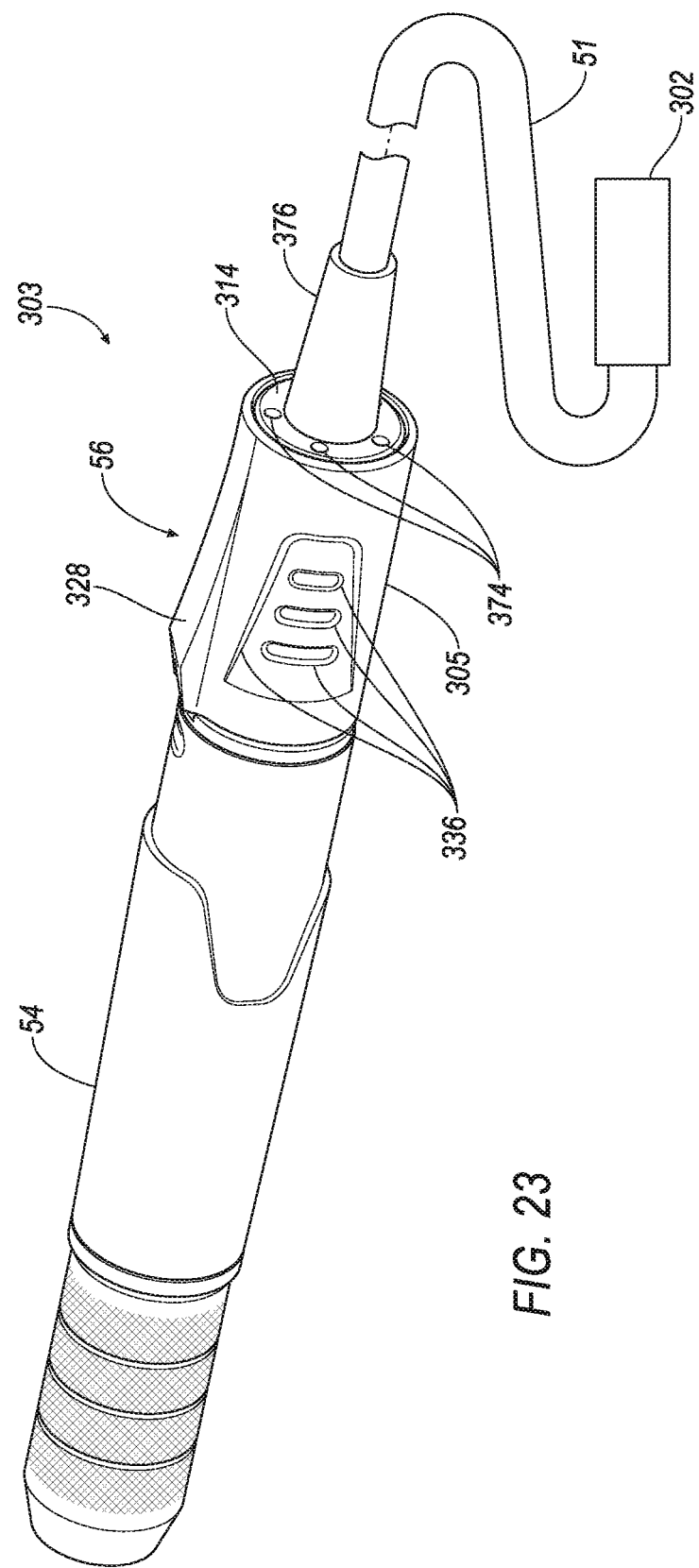
FIG. 23 is a perspective view of a surgical system including the connector and handpiece of FIG. 18A.

The gripping portion 319 of the outer sleeve 305 may include at a raised alignment surface 328. The alignment surface 328 may present as a lobe, e.g., a raised surface extending radially further from the axis 140 than an oppositely disposed surface of the outer sleeve 305, that may align with, for example, the proximal tab 82 of FIG. 5C, to facilitate alignment with the handpiece 54. Such alignment also yields alignment of pins 332 of the connector 56 with receiving sockets 334 within the receptacle 321 of the handpiece 54, and alignment of the wedges 330 with engagement recesses 335 disposed in the inside diameter surface of the annular gap of the receptacle 321. The gripping portion 319 may also include gripping surfaces 336, e.g., a plurality of parallel recesses and a V-shaped surface pocket as shown in FIG. 22, or a plurality of raised edges on sides thereof. A length L14 of the outer sleeve 305 is sufficient to substantially cover the assembled inner sleeve 308, pin holder 306, bushing 310, washer 318 and nut 314.

The inner sleeve 308 includes a shank portion 338 and a base portion 339. The shank portion 338 is substantially entirely disposed within the insertion portion 320 of the outer sleeve 305. The wedges 330 may be mounted to the shank portion 338. More specifically, each wedge 330 may be fixedly mounted to an associated resilient and elastically deflectable beam 340. Together, the wedge 330 and the beam comprise a resilient clip. Each beam 340 and wedge 330 may be formed integrally with the shank portion as a single unitary forming. The beams 340 may be longitudinally oriented parallel to the axis 140 on opposite sides of the axis. The beams 340 may be defined by longitudinal slits in the shank portion 338, and may have each of a distal end and a proximal end disposed within and fixed to the shank portion 338. The beams 340 may have a thinner cross-section thickness than the rest of the shank portion 338 to facilitate deflection. The base portion 339 is substantially entirely disposed within the gripping portion 319 of the outer sleeve 305. The inner sleeve 308 is able to axially translate a limited distance within the outer sleeve 305. The inner sleeve 308 includes an inner chamber 341 that may receive each of the pin holder 306 and the bushing 310. The pin holder 306 and the bushing 310 are both fixedly inserted into the inner chamber 341.

The pin holder 306 includes a pin holder core 342 and a plurality of the pins 332 mounted within and fixed to the pin holder core 342. A locator ring 344 may be formed as an integral unitary portion of the core 342. The pin holder core 342 may be made of a non-conductive material, e.g., rubber, plastic. The pins 332 may be made of a rigid conductive material, e.g., metal.

A distal portion of the pin holder 306 is distal to the locator ring 344 and may be disposed within the shank portion 338 of the inner sleeve 308. A proximal portion of the pin holder 306 is proximal to the locator ring 344 and may be disposed within the base portion 339. A plurality of pins 332, e.g., nine, may be disposed in parallel to the axis 140 in the pin holder 306, with tips of the pins 332 extending beyond the core 342 on a pin distal end 346 and wire receiving pockets disposed on the proximal end 348 of the pins 332. The core 342 may be hollow, e.g., have a cavity 350 open on a proximal end thereof.

The bushing 310 may have an interior chamber that extends a length of the bushing 310. The bushing 310 may have an opening at a distal end 352 sized to receive the proximal end of the pin holder 306. Travel of the bushing 310 relative to the pin holder 306 in the axial direction within the inner sleeve 308 may be limited by the locator ring 344 of the core 342. The travel of the bushing 310 may be so limited by engagement between the proximally facing side 312 of the pin holder 306, e.g., a proximal side of locator ring 344 serving as a pin holder core locator surface and the distal end 352 of the bushing 310.

The locator ring 344 may include a keyway notch 354 for receipt of a keytab 356 formed on the bushing 310. Alignment of the keytab 356 and the keyway notch 354 ensure alignment of the bushing 310 with the pin holder 306.

The bushing 310 may also include a plurality of cable engagement feet 358, each disposed at the end of a bushing leg 360. The bushing legs 360 may be defined by a corresponding plurality of slots 362 in a proximal end 364 of the bushing 310. The bushing legs 360 may define a rake edge 366 for engagement with a rake notch 368 on an inside diameter of the base portion 339 of the inner sleeve 308. The engagement between the rake edge 366 and the rake notch 368 aids in retaining each of the bushing 310 and the pin holder 306 in the inner sleeve 308. The cable engagement feet 358 are located at the proximal end 364 of the bushing 310 and are orientated to face radially inwardly. The feet 358 may engage the cable 51 when the connector 56 is fixed to the cable 51.

The nut 314 includes a threaded cylindrical body 370 and a proximal end flange 372 at a proximal end of the cylindrical body 370. The nut 314 includes threads on an inner diameter of the threaded cylindrical body 370 that may be in threaded engagement with threads on an outer diameter of the proximal end 316 of the inner sleeve 308. A distal end of the nut 314 may engage a proximally-facing engagement surface of the base portion 339 of the inner sleeve 308, limiting travel of the nut 314 thereon. A plurality, e.g., five, spanner pin apertures 374 may be formed in the end flange 372. The spanner pin apertures 374 may receive the engagement pins (not shown) of a spanner wrench (not shown).

The washer 318 may be disposed inside the nut 314, between the proximal end 316 of the inner sleeve 308 and the end flange 372.

As part of an assembly process, the cable 51 may be connected to the pins 332 within the pin holder 306. Individual conductors 55 of the cable 51 may each be placed in a pre-determined pin pocket of the distal end 346 and fixed to, e.g., soldered to, the associated pin 332. After the conductors 55 of the cable 51 are connected to the pins 332, the pin holder 306 and the bushing 310 may be placed into or connected to a mold (not shown) that encloses an end portion of the cable proximal to the bushing 310. An insulator 376 having an uncured liquid form, e.g., silicone, may be injected into the mold, and thus into the connector 56, sealing the ends of the pins 332 disposed inside the bushing 310 and over the cable 51. The cured insulator 376, i.e., the overmolding 376, is solid. The overmolding 376 may be elastically flexible, allowing a portion of the cable over which the overmolding 376 is disposed, to flex. The overmolding 376 may protect the pins 332 on the end of the pin holder 306 in the connector 56 from contamination.

The washer 318 may be disposed inside the nut 314, between the end flange 372 and the proximal end 316 of the inner sleeve 308. The nut 314 may be threaded over the inner sleeve 308 after forming the overmolding 376. Thus, the washer 318 may be pressed against the end flange 372 by the overmolding 376.

The assembled cable end receiver 304, i.e., the inner sleeve 308, pin holder 306, bushing 310, nut 314, washer 318, and cable 51, may be axially and rotatively aligned with the outer sleeve 305 and pressed thereinto. The inner sleeve 308 may have a guide rail 378 that is received by a complementary guide slot 380 to ensure axial alignment of the wedges 330 with the windows 322.

When the connector 56 is fully assembled, the outer sleeve 305 extends over substantially the entire combined inner sleeve 308 and nut 314.

In operation, the connector 56 in an uninserted condition has the wedges 330 extending radially outwardly through the windows 322 beyond the first outside diameter of the insertion portion 320. In the uninserted condition, the outer sleeve 305 is in a latching position with respect to the inner sleeve 308. In the latching position, the wedges 330 are in substantial axial alignment with the windows 322 of the outer sleeve 305, allowing the beams 340 to be substantially undeflected and the wedges 330 to extend beyond the first outside diameter of the insertion portion 320. The connector 56 is aligned with the handpiece 54 using the alignment surface 328 to orient the connector 56 with respect to the handpiece 54. The connector 56 is then pushed into engagement with the handpiece 54. During insertion, engagement of the ramp surface 325 of the wedges 330 against an inside diameter of the receptacle 321 of the handpiece 54 biases the wedges 330 down into the windows 322, against the resistive force of the beams 340. The inner sleeve 308 and the outer sleeve 305 remain in the latching position, with the wedges 330 aligned with the windows 322. As the windows 322 come into axial alignment with the engagement recesses 335 in the handpiece 54, the wedges 330 are restored to the extended position by the elastic beams 340. The wedges 330 are resultantly disposed in part in the recesses 335.

The wedges 330 tend to resist withdrawal of the connector 56 from the handpiece 54. However, with application of sufficient withdrawal force to the outer sleeve 305, the resistance to withdrawal may be overcome by the action of the distal engagement surfaces 324 of the windows 322 acting on the ramp surfaces 325. The force against the ramp surfaces 325 first pushes the stop surfaces 326 of the wedges 330 against a proximal end of the recess 335, restricting movement of the inner sleeve 308 relative to the handpiece 54. With an increase in the withdrawal force applied to the outer sleeve 305, the distal engagement surfaces 324 of the windows 322 acting against the ramp surfaces 325. The force on the outer sleeve 305 overcomes the resistance of the beams 340 to displace the wedges 330 radially inwardly.

Figure 20A:
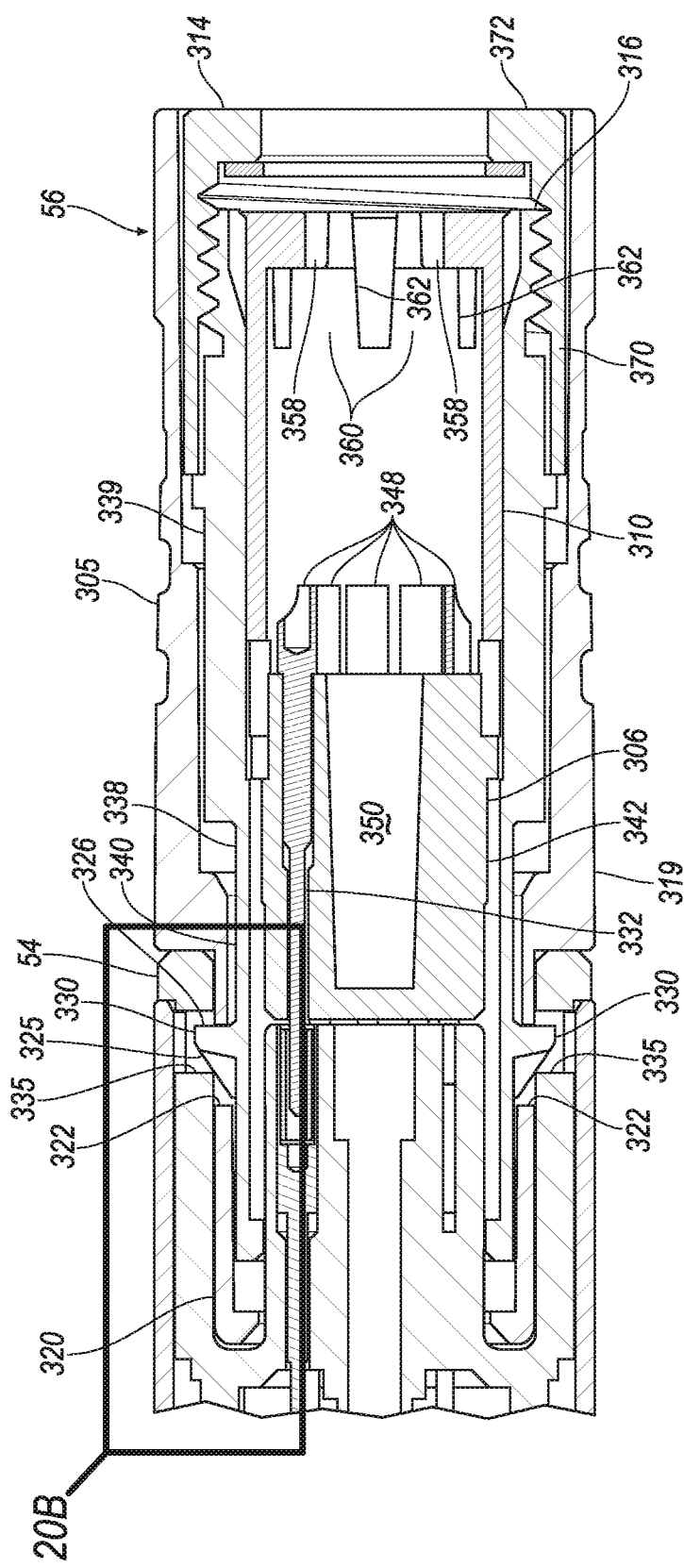
FIG. 20A is a sectional side view of the handpiece and the connector of FIG. 18A in a first position taken through plane 20 in the direction of arrows 20A with plane 20 passing through a center axis of the connector.
Figure 20B:
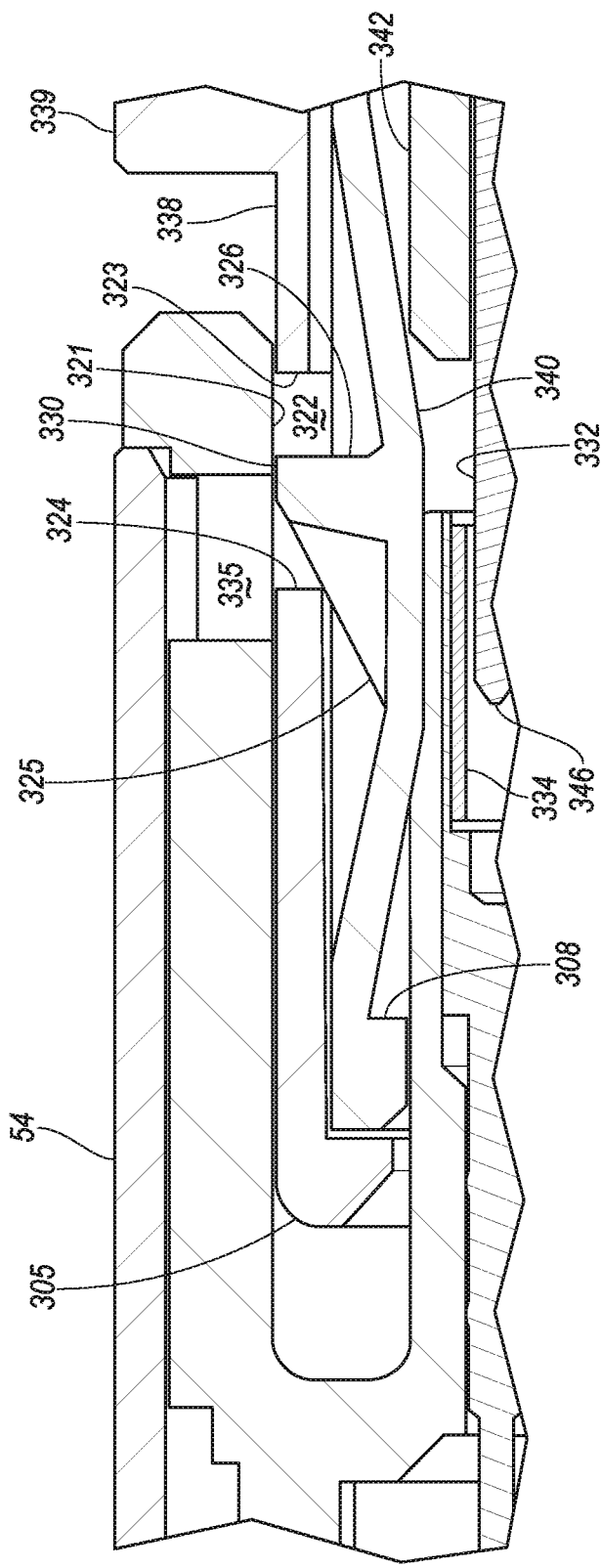
FIG. 20B is a broken-out view of a part of the connector shown in a box 20B in FIG. 20A with the connector in a second position.
Figure 20C:
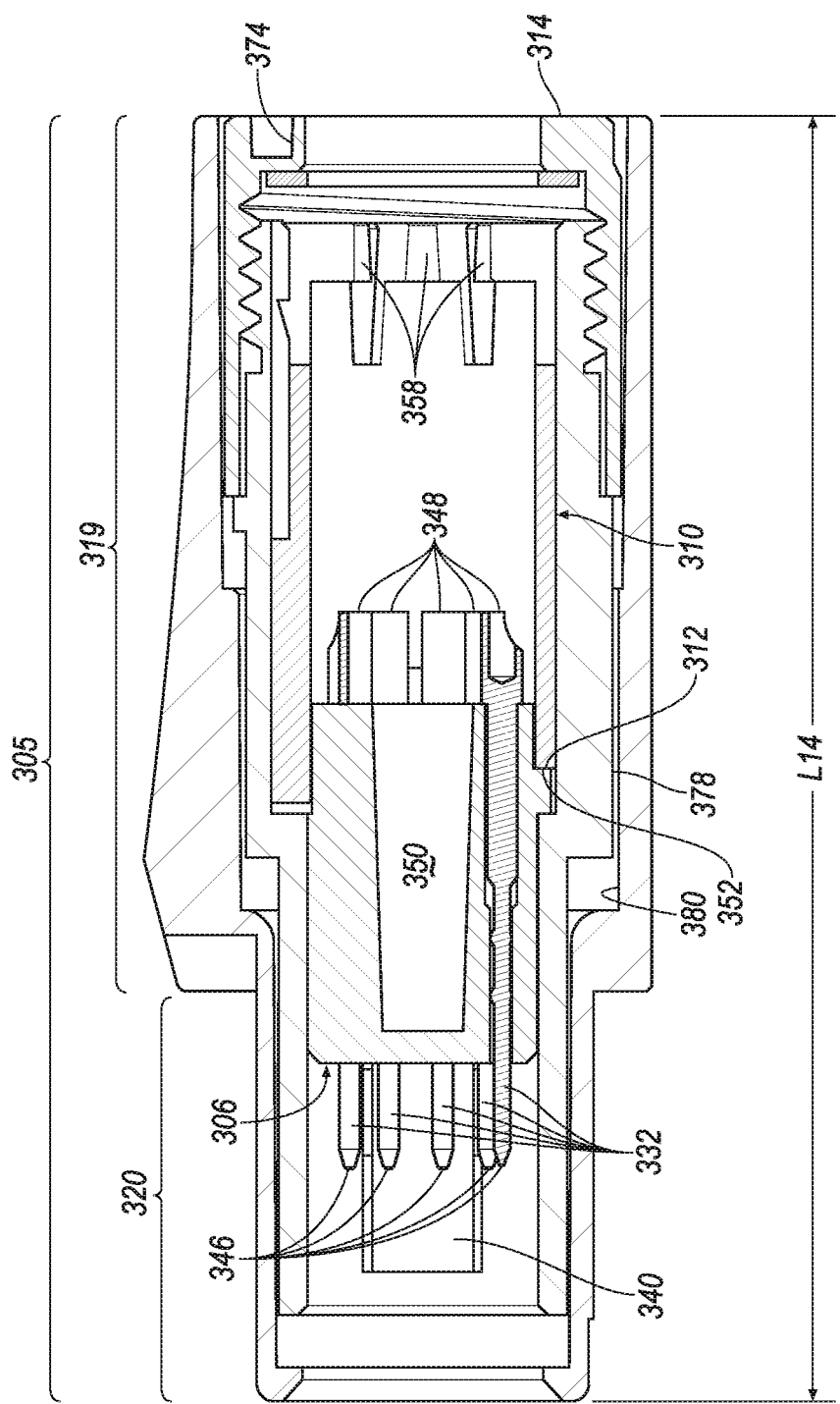
FIG. 20C is a sectional side view of the connector of 18B in the first position taken through plane 20' in the direction of arrows 20C with plane 20' passing through the center axis of the connector.
Figure 21:
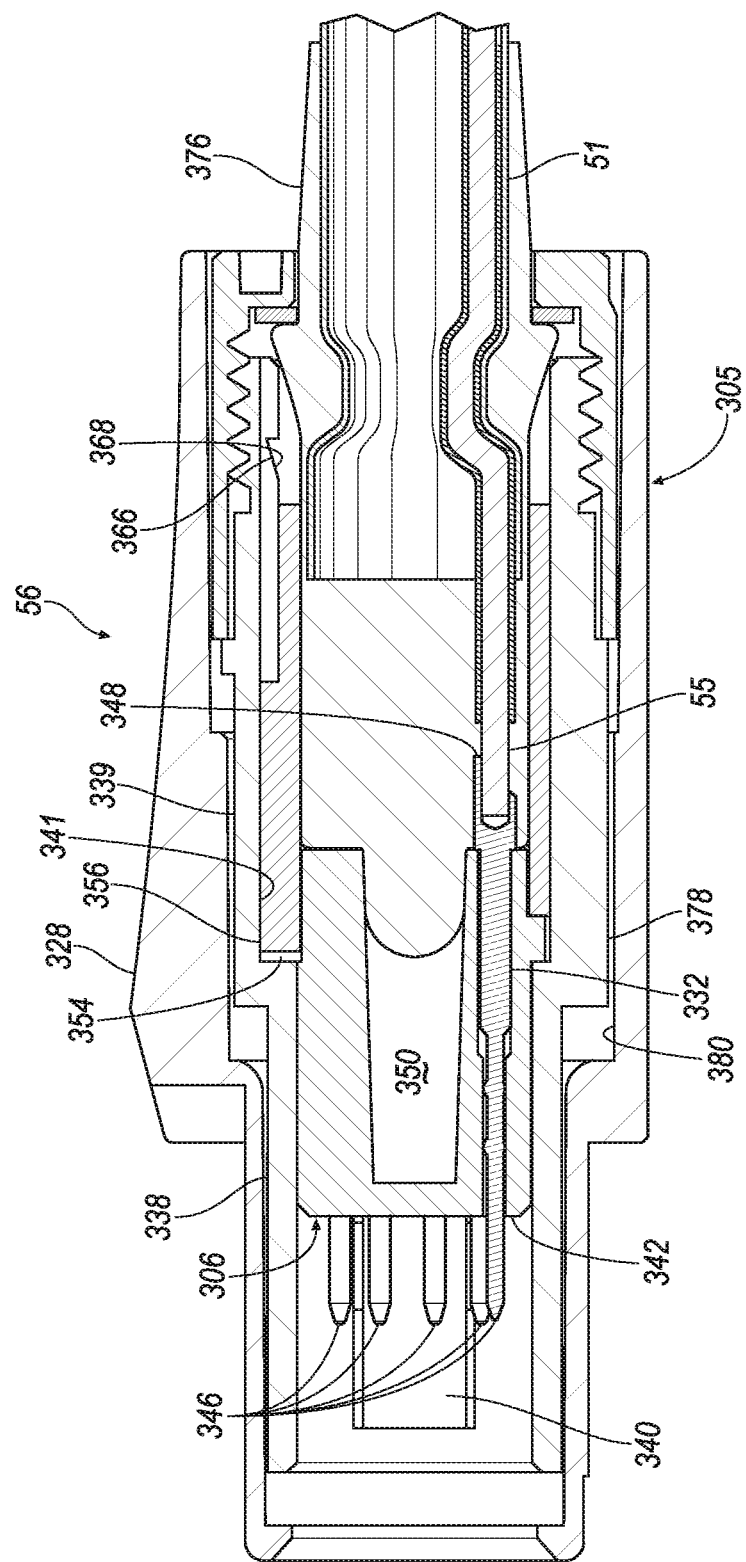
FIG. 21 is a sectional side view of the connector of FIG. 20 C with a cable installed in the connector.

Such displacement of the wedges allows the outer sleeve 305 to move axially relative to the inner sleeve 308 to a releasing position therebetween with the wedges 330 being axially offset from alignment with the windows 322. With the outer sleeve 305 in the releasing position relative to the inner sleeve 308 as shown in FIG. 20B, the wedges 330 are withdrawn, i.e., removed, from the recesses 335. Such removal of the wedges 330 from the recesses 335 allows the connector 56 to be withdrawn from the receptacle 321. Once removed from the handpiece 54, the connector 56 may be restored to the latching position by a restorative force of the beams pressing the ramp surfaces 325 against the distal surfaces 324 of the windows 322 to produce relative axial movement across a slidable range between the inner sleeve 308 and the outer sleeve 305.

Pulling on the cable 51 alone will not result in a release of the connector, as the stop surfaces 326 will engage the proximal end of the recesses 335. Accidental removal of the connector 56 is thus resisted.

In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A powered surgical handpiece including a handswitch, the powered surgical handpiece comprising:
    a mounting base defining a pivot axis;
    an elongated lever defining a lever axis normal to at least a direction of the pivot axis and the lever including:
        a proximal end pivotably connected to the mounting base at the pivot axis,
        a distal end opposite the proximal end,
        a first track on an inner side, and
        a second track on an outer side opposite the inner side with both tracks parallel to the lever axis,
        wherein at least one of the first track and the second track is one of a T-slot and a T-track;
    a spring between the base and the lever biasing the lever about the pivot axis;
    a run-safe switch slidably disposed on the first track; and
    a lever extension slidably disposed on the second track.

2. The powered surgical handpiece of claim 1, wherein the first track and the second track are both T-tracks.

3. The powered surgical handpiece of claim 1, wherein the lever has first and second lateral sides connecting the inner and outer sides and the run-safe switch has at least one outboard side extending laterally beyond at least one of the lateral sides.

4. The powered surgical handpiece of claim 3, wherein the outboard side is defined by an indicator arm.

5. The powered surgical handpiece of claim 1, wherein the lever has a slot in the inner side that is in receipt of at least one of a magnet and a magnet retainer fixed to the run-safe switch.

6. The powered surgical handpiece of claim 5, wherein the slot is shorter in length than a length of the lever and the slot defines a travel range of the run-safe switch.

7. The powered surgical handpiece of claim 1, wherein a detent is disposed between the run-safe switch and the lever.

8. The powered surgical handpiece of claim 7, wherein the detent includes a run-safe switch plunger and a first notch associated with an active position of the run-safe switch and a second notch associated with an inactive position of the run-safe switch.

9. The powered surgical handpiece of claim 8, wherein the run-safe switch plunger is disposed in the lever and the notches are disposed on the switch.

10. The powered surgical handpiece of claim 1, wherein a detent is disposed between the lever and the lever extension.

11. The powered surgical handpiece of claim 10, wherein the detent includes an extension plunger and first, second, third and fourth notches respectively associated with first, second, third and fourth positions of the extension.

12. The powered surgical handpiece of claim 11, wherein the extension plunger is disposed in the lever and the notches are disposed in the lever extension.

13. The powered surgical handpiece of claim 1, wherein the mounting base includes an annular collar that defines a mounting axis normal to at least the direction of the pivot axis and the collar is sized for slideable disposition over a proximal end of the handpiece.

14. The powered surgical handpiece of claim 13, further comprising:
the annular collar defining a positioning tab extending axially in a distal direction and the tab including an angled wedge side; and
one of a detent plunger and a detent notch defining a biasing surface disposed on an inner diameter of the annular collar.

15. The powered surgical handpiece of claim 14, wherein the collar includes at least a second positioning tab, the second positioning tab also extending axially in the distal direction and including an angled wedge side.

16. The powered surgical handpiece of claim 15, wherein the detent plunger is disposed in the collar.

17. A handswitch for a powered surgical handpiece, the handswitch comprising:
a mounting base defining a pivot axis;
an elongated lever defining a lever axis normal to at least a direction of the pivot axis and the lever including:
a proximal end pivotably connected to the mounting base at the pivot axis,
a distal end opposite the proximal end,
a first track on an inner side, and
a second track on an outer side opposite the inner side with both tracks parallel to the lever axis,
wherein at least one of the first track and the second track is one of a T-slot and a T-track;
a spring between the base and the lever biasing the lever about the pivot axis;
a run-safe switch slidably disposed on the first track; and
a lever extension slidably disposed on the second track.

18. The handswitch of claim 17, wherein the mounting base includes an annular collar that defines a mounting axis normal to at least the direction of the pivot axis and the collar is sized for slideable disposition over a proximal end of the handpiece.

19. The handswitch of claim 18, further comprising:
the annular collar defining a positioning tab extending axially in a distal direction and the tab including an angled wedge side; and
one of a detent plunger and a detent notch defining a biasing surface disposed on an inner diameter of the annular collar.

* * * * *